United States Patent [19]

Hegde et al.

[11] Patent Number: 5,129,943

[45] Date of Patent: Jul. 14, 1992

[54] SUBSTITUTED PYRIDINE COMPOUNDS

[75] Inventors: Shridhar G. Hegde, Maryland Heights; Len F. Lee, St. Charles; Robert D. Bryant, St. Louis, all of Mo.

[73] Assignee: Monsanto Company, St. Louis, Mo.

[21] Appl. No.: 702,538

[22] Filed: May 20, 1991

Related U.S. Application Data

[63] Continuation-in-part of Ser. No. 604,655, Nov. 1, 1990, abandoned, which is a continuation-in-part of Ser. No. 457,599, Dec. 27, 1989, abandoned.

[51] Int. Cl.$^5$ ............... A01N 43/40; C07D 413/00
[52] U.S. Cl. .......................... 71/94; 546/313; 546/318; 546/256; 546/261; 546/268; 546/280; 546/281; 546/283; 546/284; 544/82; 544/124; 544/131; 548/374; 548/574; 71/90

[58] Field of Search ............ 546/318, 313, 256, 261, 546/268, 280, 281, 283, 284; 544/124, 82, 131; 548/579, 374; 71/90, 94

[56] References Cited

U.S. PATENT DOCUMENTS

| | | | |
|---|---|---|---|
| 4,609,399 | 9/1986 | Lee et al. | 71/94 |
| 4,692,184 | 9/1987 | Lee et al. | 71/94 |
| 4,885,026 | 12/1989 | Lee et al. | 71/94 |

Primary Examiner—Jose G. Dees
Assistant Examiner—Joseph Conrad, III
Attorney, Agent, or Firm—James C. Bolding; Stanley M. Tarter; Howard C. Stanley

[57] ABSTRACT

Disclosed herein are 2- or 6-fluoromethyl-3-pyridinecarboxylate derivatives with 5-[(heterocyclic-)ylidene]amino substitution useful as herbicides and herbicide intermediates.

16 Claims, No Drawings

SUBSTITUTED PYRIDINE COMPOUNDS

This application is a continuation-in-part application of application Ser. No. 07/604,655 filed Nov. 1, 1990, abandoned which is a continuation-in-part application of application Ser. No. 07/457,599, filed Dec. 27, 1989, now abandoned.

This invention relates to a new class of 2,6-substituted pyridinecarboxylic acid derivatives having a wide range of activity as herbicides, to their use as herbicides, and to herbicidal compositions containing them.

Pyridine derivatives have, for many years, been investigated for use in the biological sciences. Pyridine dicarboxylate compounds useful as herbicides are described in U. S. Pat. No. 4,692,184. These compounds have fluorinated methyl groups at the 2- and 6-positions and carboxylic acids or their derivatives at the 3- and 5-positions and are characterized further by a 4-position substituent in which the atom attached to the pyridine ring is a carbon atom, such as alkyl, alkoxyalkyl, alkylthioalkyl, aralkyl, and like moieties.

Other relevant compounds include those which contain fluorinated methyl groups at the 2- and 6-positions, carboxylic acids or their derivatives at the 3- and/or 5-positions and at the 4-position have a substituent group beginning with a hetero atom selected from O, S, N and P. These compounds are likewise useful as herbicides.

Other herbicidal pyridines are those of U.S. Pat. No. 4,609,399 which have a fluorinated methyl group at the 2-position, a carboxylic acid group or derivative thereof at the 3- and/or 5-position, and alkoxy groups at the 4- and 6-positions.

More relevant to the compounds of this invention are those disclosed in U.S application Ser. No. 861954 filed May 12, 1986 (now U.S. Pat. No. 4,885,026) which are 5-amino pyridine 3-carboxylate derivatives.

BRIEF DESCRIPTION OF THE INVENTION

It is an object of this invention to provide novel pyridine compounds, as well as herbicidal methods and compositions utilizing such compounds.

The novel compounds of this invention are useful as herbicides or intermediates which can be converted to herbicides and are represented by the generic formula

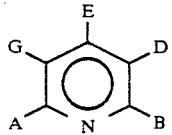

wherein:

one of A and B is selected from the group consisting of fluorinated methyl and chlorofluorinated methyl radicals, and the other is selected from the group consisting of fluorinated methyl, chlorofluorinated methyl, chlorinated methyl, iodinated methyl, alkenyl, and alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynloxycarbonyl, cyano, pyridylthiocarbonyl, aminocarbonyl, monoalkylsubstituted aminocarbonyl, and dialkylsubstituted aminocarbonyl or is the same as D; and D is selected from the group consisting of (tetrahydro-2(H)-pyran-2-ylidene)amino, 2(5H)furanylideneamino, (dihydro-2(3H)-furanylidene)amino, (dihydro-2(3H)-thienylidene)amino, (2-thiazolidinylidene)amino, (1,3-oxathiolan-2-ylidene)amino, (2-morpholinylidene)amino, (1,4-dithian-2-ylidene)amino, (1,3-oxathian-2-ylidene)amino, (1,3-dioxolan-2-ylidene)amino, and (2-pyrrolidinylidene)amino groups, each member of which is optionally substituted on the ring portion with one or more groups selected from alkyl, halo, alkylidene, hydroxy, alkoxy, alkylthio, haloalkyl and alkylsulfonyl radicals.

As used herein throughout the specification and claims, the following terms have the following meanings:

The terms "alkyl" and "lower alkyl" are used interchangeably in this document and mean herein both straight and branched chain saturated hydrocarbon radicals having 1 to 7 carbon atoms, unless a different carbon number range is expressly stated. Examples of such radicals include, but are not limited to, ethyl, methyl, n-propyl, 1-ethylpropyl, 1-methylpropyl, n-butyl, 1,1-dimethylethyl, 2,2- dimethylpropyl, pentyl, isobutyl, isopropyl, and the like.

The term "cycloalkyl" means saturated cyclic radicals having 3 to 7 carbon atoms, such as cyclopropyl, cyclobutyl, cyclopentyl, cyclohexyl, and cycloheptyl.

The terms "alkenyl" and "alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl- 1-propenyl, 2-methyl-2-propenyl, and the like. Examples of such alkynyl groups include ethynyl, 1-propynyl, 2-propynyl, and so forth.

The term "cycloalkylalkyl" is intended to mean alkyl radicals having 1 to 3 carbon atoms which is substituted with a cycloalkyl group having 3 to 7 carbon atoms.

The term "haloalkyl" is intended to mean an alkyl radical (as defined above) substituted with one or more halogen atoms selected from F, Cl, Br, and I, "haloalkenyl" and "haloalkynyl" refer to alkenyl and alkynyl radicals substituted with one or more halogens.

The term "cation" means any monovalent cation derived from a base which is capable of forming a salt. Typical cations include, but are not limited to, alkali metals such as sodium, potassium, and lithium; alkaline earth metals such as calcium and magnesium; and ammonium salts, organic amines, sulfonium and phosphonium salts, and other salt complexes.

The term "fluorinated methyl" means herein methyl radicals having one or more fluorine atoms attached thereto, and includes radicals wherein all hydrogen atoms are replaced by fluorine. The term "chlorofluorinated methyl" means herein a methyl radical having at least one hydrogen replaced by fluorine and at least one other hydrogen replaced by chlorine. The term "chlorinated methyl" means herein methyl radicals having one or more chlorine atoms attached thereto, and includes radicals wherein all hydrogen atoms are replaced by chlorine. The term "iodinated methyl" means herein methyl radicals having one or more iodine atoms attached thereto, and includes radicals wherein all hydrogen atoms are replaced by iodine.

DETAILED DESCRIPTION OF THE INVENTION

Az used throughout the specification, including the Examples and claims, the following abbreviations have the following meanings:

LDA - lithium diisopropylamide
THF - tetrahydrofuran
DME - dimethoxyethane
DBU - 1,8-diazobicyclo-[5.4.0]-undec-7-ene
DMF - N,N-dimethylformamide
ETFAA - ethyl trifluoroacetcacetate
MCPBA - m-chloroperbenzoic acid
HPLC - high pressure liquid chromatography
TLC - thin layer chromatography
n-BuLi - n-butyl lithium
DMSO - dimethyl sulfoxide
Pd/C - hydrogenation catalyst which is palladium deposited on finely-divided carbon
TsCl - tosyl chloride.
AIBN - azo(bis)isobutyronitrile Pyridine cyclic imidate compounds of this invention are prepared by cyclization of a pyridine-4-halobutyramide (or -5-halovaleramide) precursor, which is in turn prepared by reaction of a 3- or 5-amino pyridine with a substituted or unsubstitued 4-halobutyric (or halovaleric) acid chloride The 3- or 5-amino pyridine is prepared from a 3- or 5-chlorocarbonyl pyridine.

Aminopyridines and their preparation from the chlorocarbonyl pyridines (or pyridine acid chlorides) are described in more detail in U.S. Pat. No. 4,885,026 referred to above and which corresponds to European Patent Publication 0252055 which are specifically incorporated herein by reference.

Preparation of the chlorocabonyl pyridines (pyridine acid chlorides) is illustrated below in Steps 1-9. Preparation of the amino pyridines is shown below in examples A-1 to A-10, and preparation of the 4-halobutyramides is shown in Examples B-1 to B-24. Preparation of the pyridine cyclic imidate compounds of this invention is shown following these examples in Examples 1-64.

Preparation of Pyridine 5-Acid Chloride Starting Materials

The compounds of this invention ar prepared using as a starting material a pyridine 3,5-dicarboxylic acid mono-ester mono-chloride or dichloride. Steps 1-9 which follow set out in detail the preparation of three specific acid halides which are used as starting materials for the compounds of this invention. Other acid halides may be readily prepared using the procedures of Steps 1-9 by varying the ketoester and aldehyde used in Step 1 to obtain the desired substituents in the pyridinedicarboxylate product. Other suitable pyridinedicarboxylic acid halide starting materials are shown in U.S. Pat. No. 4,692,184 referred to above in Examples 44-51 and 82-83 inclusive, the disclosure of which is incorporated herein by reference in its entirety. Other acid halide starting materials may be readily prepared using the techniques set out in that U.S. Patent.

The following Steps 1-9 illustrate an example of the procedures for preparation of the acid halide compounds which are the starting materials for making the amides of the present invention. In these steps, a β-ketoester is reacted with an aldehyde to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the β-ketoester, and the 4-position of the pyridine is substituted with the same substituent az is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent to the $CF_2H$ group.

Step 1

Preparation of dimethyl 2,6-bis(trifluoro-methyl)-2,6-dihydroxy-4-isobutyl-tetrahydro-3,5-pyrandicarboxylate.

To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p.. 83°-87° C. and 14.51 g of a second crop, m.p.. 67°-73° C.

The first crop is the desired product which contains a mixture of 5:1 cis and trans isomers.

The second crop is a 2:1 mixture of cis and trans isomers. The mother liquor is concentrated to give 344 g of a residue which is a crude mixture of cis and trans isomer of the desired product.

Step 2

Preparation of dimethyl 2,6-bis(trifluoro-methyl)-2,6-dihydroxy-4-isobutyl-3,5-piperidine-dicarboxylate.

To a solution of 344 g (0.920 mole) crude product from Step 1 in 500 zl of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°-106° C.

The mother liquor is concentrated to provide more of the crude desired product.

Step 3

Preparation of a 2:1 mixture of dimethyl 2,6-bis(trifluoromethyl)-1,4-dihydro-4-isobutyl-3,5-pyridinedicarboxylate and its 3,4-dihydropyridine isomer.

To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L. of ice water The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D{}^{25}$ 1.4391.

Step 3 product may be prepared in better overall yield without isolation of Step 1 and Step 2 product by the following procedure.

To a mechanically stirred mixture of 340.3 g (1.98 mol) of 98.9% pure methyl trifluoroacetoacetate (MTFAA), 100 mL of toluene and 0.86 g (0.01 mol) of piperidine was added 90.5 g (1.03 mol) of isovaleraldehyde in 20 minutes. The reaction mixture exothermed causing a rise of temperature to 83° C. The reaction mixture was maintained at 80° C. for 3 hours. $^{19}$NMR showed that the reaction was 89% complete. Heat was removed, and the reaction mixture was diluted with 125 mL of toluene and stirred overnight (16 hours). Gaseous ammonia was passed through the reaction mixture, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. The reaction mixture was diluted with 100 mL of toluene. A Claisen distillation head was attached to the reaction vessel.

Excess ammonia and parts of toluene were removed in vacuo (water aspirator) while temperature was maintained at 26° C. An additional 200 mL of toluene was added, and the distillation was continued to remove a total of 200 mL of distillate in 1.5 hours. The reaction mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2L of ice water. The toluene layer was separated and the aqueous layer was extracted once with 500 mL of toluene. The combined toluene extracts were washed successively with 500 mL of water, 500 mL of saturated aqueous NaHCO$_3$, then 500 mL of brine and concentrated in vacuo to 363.6 g of an oil. GC area percent analysis indicated that the oil contained 9% of 3,4-dihydropyridine isomer and 75.4% of 4-dihydropyridine isomer corresponding to an overall yield of 82.9% from MTFAA.

Step 4

Preparation of dimethyl 2-(difluoromethyl)-6-(trifluoromethyl)-4-isobutyl-3,5-pyridinedicarboxylate.

(a) Reaction of the Product of Step 3 with DBU

A mixture of 23.0 g (0.0591 mole) of the product of Step 3, 12.2 g (0.077 mole) of 96% pure DBU, and 100 ml of THF is held at reflux for 3 days and poured into 250 ml of 3 N HCl. The oil precipitate is extracted into ether (2×100 ml). The ether extracts are dried (MgSO$_4$) and concentrated to give 14.4 g of an oil which, according to $^1$H NMR, contained the desired product and acidic products. This oil is dissolved in ether and extracted with 100 ml of saturated sodium bicarbonate. The ether layer is dried (MgSO$_4$) and concentrated to give 8.9 g of an oil which is 71% pure desired product (by $^{19}$F NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Step 3) of the desired product as an oil, $n_D{}^{25}$ 1.4478. This product crystallizes after standing, m.p. 36°–37° C.

The 71% pure desired product described previously was purified by HPLC using 3% ethyl acetate/cyclohexane as eluent to give a first fraction (0.79 g, retention time 7–8.5 minutes) which was identified as methyl 6-(difluoromethyl)-4-(iso-butyl)-2-(trifluoromethyl)-3-pyridinecarboxylate. The second fraction (retention time 8.5–18.5 minutes) is an additional 6.4 g (29.4%) of pure desired product, $n_D{}^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. There action mixture was cooled to 30° C. and diluted with 100 ml of toluene. The toluene solution is washed successively with 6 N hydrochloric acid, saturated sodium bicarbonate, and brine, then dried and concentrated to give 36.4 g of a 73% pure product which corresponds to an 86% yield. This reaction can also be carried out in excess of tributylamine (10 equivalents) giving essentially similar results.

(c) Reaction of the Product of Step 3 with Tributylamine in Toluene

A mixture of 38.9 g of an 80% pure product of Step 3, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Triethylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2.6 Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and catalytic amount of DBU without solvent or in the presence of toluene as solvent giving similar results.

Step 5

Preparation of 2-(difluoromethyl)-6-(trifluoromethyl)-4-isobutyl-3,5-pyridinedicarboxylic acid.

A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

Step 6

Preparation of 3.5-bis-(chlorocarbonyl)-2-(difluoromethyl)-4-isobutyl-6-(trifluoromethyl)pyridine.

The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

Step 7

Preparation of methyl 5-chlorocabonyl-2-(difluoromethyl)-4-isobutyl-6-(trifluoromethyl)-pyridine-3-carboxylate.

The product of Step 6 was then dissolved in 100 ml THF followed by 100 ml methanol. After 2½ hours the solvent was evaporated, leaving 31.2 g white solid, m.p. 71°-75° C. in 77% yield.

Step 8

Preparation of 2-(difluoromethyl)-4-isobutyl-6-(trifluoromethyl)-3,5-pyridinedicarboxylic acid, 5-methyl ester.

A 1-liter 4-necked flask was charged with 300 gm of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled consenser. The reaction mixture was heated to reflux, refluxed for 45 minutes and was cooled. The reaction mixture was concentrated and the concentrate was diluted with water and extracted once with ethyl ether. The ether extract (to remove starting material) was discarded. The aqueous solution was acidified with concentrated HCl and the orange precipitate that resulted was extracted with ethyl ether. The aqueous solution was extracted with ether 3 times. The ether extracts were combined and dried over anhydrous magnesium sulfate, filtered and concentrated to yield 253.13 g (87.5% yield) of the monoacid.

Step 9

Preparation of methyl 2-(difluoromethyl)-3-chlorocarbonyl-4-isobutyl-6-(trifluoromethyl)-5-pyridinedicarboxylate.

The acid (253 g, 0.7121 mol) from Step 8 was refluxed for 24 hours in approximately 250-300 ml of thionyl chloride. The reaction mixture was concentrated to yield 244.59 g of acid chloride in 91.9% yield. $n_D^{25}$ 1.4614.

Steps 1-9 above have illustrated the preparation of pyridine carboxylic acid chlorides having a particular set of 2,- 6,- and 4-substituents. Preparation of other acid chlorides will be clear from the foregoing and by reference to U.S. Pat. No. 4,692,184.

Preparation of 5-Aminopyridines

The next step in the sequence for preparing compounds of the present invention is the conversion of the carboxylic acid chloride function of the starting materials shown above to the correspondingly-substituted 5-amino or 3,5-bis amino pyridine. The general procedure for this conversion is shown in Examples A-1 to A-10.

EXAMPLE A-1

3-Pyridinecarboxylic acid, 5-amino-2-(difluoromethyl)-4-(2-methypropyl)-6-(trifluoromethyl)-, methyl ester.

To a stirred solution of 24.4 g (0.375 mol) sodium azide in 100 mL water and 200 mL of acetone at room temperature was added a solution of 55.8 g (0.15 mol) product of Step 7 above in 100 mL of acetone in portions. Following a mild exotherm, the mixture was stirred at room temperature for 4 h. The reaction mixture was concentrated, and diluted with 200 mL water. The mixture was extracted with ethyl ether (2×200 mL), and the combined extracts were washed with water (2×200 mL), dried ($MgSO_4$), and evaporated. The crude product was then vacuum distilled (130° C., 2mm Hg) by Kugelrohr apparatus to afford 44.0 g (91%) of the desired product as a pale yellow sold; mp 48°-50° C. The following amines were made in a similar manner using the general procedure for Example A-1 and starting with the indicated pyridine acid chloride.

EXAMPLE A-2

3-Pyridinecarboxylic acid, 5-amino-4-cyclobutyl-2-(difluoromethyl)-6-(trifluoromethyl)-, methyl ester, 90% yield from 3-pyridinecarboxylic acid, 5- chlorocarbonyl-4-cyclobutyl-2-(difluoromethyl)-6-(trifluoromethyl)-, methyl ester; mp 89°-93° C.

EXAMPLE A-3

3-Pyridinecarboxylic acid, 5-amino-2-(difluoromethyl)-4-methyl-6-(trifluoromethyl)-, methyl ester.

61% yield from 3-pyridinecarboxylic acid, 5-chlorocarbonyl-2-(difluoromethyl)-4-methyl-6-(trifluoromethyl)-, methyl ester; $n_D^{25} = 1.5844$.

EXAMPLE A-4

3-Pyridinecarbonitrile, 5-amino-6-(difluoromethyl)-4-(2-methylpropyl)-2-(trifluoromethyl)

89% yield from 3-pyridinecarbonitrile, 5-chlorocarbonyl-6-(difluoromethyl)-4-(2-methylpropyl)-2-(trifluoromethyl)-.

EXAMPLE A-5

3-Pyridinecarboxylic acid,
5-amino-2-(difluoromethyl)-4-(cyclopropylmethyl)-6-(trifluoromethyl)-, methyl ester 65% from 3-pyridinecarboxylic acid, 5- chlorocarbonyl-4-(cyclopropylmethyl)-2-(difluoromethyl)-6-(trifluoromethyl)-, methyl ester; $n_D^{25} = 1.5885$.

EXAMPLE A-6

3-Pyridinecarbothioic acid,
5-amino-2-(difluoromethyl)-4-(2-methylpropyl)-6-(trifluoromethyl)-, S-methyl ester 83% yield from 3-pyridinecarbothioic acid, 5-chlorocarbonyl-2-(difluoro-methyl)-4-(2-methylpropyl)-6-(trifluoromethyl)-, S-methyl ester; $n_D^{25} = 1.5846$.

EXAMPLE A-7

3,5-Pyridinediamine,
2-(difluoromethyl)-4-(2-methylpropyl)-6-(trifluoromethyl)

97% yield from 3,5-bis-(chlorocarbonyl)-2-(difluoromethyl)-4-(2-methylpropyl)-6-(trifluoromethyl) product of Step 6 above; dark oil; used in further steps without purification, since this material is unstable.

EXAMPLE A-8

3-Pyridinecarboxylic acid,
5-amino-2-(chlorodifluoromethyl)-6-methyl-4-(2-methylpropyl)-, methyl ester This amine was prepared as follows: Step 1: A stirred mixture of 47.17 g (0.30 mol) t-butyl-3-aminocrotonate, 55.98 g (0.30 mol) methyl chlorodifluoroacetoacetate, 25.86 g (0.30 mol) isovaleraldehyde, and about 1 mL piperidine in 400 mL tetrahydrofuran was refluxed overnight. The reaction mixture was concentrated in vacuo to give 117 g (91%) of the dihydroxypiperidine which was used without further purification.

Step 2: To a stirred solution of 42.78 g (0.10 mol) product from Step 1 and 36.04 g (0.36 mol) triethylamine in 200 mL methylene chloride at 5 C was added 29.24 g (0.14 mol) trifluoroacetic anhydride dropwise. The solution was allowed to warm to room temperature and then refluxed for 2 h. The solution was cooled to room temperature and then quenched with 200 mL water. The layers were separated and the aqueous layer was extracted with methylene chloride (3×50 mL). The combined extracts were dried (MgSO4) and evaporated. The residue was eluted through a short column of silica gel and concentrated to afford 39 g (100%) of this intermediate.

Step 3: 3,5-Pyridinedicarboxylic acid. 2-(chlordifluoromethyl)-6-methyl-4-(2-methylpropyl)-, 5-(1,1-dimethylethyl)-3-methyl ester: To a stirred solution of 42.50 g (0.11 mol) product of Step 2 in 200 mL methylene chloride at 0° C. was added 32.3 g (0.14 mol) 2,3-dichloro-5,6-dicyano-1,4-benzoquinone in one portion. The mixture was allowed to warm to room temperature with stirring for 1 h. The mixture was vacuum filtered through celite. The filtrate was washed with saturated sodium bicarbonate and brine, dried (MgSO4), and concentrated. The crude material was purified by column chromatography (30% ethyl acetate:hexane) to afford 16.73 g (39%) of the diester product.

Step 4: A mixture of 115 g (0.29 mol) of material from Step 3 and 300 mL trifluoroacetic acid was stirred at room temperature for 24 h. The mixture was concentrated in vacuo, and the residue was dissolved in ethyl ether. The ether solution was washed with water, dried (MgSO4), and concentrated to afford 90 g (91%) of the product of this step as a grey solid.

Step 5: 3-Pyridinecarboxylic acid, 2-(chlorodifluoromethyl)-5- [[(1,1-dimethylethoxy)carbonyl]amino]-6-methyl-4-(2-methylpropyl)-, methyl ester: A stirred mixture of 5.25 g (0.0156 mol) material from Step 4, 4.74 g (0.0172 mol) diphenylphosphoryl azide, and 2.63 g (0.0172 mol) DBU in 75 mL t-butanol was refluxed for 5 h. The mixture was concentrated, and the residue was partitioned with ethyl acetate (100 mL) and water (100 mL). The aqueous layer was extracted with ethyl acetate (2×50 mL). The combined organic extracts were washed with brine (2×50 mL), dried (MgSO4), and evaporated. The crude material was purified by chromatography (HPLC, 10% ethyl acetate:hexane). Evaporation of the appropriate fractions and trituration of the oily residue afforded 2.88 g (45%) of the desired product as a white solid; mp 111°-113° C.

Step 6: A mixture of 6.00 g (0.0147 mol) product of Step 5, 25 mL trifluoroacetic acid, and 30 mL methylene chloride in a nitrogen atmosphere was stirred at 25° C. overnight. The reaction mixture was concentrated, and the residue was partitioned with ethyl ether (100 mL) and sat. sodium bicarbonate solution. The organic layer was dried (MgSO4) and concentrated to afford 4.50 g (100%) of the title compound as a pale yellow solid. Analytically pure material was obtained by chromatography (20% ethyl acetate:hexane); mp 69°-71° C.

EXAMPLE A-9

3-Pyridinecarboxylic acid,
5-amino-4-methyl-2,6-bis(trifluoromethyl)-, ethyl ester This compound was prepared by the following three-step method:

Step 1: 3,5-Pyridinedicarboxylic acid, 4-methyl-2,6-bis(trifluoromethyl)-, monoethyl ester: A stirred mixture of 10.90 g (0.029 mol) the compound of Example 2 of U.S. Pat. No. 4,692,184, 200 mL ethanol, and 13 mL (0.032 mol) 10% w/v sodium hydroxide solution was refluxed for 2 h. The mixture was concentrated, and then diluted with 300 mL water. The mixture was extracted with ethyl ether. The aqueous phase was acidified with concentrated HCl. The aqueous phase was extracted with ethyl ether (3×200 mL). The combined extracts were dried (MgSO4) and evaporated. The crude material was recrystallized in hexane:ethyl acetate to afford 8.60 g (86%) of the desired product as off-white crystals; mp 128°-130°.

Step 2: A stirred slurry of 7.14 g (0.021 mol) product of Step 1 and 4.80 g (0.023 mol) phosphorous pentachloride in 75 mL carbon tetrachloride was stirred at room temperature overnight in absence of moisture. The resulting clear solution was evaporated affording 7.60 g (100%) of the acid chloride as a yellow oil. Step 3: To a stirred solution of 4.00 g (0.062 mol) sodium azide in 40 mL water and 40 mL acetone was added a solution of 7.60 g (0.021 mol) of product from Step 2 in 50 mL acetone in portions. Following the addition the mixture was stirred overnight at room temperature. The mixture was concentrated, and the residue was diluted with 100 mL water. The mixture was extracted with ethyl ether (3×50 mL). The combined extracts were dried (MgSO4) and evaporated to afford 6.71 g (100%) of the desired compound as a pale yellow oil which crystallized on standing. The analytically pure title compound was obtained by chromatographic purification (30% ethyl acetate:hexane); mp 51°-53°.

EXAMPLE A-10

3-Pyridinecarboxylic acid, 5-(amino)-2-(1-methylethyl)-4-(2-methyl-propyl)-6-(trifluoromethyl), methyl ester Step 1: 3,5-Pyridinedicarboxylic acid, 2-(1-methylethyl)-4-(2-methylpropyl)-6-(trifluoromethyl): A stirred mixture of 11.14 g (0.032 mol) 3,5-pyridinedicarboxylic acid, 2-(1-methylethyl)-4-(2-methylpropyl)-6-(trifluoromethyl), dimethyl ester (prepared using the methodology set out in Examples 150 and 151 of U.S. Pat. No. 4,692,184) in 100 mL hydrazine monohydrate was refluxed for 4 h. The mixture was then cooled to room temperature and poured into 300 mL crushed ice. The resulting slurry was acidified by careful addition of concentrated hydrochloric acid (pH<1). The mixture was extracted with diethyl ether (3×150 mL). The combined extracts were dried (MgSO4) and evaporated affording 7.23 g (68%) of the desired product as a pale yellow solid; mp >200° C. Step 2: A slurry of 6.41 g (0.019 mol) of the diacid from Step 1 and 8.41 g (0.040 mol) phosphorous pentachloride in 100 mL carbon tetrachloride was stirred overnight at room temperature. The resulting clear solution was concentrated in vacuo. The residue was dissolved in 50 mL anhydrous tetrahydrofuran and 5 mL methanol at room temperature. The mixture was stirred for 10 days. The solution was then concentrated in vacuo and dissolved in 50 mL acetone. The solution was added in portions to a stirring solution of 3.09 g (0.048 mol) sodium azide in 25 mL water and 25 mL acetone and then allowed to stir overnight at room temperature. The mixture was concentrated, and then partitioned with ethyl ether and water. The ether layer was dried (MgSO4) and concentrated. The residue was purified by chromatography (HPLC, 5% ethyl acetate:hexane) to afford 3.16 g of the desired product as a pale brown oil. This product was used in the synthesis of Example B-21 without further characterization.

The 4-halobutyramide precursors of the compounds of this invention are made as shown in the following Examples B-1 to B-24.

EXAMPLE B-1

3-Pyridinecarboxylic acid, 5-[(4-bromo-1-oxobutyl) amino]-4-cyclobutyl-2-(difluoromethyl)-6-(trifluoromethyl)-, methyl ester A stirred mixture of 5.10 g (0.016 mol) of product of Example A-2 and 3.63 g (0.020 mol) 4-bromobutyryl chloride in 40 mL anhydrous toluene was refluxed overnight. The mixture was allowed to cool to room temperature. Upon cooling, the precipitated product was collected by vacuum filtration on a Buchner funnel. Recrystallization in ethyl acetate-hexane provided 4.92 g (66%) of the desired product as an off-white solid: mp 167°-169° C.

The amide intermediate in Example B-2 and the haloamide intermediates of Examples B-3 to B-16 and B-18 to B-20 below were prepared using the same general procedure as that shown in Example B-1.

EXAMPLE B-2

3-Pyridinecarboxylic acid, 2-(difluoromethyl)-4-(2-methylpropyl)-5-[(1-oxo-4-pentenyl)amino]-6-(trifluoromethyl)-, methyl ester 63% yield from product of Example A-1 and 4-pentenoic acid chloride in THF solution at 75° C.; reaction time 3 d; mp 122°-124° C.

EXAMPLE B-3

3-Pyridinecarbothioic acid. 5-[(4-bromo-1-oxobutyl) amino]-2-(difluoromethyl)-4-(2-methylpropyl)-6-(trifluoromethyl)-, S-methyl ester 65% yield from product of Example A-6 and 4-bromobutyryl chloride; reaction time 12 h; mp 147°-148° C.

EXAMPLE B-4

3-Pyridinecarboxylic acid, 5-[(5-bromo-1-oxopentyl) amino -2-(difluoromethyl)-4-(2-methylpropyl)-6-(trifluoromethyl)-, methyl ester 26% from product of Example A-1 and 5-bromopentanoyl chloride; reaction time 48 h; mp 94°-96° C.

EXAMPLE B-5

3-Pyridinecarboxylic acid, 5-[(4-chloro-2-methyl-1-oxobutyl)amino]-2-(difluoromethyl)-4-(2-methylpropyl)-6-(trifluoromethyl)-, methyl ester 55% from product of Example A-1 and 4-chloro-2-methylbutanoyl chloride; reaction time 48 h; mp 118°-120° C.

EXAMPLE B-6

3-Pyridinecarboxylic acid, 5-[(4-chloro-3-methyl-1-oxobutyl)amino]-2-(difluoromethyl)-4-(2-methylpropyl)-6-(trifluoromethyl), methyl ester 29% yield from product of Example A-1 and 4-chloro-3-methylbutanoyl chloride; reaction time 48 h; mp 109°-111° C.

EXAMPLE B-7

3-Pyridinecarboxylic acid, 5-[(2,4-dichloro-1-oxobutyl)amino]-2-(difluoromethyl)-4-(2-methylpropyl)-6-(trifluoromethyl)-, methyl ester 68% from product of Example A-1 and 2,4-dichlorobutanoyl chloride; reaction time 12 h; mp 104°-106° C.

EXAMPLE B-8

3-Pyridinecarboxylic acid, 5-[(4-bromo-2-methylene-1-oxobutyl)amino]-2-(difluoromethyl)-4-(2-methylpropyl)-6-(trifluoromethyl)-, methyl ester 48% from product of Example A-1 and 4-bromo-2-(bromomethyl)butanoyl chloride; reaction time 4 d; mp 106°-108° C.

EXAMPLE B-9

3-Pyridinecarboxylic acid,
5-[(4-bromo-2-methyl-1-oxobutyl)amino]-2-(difluoromethyl)-4-(2-methylpropyl)-6-(trifluoromethyl)-,
methyl ester 81% from product of Example A-1 and 4-bromo-2-methylbutanoyl chloride; reaction was done without a solvent at 60° C. overnight; mp 120°–122° C.

EXAMPLE B-10

3-Pyridinecarboxylic acid,
5-[(4-bromo-2-fluoro-1-oxobutyl)amino]-2-(difluoromethyl)-4-(2-methylpropyl)-6-(trifluoromethyl), methyl ester 89% from product of Example A-1 and 4-bromo-2-fluorobutanoyl chloride at 60° C. overnight; mp 121°–122° C.

EXAMPLE B-11

3-Pyridinecarboxylic acid,
5-[(4-bromo-1-oxobutyl)amino]-2-(difluoromethyl)-4-methyl-6-(trifluoromethyl)-, methyl ester 96% from product of Example A-3 and 4-bromobutanoyl chloride at 60° C. overnight; mp 98°–100° C.

EXAMPLE B-12

Butanamide,
N,N'-(2-(difluoromethyl)-4-(2-methylpropyl)-6-(trifluoromethyl)-3,5-pyridinediyl[bis[4-bromo]

32% from product of Example A-7 and 4-bromobutanoyl chloride at room temperature overnight; mp 234° C. (decomp.).

EXAMPLE B-13

Butanamide,
4-bromo-N-(5-cyano-2-(difluoromethyl)-4-(2-methylpropyl)-6-(trifluoromethyl)-3-pyridinyl]-

64% from product of Example A-4 and 4-bromobutanoyl chloride; mp 175°–180° C.

EXAMPLE B-14

3-Pyridinecarboxylic acid,
5-[(4-bromo-2-(methylthio)-1-oxobutyl]amino]-2-(difluoromethyl)-4-(2-methylpropyl)-6-(trifluoromethyl)-,
methyl ester 61% from product of Example A-1 and 4-bromo-2-(methylthio)butanoyl chloride at 60°–80° C. for 30 h; mp 103°–105° C.

EXAMPLE B-15

3-pyridinecarbothioic acid.
5-[(4-bromo-2-methyl-1-oxobutyl)amino]-2-(difluoromethyl)-4-(2-methylpropyl)-6-(trifluoromethyl)-,
S-methyl ester 97% yield from product of Example A-6 and 4-bromo-2-methylbutanoyl chloride; m.p. 120°–121° C.

EXAMPLE B-16

3-Pyridinecarboxylic acid,
5-[(4-bromo-2,2-dimethyl-1-oxobutyl)amino]-2-(difluoromethyl)-4-(2-methylpropyl)-6-(trifluoromethyl)-,
methyl ester 33% from product of of Example A-1 and 4-bromo-2,2-dimethylbutanoyl chloride; reaction time 96 h.

EXAMPLE B-17

3-Pyridinecarboxylic acid,
5-[(2-bromo-4-iodo-1-oxobutyl)amino]-2-(difluoromethyl)-4-(2-methylpropyl)-6-(trifluoromethyl)-, methyl ester A stirred mixture of 5.62 g (0.010 mol) of product of Example B-20 and 1.63 g (0.011 mol) of sodium iodide in 30 mL acetone was refluxed for 1 hour. The solvent was evaporated, and the residue was partitioned with water (100 mL) and ethyl ether (150 mL). The organic layer was washed with water (2×30 mL), dried (MgSO₄) and evaporated. The crude material was filtered through silica gel, and trituration of the oily residue with hexane:methyl ether afforded 4.72 g (78%) of the desired product as a white solid; mp 111°–113° C.

EXAMPLE B-18

3-Pyridinecarboxylic acid, 5-[(4-bromo-1-oxobutyl)amino]-2-(difluoromethyl)-4-(2-methylpropyl)-6-(trifluoromethyl)-,methyl ester 72% from product of Example A-1; m.p. 95°–96°.

EXAMPLE B-19

3-Pyridinecarboxylic acid, 5-[(4-bromo-1-oxobutyl)amino]-4-(cyclopropylmethyl)-2-(difluoromethyl)-6-(trifluoromethyl)-, methyl ester 70% yield from product of Example A-5; mp 60°–61° C.

EXAMPLE B-20

3-Pyridinecarboxylic acid,
5-[(2,4-dibromo-1-oxobutyl)amino]-2-(difluoromethyl)-4-(2-methylpropyl)-6-(trifluoromethyl)-, methyl ester 31% from product of Example A-1 and 2,4-dibromobutyryl chloride; reaction time 72 h; mp 115° C.

EXAMPLE B-21

3-Pyridinecarboxylic acid,
5-[(4-bromo-1-oxobutyl)amino]-2-(1-methylethyl)-4-(2-methylpropyl)-6-trifluoromethyl)-, methyl ester A solution of 2.66 g (0.0084 mol) product of Example A-10 and 1.85 g (0.010 mol) 4-bromobutyryl chloride in 15 mL anhydrous toluene was refluxed for 4 h. The mixture was allowed to cool to room temperature. Trituration of the solution with hexane:ethyl ether gave 2.30 g of the desired product as a white solid. The remaining filtrate from the reaction mixture was concentrated, and the residue was purified by chromatography (10% ethyl acetate:hexane) to give an additional 0.93 g product for a total yield of 82%; mp 135°–136° C.

The following compounds were made in a similar manner to that shown in Example B-21:

EXAMPLE B-22

3-Pyridinecarboxylic acid,
5-[(4-bromo-1-oxobutyl)amino)-2-(chlorodifluoromethyl)-6-methyl-4-(2-methylpropyl)-. methyl ester 17% from product of Example A-8 and 4-bromobutyryl chloride refluxed for 2 h.

EXAMPLE B-23

3-Pyridinecarboxylic acid,
5-[(4-bromo-1-oxobutyl)amino]-4-methyl-2,6-bis(trifluoromethyl), ethyl ester 60% from product of Example A-9 and 4-bromobutyryl chloride refluxed in toluene for 10 h; mp 141°–142° C.

EXAMPLE B-24

3-Pyridinecarboxylic acid,
5-[(4-bromo-2-methoxy-1-oxobutyl)amino]-2-(difluoromethyl)-4-(2-methylpropyl)-6-(trifluoromethyl)-, methyl ester 56% from product of Example A-1 and 4-bromo-2-methoxybutyryl chloride refluxed in toluene for 30 h; mp 113°–115° C.

Preparation of the pyridine cycloimidate compounds of this invention is shown in the following Examples 1–64.

EXAMPLE 1

3-Pyridinecarboxylic acid,
2-(difluoromethyl)-4-(2-methylpropyl)-5-(tetrahydro-2H-pyran-2-ylidene)amino]-6-(trifluoromethyl)-, methyl ester To a stirred solution of 2.87 g (0.0059 mol) of product of Example B-4 in 75 mL methylene chloride was added 1.30 g (0.0067 mol) silver tetrafluoroborate in one portion at room temperature. The resulting slurry was stirred for 30 min. and, this was followed by addition of 100 ml of saturated sodium bicarbonate solution for an additional 30 min. The mixture was vacuum filtered through a celite pad to remove the precipitated silver salts. The filtrate layers were separated, and the organic layer was dried (MgSO4) and evaporated. The crude material was purified by HPLC (20% ethyl acetate-hexane) to afford 1.60 g (67%) of the desired product as a pale yellow wax: $n_D^{25} = 1.58475$.

EXAMPLE 2

3-Pyridinecarboxylic acid,2-(difluoromethyl)-5-[(dihydro-3-methyl-2(3H)-furanylidene)amino]-4-(2-methylpropyl)-6-(trifluoromethyl)-, methyl ester To a stirred solution of 2.00 g (0.0045 mol) of product of Example B-5 in 25 mL of methylene chloride was added 1.05 g (0.0054 mol) silver tetrafluoroborate in one portion. The resulting slurry was stirred for 1 h, and this was followed by the addition of 100 mL sat. sodium bicarbonate and stirring for an additional 30 min. The mixture was filtered through celite to remove the precipitated silver salts, and the layers were separated. The organic layer was dried (MgSO4) and evaporated. The residue was purified by chromatography (20% ethyl acetate-hexane to afford 1.30 g (71%) of the desired product as a clear coloress wax; $n_D^{25} = 1.5820$;

This compound may be similarly prepared using the product of Example B-9.

The following compounds of Examples 3–16 were made by the same general procedures as those shown above in Examples 1–2.

EXAMPLE 3

3-Pyridinecarboxylic acid,
2-(difluoromethyl)-5-[diydro-4-methyl-2(3H)-furanylidene)amino]-4-(2-methylpropyl)-6-(trifluoromethyl)-methyl ester 84% yield from product of Example B-6; $n_D^{25} = 1.58221$.

EXAMPLE 4

3-Pyridinecarboxylic acid,
5-[(3-bromodihydro-2(3H)-furanylidene)amino]-2-(difluoromethyl)-4-(2-methylpropyl)-6-(trifluoromethyl)-, methyl ester 64% from product of Example B-17; $n_D^{25} = 1.5842$.

EXAMPLE 5

3-Pyridinecarboxylic acid,
5-[3-chlorodihydro-2(3H)-furanylidene)amino]-2-(difluoromethyl)-4-(2-methylpropyl)-6-(trifluoromethyl)-, methyl ester 77% from product of Example B-7; $n_D^{25} = 1.5836$.

EXAMPLE 6

3-Pyridinecarboxylic acid,
2-(difluoromethyl)-5-[(dihydro-3,3-dimethyl-2(3H)-furanylidene)amino]-4-(2-methylpropyl-6-(trifluoromethyl)-, methyl ester 34% from product of Example B-16; $n_D^{25} = 1.5850$.

EXAMPLE B 7

3-Pyridinecarboxylic acid,
2-(difluoromethyl)-5-[3-fluorodihydro-2(3H)-furanylidene)amino]-4-(2-methylpropyl)-6-(trifluoromethyl)-, methyl ester 80% from product of Example B-10; $n_D^{25} = 1.5825$.

EXAMPLE 8

3-Pyridinecarboxylic acid,
2-(difluoromethyl)-5-[(dihydro-3-methylene-2(3H)-furanylidene)amino]-4-(2-methylpropyl)-6-(trifluoromethyl)-,methyl ester 66% from product of Example B-8; $n_D^{25} = 1.5802$.

EXAMPLE 9

3-Pyridinecarboxylic acid,
2-(difluoromethyl)-5-[(dihydro-2(3H)-furanylidene)amino]-4-methyl-6-(trifluoromethyl), methyl ester 79% from product of Example B-11; $n_D^{25} = 1.5842$.

EXAMPLE 10

3,5-Pyridinediamine,
2-(difluoromethyl)-N,N'-bis(dihydro-2(3H)-furanylidene)-4-(2-methylpropyl)-6-(trifluoromethyl)

84% from product of Example B-12; mp 98°–102° C.

EXAMPLE 11

3-Pyridinecarbonitrile, 6-(difluoromethyl)-5-[(dihdro-2(3H)-furanylidene)amino]-4-(2-methylpropyl)-6-(trifluoromethyl)

55% from product of Example B-13; mp 68°–69° C.

EXAMPLE 12

3-Pyridinecarboxylic acid, 2-(difluoromethyl)-5-[(dihydro-3-(methylthio)-2-(3H)-furanylidene)amino]-4-(2-methylpropyl)-6-(trifluoromethyl),methyl ester 81% from product of Example B-14; $n_D^{25}=1.5860$.

EXAMPLE 13

3-Pyridinecarboxylic acid, 4-cyclobutyl-2-(difluoromethyl)-5-[(dihydro-2(3H)-furanylidene)amino]-6-(trifluoromethyl)-, methyl ester 56% from product of Example B-1; $n_D^{25}=1.5861$.

EXAMPLE 14

3-Pyridinecarbothioic acid, 2-(difluoromethyl)-5-[(dihydro-2(3H)-furanylidene)amino]-4-(2-methylpropyl)-6-(trifluoromethyl)-, S-methyl ester 72% from product of Example B-3; mp 89°–91° C.

EXAMPLE 15

3-Pyridinedicarboxylic acid, 2-(difluoromethyl)-5-(dihydro-2(3H)-furanylidene)-4-(2-methylpropyl)-6-(trifluoromethyl)-, methyl ester 71% from product of Example B-18; $n_D^{25}=1.5876$.

EXAMPLE 16

3-Pyridinecarboxylic acid, 4-(cyclopropylmethyl)-2-(difluoromethyl)-5-[(dihydro-2(3)-furanylidene)amino]-6-(trifluoromethyl)-, methyl ester 91% from product of Example B-19; $n_D^{25}=1.5865$.

The following compounds of the present invention were made as shown, some of them being derived from the compounds shown above.

EXAMPLE 17

3-Pyridinecarboxylic acid, 5-[[5-(bromomethyl)dihydro-2(3H)-furanylidene]amino]-2-(difluoromethyl)-4-(2-methylpropyl)-6-(trifluoromethyl)-, methyl ester To a mixture of 3.3z g (0.0083 mol) of product of Example B-2 in 100 mL carbon tetrachloride was added enough methylene chloride to dissolve the amide completely. To this solution was added a solution of 1.32 g (0.0083 mol) of bromine in 25 mL carbon tetrachloride dropwise at room temperature. Following the addition, the reaction mixture was partitioned with 100 mL 25% sodium thiosulfate solution, and the layers were allowed to separate. The organic layer was dried (MgSO4) and evaporated. The crude product (4,5-dibromobutyramide) was dissolved in 50 mL methylene chloride. To this solution was added 1.62 g (0.0083 mol) silver tetrafluoroborate with stirring in one portion. After 30 min., saturated sodium bicarbonate solution (50 mL) was added with stirring for an additional 10 min. The reaction mixture was vacuum filtered through celite and the layers were allowed to separate. The organic layer was dried (MgSO4) and evaporated. The crude material was purified by HPLC (20% ethyl acetate-hexane) to afford 3.19 g (79%) of the desired product as a pale yellow viscous oil: $n_D^{25}=1.5827$.

EXAMPLE 18

3-Pyridinecarboxylic acid, 2-(difluoromethyl)-5-[(dihydro-5-methyl-2(3H)-furanylidene)amino]-4-(2-methyl-propyl)-6-(trifluoromethyl)-,methyl ester A mixture of 2.31 g (0.0047 mol) of product of Example 17, 1.51 g (0.0052 mol) of tributyltin hydride, and 20 mg of AIBN in 25 mL of benzene under nitrogen was refluxed for 2 h. The benzene was evaporated, and the residue was purified by chromatography (10% ethyl acetate-hexane) to afford 1.40 g (72%) of the desired product as colorless oil: $n_D^{25}=1.5807$.

EXAMPLE 19

3-Pyridinecarboxylic acid, 2-(difluoromethyl)-5-(2(5H)-furanylideneamino)-4-(2-methylpropyl)-6-(trifluoromethyl)-, methyl ester To a stirred solution of 2.50 g (0.0053 mol) of product of Example 4 in 25 mL anhydrous THF at 0° C. was added 0.97 g (0.0064 mol) of DBU in portion. The mixture was allowed to warm to room temperature and stirred for 3 h. The solvent was evaporated from the blackened mixture, and the residue was partitioned with ethyl ether (75 mL) and water (75 mL). The organic layer was dried (MgSO4) and evaporated. The black residue was purified by HPLC (20% ethyl acetate-hexane) to afford 0.82 g (39%) of the desired product as a light amber wax: $n_D^{25}=1.5805$.

EXAMPLE 20

3-Pyridinecarboxylic acid, 2-(difluoromethyl)-5-[(dihydro-2(3H)-furanylidene)amino]-4-(2-methylpropyl)-6-(trifluoromethyl)

A mixture of 5.04 g (0.013 mol) of product of Example 15 and 25 mL 10% NaOH in enough methanol to give a clear solution was stirred at room temperature overnight. The mixture was concentrated and then diluted with 200 mL water and extracted with 50 mL of ethyl ether. The aqueous layer was acidified with 10% HCl solution (pH<1). The mixture was extracted with ethyl ether (3×100 mL). The combined extracts were dried (MgSO4) and evaporated. The crude product was recrystalized with hexane-ethyl acetate to afford 3.95 g (81%) of a white solid: mp 140°–148° C.

EXAMPLE 21

3-Pyridinecarboxylic acid, 2-(dichloromethyl)-5-[(dihydro-2(3H)-furanylidene)amino]-4-(2-methylpropyl)-6-(trifluoromethyl)-, methyl ester To a solution of 6.59 g (0.016 mol) of product of Example 15 in 50 mL methylene chloride was added 6.05 g (0.045 mol) of aluminum chloride in 0.50 g portions. The solution was stirred for two hours at room temperature, then was poured over sodium bicarbonate solution. The emulsion was filtered through celite and the filtrate was partitioned in methylene chloride and water. The organic layer was dried (MgSO4) and concentrated. HPLC purification of the residue (25% ethyl acetate-hexane) afforded 4.73 g (66.3%) of product as a pale yellow solid: mp 76°–77° C.

EXAMPLE 22

3-Pyridinecarboxylic acid, 2-(chloromethyl)-5-[(dihydro-2(3H)-furanylidene)amino]-4-(2-methylpropyl)-6-(trifluoromethyl)-, methyl ester To a solution of 4.99 g (0.012 mol) product of Example 21 in anhydrous tetrahydrofuran at −78° C. was added 6.29 mL (0.024 mol) tributyltin hydride dropwise.

The mixture was stirred at reflux for 16 hours and the solvent was removed by evaporation. The residue was dissolved in ether and washed with water. The organic layer was dried (MgSO$_4$) and concentrated. HPLC purification of the mixture (CHCl$_3$) afforded 1.76 g (37%) of a first fraction which was the title compound: $n_D^{25}=1.5780$.

EXAMPLE 23

3-Pyridinecarboxylic acid, 5-[(dihydro-2(3H)-furanylidene)amino]-2-methyl-4-(2-methylpropyl)-6-(trifluoromethyl)-, methyl ester A second fraction from the HPLC purification of the product mixture in Example 22 afforded 1.66 g (39%) of this compound as a coloress oil: $n_D^{25}=1.5910$.

EXAMPLE 24

3-Pyridinecarboxylic acid, 2-(difluoromethyl)-5-[(dihydro-2(3H)-furanylidene)amino]-4-(2-methylpropyl-6-(trifluoromethyl-, ethyl ester To a mixture of 2.06 g (0.0054 mol) product of Example 20 and 1.36 g (0.0066 mol) of dicyclohexylcarbodiimide (DCC) in 30 mL anhydrous acetonitrile was added 0.64 g (0.014 mol) of absolute ethanol in one portion The mixture was refluxed overnight, then vacuum filtered to remove the solids. The filtrate was concentrated, and the residue was purified by chromatography (20% ethyl acetate-hexane) to afford 0.92 g (42%) of the desired product as a pale yellow waxy oil: $n_D^{25}=1.5840$.

The compounds of the following Examples 25–31 were made using the general procedure shown in Example 24.

EXAMPLE 25

3-Pyridinecarboxylic acid, 2-(difluoromethyl)-5-[(dihydro-2(3H)-furanylidene)amino]-4-(2-methylpropyl)-6-(trifluoromethyl)-, 2-fluoroethyl ester 36% from product of Example 20 and 2-fluoroethanol; $n_D^{25}=1.5852$.

EXAMPLE 26

3-Pyridinecarboxylic acid, 2-(difluoromethyl)-5-[(dihydro-2(3H)-furanylidene)amino]-4-(2-methylpropyl)-6-(trifluoromethyl)-, 2-propenyl ester 29% from product of Example 20 and allyl alcohol; $n_D^{25}=1.5842$.

EXAMPLE 27

3-Pyridinecarboxylic acid, 2-(difluoromethyl)-5-[(dihydro-2(3H)-furanylidene)amino]-4-(2-methylpropyl)-6-(trifluoromethyl), 2-propynyl ester 46% from product of Example 20 and propargyl alcohol; $n_D^{25}=1.5862$.

EXAMPLE 28

3-Pyridinecarboxamide, 2-(difluoromethyl)-5-[(dihydro-2(3H)-furanylidene)amino]-4-(2-methylpropyl)-N-(phenylmethyl)-6-(trifluoromethyl)

38% from product of Example 20 and benzylamine; mp 141°–142° C.

EXAMPLE 29

3-Pyridinecarboxamide, N-butyl-2-(difluoromethyl)-5-[(dihydro-2(3H)-furanylidene)amino]-4-(2-methylpropyl)-6-(trifluoromethyl)

29% from product Example 20 and n-butyl amine; mp 120°–121° C.

EXAMPLE 30

3-Pyridinecarbothioic acid, 2-(difluoromethyl)-5[(dihydro-2(3H)-furanylidene)amino]-4-(2-methylpropyl)-6-(trifluoromethyl)-, S-2-pyridinyl ester 45% from product of Example 20 and 2-mercaptopyridine; $n_D^{25}=1.7058$.

EXAMPLE 31

3-Pyridinecarboxamide, N-(4-chlorophenyl)-2-(difluoromethyl)-5-[(dihydro-2(3H)-furanylidene)amino]-4-(2-methylpropyl)-6-(trifluoromethyl)

20% from product of Example 20 and 4-chloroaniline; mp 179°–180° C.

EXAMPLE 32

3-Pyridinecarboxylic acid, 4-(bromomethyl)-2-(difluoromethyl)-5-[(dihydro-2(3H)-furanylidene)amino]-6-(trifluoromethyl), methyl ester A stirred mixture of 2.37 g (0.0067 mol) of product of Example 9, 1.42 g (0.008 mol) N-bromosuccinimide, and catalytic AIBN (azo(bis)isobutyronitrile, approx. 0.002 g) in 20 mL of carbon tetrachloride was refluxed overnight. The reaction mixture was vacuum filtered, and the filtrate was concentrated. The crude material was purified by HPLC (33% ethylacetate-hexane) to afford 1.45 g (50%) of the desired product as a pale amber waxy oil, which later solidified: mp 54°–56° C.

EXAMPLE 33

3-Pyridinecarboxylic acid, 2-(difluoromethyl)-5-[(dihydro-2(3H)-furanylidene)amino]-4[methylthio)methyl]-6-(trifluoromethyl), methyl ester To a stirred solution of 2.00 g (0.0046 mol) product of Example 32 in anhydrous 50 mL of THF at 0° C. was added 0.33 g (0.0047 mol) sodium methanethiolate in one portion. The resulting slurry was allowed to ware to room temperature and stir for an additional 1 h. To the reaction mixture was added 75 mL of water. The THF was evaporated, and the residue was partitioned with ethyl ether. The layers were separated, and the aqueous layer was extracted with additional ethyl ether (2×25 mL). The combined extracts were dried (MgSO$_4$) and evaporated. The crude material was purified by HPLC (33% ethyl acetate-hexane) to afford 1.44 g (78%) of the desired product as a yellow wax: $n_D^{25}$=1.5847.

EXAMPLE 34

3-Pyridinecarboxylic acid, 2(difluoromethyl)-5-[(dihydro-2(3H)-furanylidene)amino]-4-[(dimethylamino)methyl]-6-(trifluoromethyl)-, methyl ester To a stirred solution of 3.23 g (0.0075 mol) product of Example 32 in 25 mL of methanol at room temperature was added 4 mL of (0.023 mol) 26% w/v aqueous dimethylamine solution. Enough additional methanol was added to obtain a clear solution. The mixture was stirred for 5 h. The reaction mixture was concentrated in vacuo. The residue was partitioned with ethyl ether (100 mL) and water (75 mL). The organic layer was dried (MgSO$_4$) and concentrated. The crude material was purified by HPLC (33% ethyl acetate-hexane) to afford 142 g (40%) of the desired product as a pale yellow wax; $n_D^{25}$=1.5856.

EXAMPLE 35

3-Pyridinecarboxylic acid, 2-(difluoromethyl)-5-[(dihydro-2(3H)-furanylidene)amino]-4-(2-propenyl)-6-(trifluoromethyl)-, methyl ester A mixture of 3.86 g (0.009 mol) product of Example 32, 3.78 g of (0.012 mol) vinyl tributyl tin, catalytic amount of benzylchlorobis (triphenylphosphine) palladium (II) (approx. 0.1 g) in 10 mL anhydrous DMF was stirred at 60°–70° C. for 3.5 h. The reaction mixture was then diluted with 60 mL of aqueous KF solution and extracted with ethyl ether (3×50 mL). The combined extracts were dried (MgSO$_4$) and evaporated. The crude material was purified by HPLC (1:2 ethyl acetate:hexane). A second HPLC purification (methylene chloride) afforded 0.80 g (24%) of the desired product as a colorless oil: $n_D^{25}$=1.5851.

EXAMPLE 36

3-Pyridinecarboxylic acid, 2-(difluoromethyl)-5-[(dihydro-3-(methylsulfonyl)-2(3H)-furanylidene)amino]-4-(2-methylpropyl)-6-(trifluoromethyl), methyl ester To a stirred solution of 1.72 g (0.004 mol) of product of Example 12 in 20 mL of methylene chloride at 0° C. was added 1.86 g (0.0085 mol) m-chloro-peroxybenzoic acid in one portion The mixture was allowed to ware to room temperature, and then stirred for 3 h. Saturated sodium bicarbonate (40 mL) was added with stirring for 30 min. The layers were separated, and the aqueous layer was extracted with additional methylene chloride (2×20 mL). The combined extracts were dried (MgSO$_4$) and evaporated. The crude material was purified by HPLC (1:2 ethyl acetate:hexane), and trituration of the appropriate fractions afforded 1.75 g (95%) of the desired product as an off-white solid; mp 118°–121° C.

EXAMPLE 37

3-Pyridinecarbothioic acid, 2-(difluoromethyl)-5-[(dihydro-2(3H)-thienylidene)amino]-4-(2-methylpropyl)-6-(trifluoromethyl)-, S-methyl ester A slurry of 5.51 g (0.011) product of Example B-3 and 2.45 g (0.012 mol) phosphorous pentachloride in 60 mL carbon tetrachloride was stirred overnight at room temperature. The resulting clear solution was concentrated in vacuo to afford 5.70 g (100%) of the desired intermediate as a clear oil with no further purification necessary. A slurry of this oil and 0.72 g (0.016 mol) of lithium sulfide in 30 mL anhydrous THF was stirred at room temperature overnight. The solvent was evaporated, and the residue was partitioned with ethyl ether (150 mL) and 10% HCl (150 mL). The organic layer was dried (MgSO$_4$) and evaporated. The crude material was purified by HPLC (15% ethyl acetate-hexane) to afford 1.54 g (35%) of the desired product as a clear wax; $n_D^{25}$=1.5842.

EXAMPLE 38

3-Pyridinecarboxylic acid, 2-(difluoromethyl)-4-(2-methylpropyl)-5-(dihydro-2(3H)-thienylidene)amino-6-(trifluoromethyl)-, methyl ester Made by the general procedure of Example 37 in 31% yield from product of Example B-18; $n_D^{25}$=1.5824.

EXAMPLE 39

3-Pyridinecarboxylic acid, 2-(difluoromethyl)-4-(2-methylpropyl)-5-[(2-thiazolidinylidene)amino]-6-(trifluoromethyl)-, methyl ester Step A 3-Pyridinecarboxylic acid, 2-(difluoromethyl)-5-(formylamino)-4-(2-methylpropyl)-6-(trifluoromethyl)-methyl ester To 76 mL of acetic anhydride at 0° C. was added 38 mL of 80% formic acid. This was allowed to warm to room temperature and then heated at 50° C. for 15 minutes. The resulting formic acetic anhydride was cooled to 0° C. and 9.72 g (0.03 mol) of product of Example A-1 was added. The reaction mixture was stirred at room temperature for 48 hours, then concentrated in vacuo and heated on the Kugelrohr distillation apparatus (70° C., 0.7 mm). Trituration of the oily residue with hexane afforded a white solid which was recrystallized from hexane-ether to obtain 9.5 g (89%) of the product colorless crystals: m.p. 119°–120° C.

Step B

3-Pyridinecarboxylic acid, 5-(dichloromethylene)amino-2-(difluoromethyl)-4-(2-methylpropyl)-6-(trifluoromethyl)-, methyl ester To 25 mL of thionyl chloride at 0° C. was added 6.996 g (0.52 mol) of sulfuryl chloride. To this mixture was added 10.59 g (0.30 mol) product of Step A in one portion. The mixture was allowed to warm to room temperature, and then refluxed for 48 hours. The thionyl chloride was removed in vacuo affording 10.2 g (84%) of the desired product as a light yellow semisolid which was used without further purification.

Step C

To a solution of 4.25 g (0.01 mol) product of Step B in 25 mL of chloroform at 0° C. was added 1.55 g (0.014) of 2-amino-ethanethiol dropwise. Following the thiol addition, 4.11 g (0.034 mol) of 4-dimethylaminopyridine in 30 mL of chloroform was added dropwise over a period of 15 min. The mixture was allowed to ware to room temperature, and the solvent was evaporated. The residue was partitioned with ethyl ether (75 mL) and 10% HCl solution (50 mL). The organic layer was washed with water (3×30 mL), dried (MgSO$_4$), and evaporated. Trituration of the residue with hexane afford 1.01 g (23%) of the desired product as a colorless solid: mp 133°-135° C.

EXAMPLE 40

3-Pyridinecarboxylic acid, 2-(difluoromethyl)-4-(2-methylpropyl)-5-[(3-methyl-2-thiazolidinylidene)amino]-6-(trifluoromethyl)-, methyl ester To a solution of 3.20 g (0.0078 mol) of product of Example 39 in 20 mL of anhydrous THF under N$_2$ at −78° C. was added 8 mL (0.008 mol) of 1M sodium bis(trimethylsilyl) azide in THF. The mixture was stirred for 1 hour, after which 5.68 g (0.04 mol) of iodomethane was added. The mixture was allowed to warm to room temperature and stirred overnight. The reaction mixture was diluted with 100 mL water and extracted with ethyl acetate (3×100 mL), dried (MgSO$_4$), and evaporated. Purification of the crude product by chromatography (10% ethyl acetate-hexane) afforded 1.54 g (47%) of the desired product as a pale yellow oil: $n_D^{25} = 1.15826$.

EXAMPLE 41

3-Pyridinecarboxylic acid, 2-(difluoromethyl)-4-(2-methylpropyl)-5-[(1,3-oxathiolan-2-ylidene)amino]-6-(trifluoromethyl)-, methyl ester

Step A

3-Pyridinecarboxylic acid, 2-(difluoromethyl)-5-(isothiocyanato)-4-(2-methylpropyl)-6-(trifluoromethyl)-, methyl ester To a solution of 4.00 g (0.01 mol) of product of Step B of Example 39 in 25 mL anhydrous THF at room temperature under nitrogen was added 0.54 g (0.012 mol) of lithium sulfide in one portion. The mixture was stirred overnight, and afterwards the solvent was evaporated. The residue was partitioned with ethyl ether (150 mL) and water (100 mL). The organic layer was washed with water (3×30 mL), dried (MgSO$_4$), and evaporated. The crude material was purified by HPLC (5% ethyl acetate-hexane) to afford 2.43 g (67%) of the desired product as a colorless oil: $n_D^{25} = 1.5865$.

Step B

A mixture of 2.25 g (0.006 mol) of product of Step A, 0.50 g (0.0062 mol) of 2-chloroethanol, and 0.76 g of (0.0062 mol) 4-dimethylaminopyridine in 25 mL anhydrous toluene was refluxed for 4 hours. Following the reaction period, the toluene was evaporated, and the residue was partitioned with ethyl ether (100 mL) and 10% HCl solution (50 mL). The ether layer was washed with water (3×30 mL), dried (MgSO$_4$), and evaporated. The crude material was purified by chromatography (25% ethyl acetate-hexane) to afford 2.30 g (91%) of the desired product as a colorless wax: $n_D^{25} = 1.5847$.

EXAMPLE 42

3-Pyridinecarboxylic acid, 2-(difluoromethyl)-5-[(4-methyl-3-morpholinylidene)amino]-4-(2-methylpropyl)-6-(trifluoromethyl)-, methyl ester

Step A

3-Pyridinecarboxylic acid, 5-[(bromoacetyl)amino]-2-(difluoromethyl)-4-(2-methylpropyl)-6-(trifluoromethyl)-, methyl ester A stirred mixture of 2.76 g (0.0085 mol) product of Example A-1 and 2.25 g (0.011 mol) bromoacetylbromide in 50 mL anhydrous toluene was refluxed for 5 h. The toluene was evaporated, and the residue was triturated with hexane-ethyl ether to afford 2.65 g (70%) of the desired product as a colorless solid; mp 163°-164° C.

Step B

3-Pyridinecarboxylic acid, 2-(difluoromethyl)-4-(2-methylpropyl)-5-[(bromomethyl)chloroimino]-6-(trifluoromethyl), methyl ester A stirred slurry of 8.22 g (0.18 mol) product of Step A and 4.20 g (0.20 mol) phosphorous pentachloride in 150 mL carbon tetrachloride was stirred overnight in absence of moisture. The reaction mixture was gravity filtered, and solvent was evaporated affording 8.00 g (93%) of the desired product as pale amber oil. The product was used for subsequent reactions without purification.

Step C

3-Pyridinecarboxylic acid, 5-[[2-bromo-1-[2-hydroxyethyl)methylamino]ethylidene]amino]-2-(difluoro-methyl)-4-(2-methylpropyl-6-(trifluoromethyl), methyl ester To a solution of 3.72 g (0.008 mol) product of Step B in 15 mL anhydrous THF was added 2.40 g (0.032) 2-(methylamino)ethanol dropwise. Following the addition, the mixture was stirred overnight at room temperature. The solvent was evaporated, and the residue was partitioned with ethyl ether (50 mL) and water (50 mL). The organic layer was dried (MgSO$_4$) and evaporated. The crude material was purified by chromatography (10% ethyl acetate-hexane) to give 0.86 g (21%) of the desired product as a colorless wax: $n_D^{25} = 1.5811$.

Step D

To a solution of 2.59 g (0.005 mol) product of Step C in 10 mL anhydrous THF under nitrogen at −78° C. was added 7 mL (0.007 mol) of a 1 molar solution of sodium bis (trimethylsilyl)amide. The mixture was allowed to warm to room temperature and stirred overnight. The mixture was quenched with 25 mL of saturated ammonium chloride and concentrated. The residue was partitioned with ethyl ether (50 mL) and water (50 mL). The organic layer was dried (MgSO$_4$) and evaporated. The residue was purified by chromatography (10% ethyl acetate-hexane) to yield 1.10 g (51%) of an amber oil: $n_D^{25} = 1.5847$.

EXAMPLE 43

3-Pyridinecarboxylic acid,
2-(difluoromethyl)-5-(1,4-dithian-2-ylideneaminol)]-4-
(2-methylpropyl)-6-(trifluoro-methyl)-, methyl ester To a solution of 4.92 g (0.011 mol) product of Step B of Example 42 in 20 mL anhydrous THF at 0° C. was added 2.50 g (0.026 mol) 1,2-ethanedithiol. To this stirred mixture, 2.84 g (0.024 mol) 4-dimethylaminopyridine was added in portions. Followng the addition, the mixture was allowed to warm to room temperature, and the solvent was evaporated. The residue was partitioned with ethyl ether (100 mL) and 5% HCl solution (75 mL). The organic layer was washed with water (3×30 mL), dried (MgSO$_4$), and evaporated. The residue was purified by chromatography (5% ethyl acetate-hexane) to afford 1.66 g (35%) of the desired product as a pale yellow oil: n$_D^{25}$=1.5830.

EXAMPLE 44

3-Pyridinecarboxylic acid,
2-(difluoromethyl)-4-(2-methylpropyl)-5-(1,3-oxathian-
2-ylideneamino)-6-(trifluoromethyl)-, methyl ester A mixture of 2.25 g (0.006 mol) product of Step A of Example 41, 0.85 g (0.006 mol) 3-bromo-1-propanol, and 0.74 g (0.006 mol) 4-dimethylaminopyridine in 25 mL anhydrous toluene was refluxed for 4 h. Following the reaction period, the toluene was evaporated, and the residue was partitioned with ethyl ether (100 mL) and 10% HCl solution (100 mL). The ether layer was washed with water (3×30 mL), dried (MgSO$_4$), and evaporated. The crude material was purified by chromatography (10% ethyl acetate-hexane) to afford 1.38 g (53%) of the desired product as a colorless wax: n$_D^{25}$=1.5871.

EXAMPLE 45

3-Pyridinecarbothioic acid,
2-(difluoromethyl)-5-[(dihydro-3-methyl-2(3H)-
furanylidene)amino
-4-(2-methylpropyl)-6-(trifluoromethyl)-, S-methyl
ester 42% from product of Example B-15; n$_D^{25}$=1.5950.

EXAMPLE 46

3-Pyridinecarboxylic acid,
2-(difluoromethyl)-5-[3-ethyldihydro-2(3H)-
furanylidene)amino]-4-(2-methylpropyl)-6-(tri-
fluoromethyl)-, methyl ester To a solution of 3.94 g (0.01 mol) of product of Example 15 in 100 mL of anhydrous THF at −78° C. was added dropwise 12 mL (0.012 mol) of 1 M solution of sodium bis(trimethylsily)amide over a period of 10 min. The solution was stirred at −78° C. for 1 h, after which 5 mL of ethyl iodide was added and the mixture was slowly warmed to room temperature. After stirring at room temperature for 6 h, the reaction was quenched by adding 10 mL of saturated ammonium chloride solution. The solution was concentrated by evaporation, the residue was diluted with water, and the resulting suspension was extracted with three 100 mL portions of ethyl acetate. The organic layers were combined and washed with water, dried over anhydrous magnesium sulfate, and evaporated. Purification of the residue by HPLC afforded 2.4 g (56.9%) of product as a pale yellow oil: n$_D^{25}$=1.5832.

EXAMPLE 47

3-Pyridinecarboxylic acid,
2-(difluoromethyl)-5-(1,3-dioxolan-2-ylideneamino)-4-
(2-methylpropyl)-6-(trifluoromethyl)-, methyl ester

Step A

3-Pyridinecarboxylic acid,
2-(difluoromethyl)-5-[[(2-hydroxyethoxy)carbonyl-
]amino]-4-(2-methylpropyl)-6-(trifluoromethyl)-,
methyl ester To a stirred suspension of 7.8 g (0.12 mol) of sodium azide in a mixture of 100 mL of ethylene glycol and 100 mL of acetone was added a solution of 18.6 g (0.05 mol) of the 5-chlorocarbonyl pyridine shown in Step 7 above in 50 mL of acetone in small portions. The reaction mixture was stirred at room temperature overnight, and then concentrated to remove most of the acetone. The mixture was diluted with water and extracted with three 200 mL portions of ethyl acetate. The combined organic layers were washed with water, dried over anhydrous magnesium sulfate, and evaporated. Purification of the residue by HPLC gave 16.6 g (80%) of intermediate as a white solid: mp 104° C.

Step B

3-Pyridinecarboxylic acid,
5-[[2-chloroethoxy)carbonyl]amino]-2-(difluorome-
thyl)-4-(2-methylpropyl)-6-(trifluoromethyl)-, methyl
ester A solution of 13.6 g (0.033 mol) of product of Step A in 100 mL of thionyl chloride was refluxed for 4 h. The solution was then evaporated and the residue was partitioned between 200 mL of chloroform and 200 mL of water. The organic layer was dried over anhydrous magnesium sulfate and evaporated. Purification of the residue by HPLC afforded 10.6 g (74%) of this intermediate as a white solid: mp 95°–96° C.

Step C

To a solution of 6.48 g (0.015 mol) of product of Step B in 200 mL of methylene chloride was added 3.3 g (0.017 mol) of silver tetrafluoroborate in one portion. the resulting suspension was stirred at room temperature for 10 h after which 200 mL of saturated sodium bicarbonate solution was added and stirring was continued for an additional 45 min. The mixture was filtered to remove insoluble salts and the salts were washed with 200 mL of methylene chloride. The organic layer in the combined filtrates was separated, dried over anhydrous magnesium sulfate, and evaporated. Purification of the residue by HPLC afforded 5.5 g (92.6%) of title compound as a white solid: mp 101°–102° C.

Examples 48 and 49 were each prepared in three steps, with each of the three steps being performed similarly to the corresponding step in Example 47.

EXAMPLE 48

3-Pyridinecarboxylic acid,
2.-(difluoromethyl)-5-[(4-methyl-1,3-dioxolan-2-ylidene)amino]-4-(2-methylpropyl)-6-(trifluoromethyl)-, methyl ester

Step A

3-Pyridinecarboxylic acid, 2-(difluoromethyl)-5-[[(2-hydroxypropoxy)carbonyl]amino]-4-(2-methylpropyl)-6-(trifluoromethyl)-, methyl ester 63% yield from product of Step 7 above and sodium azide in propylene glycol/acetone; mp 97°-99° C.

Step B

3-Pyridinecarboxylic acid, 5-[[(2-chloroethoxy)carbonyl]amino]-2-(difluoromethyl)-4-(2-methylpropyl)-6-(triflууoromethyl)-, methyl ester 79.8% yield from product of Step A; mp 94°-96° C.

Step C

73% yield from product of Step B as a colorless oil; $n_D^{25} = 1.5955$.

EXAMPLE 49

3-Pyridinecarboxylic acid, 2-(difluoromethyl)-5-[(4,5-dimethyl-1,3-dioxolan-2-ylidene)amino]-4-(2-methylpropyl)-6-(trifluoromethyl)-, methyl ester

Step A

3-Pyridinecarboxylic acid, 2-(difluoromethyl)-5-[[2-hydroxy-1-methylpropoxy)-carbonyl]amino]-4-(2-methyl propyl)-6-(trifluoromethyl), methyl ester 52.5% yield from product of Step 7 above and sodium azide in 2,3-butanediol/acetone; mp 137°-138° C.

Step B

3-Pyridinecarboxylic acid, 5-[[(2-chloro-1-methylpropoxy)carbonyl]amino]-2-(difluoromethyl)-4-(2-methylpropyl)-6-(trifluoromethyl)-, methyl ester 88% yield from product of Step A; mp 108°-110° C.

Step C 75.5% yield from product of Step B as a colorless oil; $n_D^{25} = 1.5982$.

EXAMPLE 50

3-Pyridinecarboxylic acid, 2-(difluoromethyl)-5-[(1-methyl-2-pyrrolidinylidene)amino]-4-(2-methylpropyl)-6-(trifluoromethyl)-, methyl ester A solution of 1.63 g (0.005 mol) of product of Example A-1, 1 g (0.0068 mol) of N-methylpyrrolidone dimethyl acetal, and 0.1 g of p-toluenesulfonic acid in 25 mL of toluene was heated at reflux for 20 h. Evaporation of the solvent followed by HPLC purification of the residue gave 1.5 g (73.7%) of product as a colorless oil; $n_D^{25} = 1.6160$.

EXAMPLE 51

3-Pyridinecarboxylic acid, 5-[(dihydro-2(3H)-furanylidene)amino]-2-(1-methylethyl)-4-(2-methylpropyl)-6-(trifluoromethyl)-, methyl ester A mixture of 2.39 g (0.0051 mol) product of Example B-21 and 2.30 g (0.012 mol) silver tetrafluoroborate in 100 mL methylene chloride was vigorously stirred for 30 min at room temperature. Saturated sodium bicarbonate (100 mL) was added to the reaction mixture with stirring for an additional 30 min. The mixture was vacuum filtered through celite, and the layers were separated. The aqueous layer was extracted with methylene chloride (2×30 mL), and the combined organic layers were dried (MgSO$_4$) and evaporated. The crude material was purified by chromatography (30% ethyl acetate:hexane) to afford 1.68 g (85%) of the desired product as a colorless wax; $n_D^{25} = 1.5996$.

The following compounds of Examples 52–54 were prepared similarly to the general procedure set out in Example 51:

EXAMPLE 52

3-Pyridinecarboxylic acid, 2-(chlorodifluoromethyl)-5-[(dihydro-2(3H)-furanylidene)amino]-6-methyl-4-(2-methypropyl)-, methyl ester 62% yield from product of Example B-22; $n_D^{25} = 1.5142$.

EXAMPLE 53

3-Pyridinecarboxylic acid, 5-[(dihydro-2(3H)furanylidene)amino]-4-methyl-2,6-bis(trifluoromethyl)-, ethyl ester 96% yield from product of Example B-23; $n_D^{25} = 1.5835$.

EXAMPLE 54

3-Pyridinecarboxylic acid, 2-(difluoromethyl)-5-[(dihydro-3-methoxy-2(3H)-furanylidene)amino]-4-(2-methylpropyl)-6-(trifluoromethyl)-, methyl ester 90% from product of Example B-24; $n_D^{25} = 1.5956$.

The following compounds of Examples 55–68 were prepared using the method set out for each.

EXAMPLES 55

3-Pyridinecarboxylic acid, 2-(difluoromethyl)-5-[(dihydro-3-hydroxy-2(3H)-furanylidene)amino]-4-(2-methylpropyl)-6-(trifluoromethyl)-, methyl ester A stirred solution of 3.53 g (0.0087 mol) product of Example 8 in 40 mL methylene chloride at −78° C. was treated by slowly bubbling ozone through the solution for a period of 8 h. To the ozonated solution was added a solution of 1.50 g (0.040 mol) sodium borohydride in 50 mL ethanol dropwise with mechanical stirring. The resulting mixture was stirred overnight, and then quenched by slow addition of 200 mL 10% HCl solution. The layers were separated, and the aqueous layer was extracted with methylene chloride (2×200 mL). The combined organic layers were dried (MgSO$_4$) and evaporated. The crude material was purified by chromatography (HPLC, 30% ethyl acetate:hexane) to afford 1.59 g (45%) of the desired product as a clear colorless wax; $n_D^{25} = 1.5845$.

EXAMPLE 56

3-Pyridinecarboxylic acid, 2-(difluoromethyl)-5-[(dihydro-3-methyl-2(3H)-furanylidene)amino]-4-(2-methylpropyl)-6-(trifluoromethyl)-

A stirred mixture of 9.94 g (0.024 mol) product of Example 2, 50 mL (0.12 mol) 10% w/v sodium hydroxide solution, and enough methanol to provide a clear solution (approx. 200 mL) was refluxed for 1 h, and then stirred overnight at room temperature. The mixture was concentrated, and then diluted with 200 mL water. The mixture was extracted with 200 mL ethyl ether, and the aqueous layer was acidified with 25% HCl solution to pH 1. The aqueous material was extracted with ethyl ether (3×100 mL). The combined extracts were dried (MgSO$_4$) and evaporated. The residue was triturated with hexane:ethyl ether to afford 8.77 g (93%) of the desired product as a white solid; mp 163°–165° C.

EXAMPLE 57

3-Pyridinecarboxylic acid, 2-(difluoromethyl)-5-[(dihydro-3-methyl-2(3H)-furanylidene)amino]-4-(2-methylpropyl)-6-(trifluoromethyl)-, ethyl ester A stirred mixture of 5.05 g (0.013 mol) product of Example 56, 3.18 g (0.015 mol) 1,3-dicyclohexylcarbodiimide, and 0.52 g (0.033 mol) ethanol in 100 mL anhydrous acetonitrile was refluxed overnight. The reaction mixture was cooled to room temperature and filtered. The filtrate was concentrated, and the residue was purified by chromatography (HPLC, 10% ethyl acetate:hexane) to afford 4.37 g (81%) of the desired product as a colorless wax; $n_D^{25} = 1.5855$.

EXAMPLE 58

3-Pyridinecarboxylic acid, 2-(dichloromethyl)-5-[(dihydro-3-methyl-2(3H)-furanylidene)amino]-4-(2-methylpropyl)-6-(trifluoromethyl)-, methyl ester To a stirred solution of 35.10 g (0.086 mol) product of Example 2 in 200 mL methylene chloride was added 35.1 g (0.26 mol) aluminum chloride in 5 g portions over a period of 30 min. A mild exotherm accompanied the addition, and the mixture was stirred an additional 1 h. The darkened mixture was poured into an ice water:sodium bicarbonate slurry; considerable foaming occurs during this step. Following this quenching process, concentrated HCl was cautiously added to dissolve the aluminum hydroxide precipitate. The mixture was then extracted with ethyl ether (3×200 mL). The combined extracts were dried (MgSO$_4$) and evaporated. The crude material was vacuum filtered through a plug of silica gel (40% hexane:chloroform) and collected in 1L portions. Workup of the appropriate fractions afforded 22.12 g (58%) of the desired product at 97% purity as a yellow wax; $n_D^{25} = 1.5860$. An additional 8.0 g of product was collected at 80% purity.

EXAMPLE 59

3-Pyridinecarboxylic acid, 2-(chloromethyl)-5-[(dihydro-3-methyl-2(3H)-furanylidene)amino]-4-(2-methylpropyl)-6-(trifluoromethyl), methyl ester A stirred mixture of 20.12 g (0.046 mol) product of Example 58, 15.0 g (0.052 mol) tributyltin hydride, and catalytic azobisisobutyronitrile (approx. 0.10 g) in 150 mL anhydrous THF was refluxed for 1 h. An additional 2.0 g (0.006 mol) tributyltin hydride was added with additional refluxing until starting material was less than 4% by chromatographic analysis. The mixture was concentrated, and the residue was purified by chromatography (40% hexane:chloroform). Workup of the appropriate fractions afforded 13.71 g (73%) of the desired product as a pale green wax; $n_D^{25} = 1.5997$.

EXAMPLE 60

3-Pyridinecarboxylic acid, 2-(difluoromethyl)-5-[(3-fluorodihydro-3-methyl-2(3H)-furanylidene)amino]-4-(2-methylpropyl)-6-(trifluoromethyl)-, methyl ester To a stirred solution of 3.37 g (0.0082 mol) product of Example 7 in 25 mL anhydrous tetrahydrofuran at −78° C. under nitrogen atmosphere was added 9.5 mL (0.0095 mol) of 1M sodium bis(trimethylsilyl)amide in tetrahydrofuran solution dropwise. Following the addition, the mixture was stirred for 45 min. This was followed by addition of 5.90 g (0.042 mol) methyl iodide in one portion. The mixture was stirred for 1 h and then allowed to warm to room temperature. The resulting mixture was partitioned with sat. ammonium chloride and diethyl ether. The aqueous layer was extracted with ether (2×30 mL), and the combined organic layers were dried (MgSO$_4$) and evaporated. The residue was purified by chromatography (15% ethyl acetate:hexane) to afford 2.22 g (64%) of the desired product as a pale yellow wax; $n_D^{25} = 1.5672$.

EXAMPLE 61

3-Pyridinecarboxylic acid, 5-((dihydro-3-methyl-2(3H)-furanylidene)amino]-2-(iodomethyl)-4-(2-methylpropyl)-6-(trifluoromethyl)-, methyl ester A mixture of 2.63 g (0.0065 mol) product of Example 59 and 2.00 g (0.013 mol) sodium iodide in 25 mL acetone was refluxed for 3 h. The reaction mixture was vacuum filtered through a glass frit, and the filtrate was concentrated. The residue was partitioned with ethyl ether (100 mL) and water (100 mL). The organic layer was washed with brine (2×25 mL), dried (MgSO$_4$), and evaporated. The crude material was purified by chromatography (40% hexane:chloroform) to give 2.74 g (84%) of the desired product as a yellow solid; mp 91°–94° C.

EXAMPLE 62

3-Pyridinecarboxylic acid, 5-[(dihydro-3-methyl-2(3H)-furanylidene)amino]-2-ethenyl-4-(2-methylpropyl)-6-(trifluoromethyl)-, methyl ester This compound was prepared in two steps from product of Example 61 as follows:

Step 1: A stirred mixture of 2.42 g (0.0049 mol) product of Example 61 and 1.38 g (0.0052 mol) triphenylphosphine in 25 mL toluene was refluxed for 1 h. The solvent was evaporated, and the residue solidified when heated under vacuum (0.20 mm). The material was washed with ethyl ether and then vacuum filtered to afford 2.90 g (78%) of the desired phosphonium salt as a pale yellow solid.

Step 2: To a stirred solution of 1.68 g (0.0022 mol) of the above phosphonium salt in 20 mL anhydrous tetrahydrofuran under nitrogen atmosphere was added 0.50 g (0.0033 mol) 1,8-diazabicyclo[5.4.0]undec-7-ene (DBU). The resulting mixture was cooled in an icewater bath. To this mixture was connected a round bottom flask containing 3.22 g (0.106 mol) paraformaldehyde via septa and a double pointed needle with one end in the reaction mixture. The flask containing the paraformaldehyde was warmed with a heat gun until evolution of formaldehyde was observed, and heating was continued an additional 15 min. The reaction mixture was allowed to warm to room temperature and partitioned with 50 mL 10% HCl solution and 50 mL ethyl ether. The organic layer was dried (MgSO$_4$) and evaporated. The crude material was purified by chromatography (10% ethyl acetate:hexane) to give 0.40 g (47%) of the desired product as a yellow wax; $n_D^{25}=1.5844$.

EXAMPLE 63

3-Pyridinecarboxylic acid, 2-(dichloromethyl)-5-[(dihydro-2-(3H)-thienylidene)amino]-4-(2-methylpropyl)-6(trifluoromethyl)-, methyl ester, Was prepared from the product of Example 38 using the procedure in Example 58 in 15.4% yield as a yellow solid: mp=79°-83° C.

EXAMPLE 64

3-Pyridinecarboxylic acid, 2-(difluoromethyl)-5-[(dihydro-3-methyl-2(3H)-thenylidene)amino]-4-(2-methylpropyl)-6-(trifluoromethyl)-, methyl ester Was prepared from the product of Example B-9 using the procedure in Example 37 in 25.2% yield as an oil: $n_D^{25}=1.574$.

PRE-EMERGENCE HERBICIDE EXAMPLES

As noted above, many of the compounds of this invention have been found to be effective as herbicides, particularly pre-emergence herbicides.

The tests for pre-emergence herbicide activity are conducted as follows:

Topsoil is placed in an aluminum pan and compacted to a depth of 0.95 to 1.27 cm. from the top of the pan. On the top of the soil is placed a predetermined number of seeds of each of several monocotyledonous and dicotyledonous annual plant species and/or vegetative propagules of various perennial plant species. The soil required to level fill a pan after seeding or adding vegetative propagules is weighed into another pan. A known amount of the active ingredient dissolved or suspended in an organic solvent or water and applied in acetone or water as a carrier is thoroughly mixed with this cover soil, and the herbicide:soil mixture is used as a cover layer for the previously prepared pan. In Table 1 below the amount of active ingredient applied in the cover layer soil is equal to an application rate of 11.2 kg/ha. After treatment, the pans are moved to a greenhouse bench where they are watered from below as needed to give adequate moisture for germination and growth.

Approximately 10-14 days (usually 11 days) after seeding and treating, the pans are observed and the results (% inhibition) are recorded.

Table 1 below summarizes the results of the pre-emergence herbicidal activity tests of compounds of this invention in weeds. The herbicidal rating shown in Table 1 is the percent inhibition of each plant species, with 100% inhibition being represented by the symbol "C".

HERBICIDE ACTIVITY ON COMMON WEEDS

The plant species usually regarded as weeds which are utilized in one set of tests, the data for which are shown in Table 1, are identified by letter headings above the columns in accordance with the following legend:

Yens - Yellow nutsedge
Anbg - Annual bluegrass
Sejg - Seedling johnsongrass
Dobr - Downy brome
Bygr - Barnyardgrass
Mogl - Morningglory
Cobu - Cocklebur
Vele - Velvetleaf
Inmu - Indian mustard
Wibw - Wild buckwheat

TABLE 1

PRE-EMERGENT ACTIVITY FOR WEEDS

| Ex. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 1 | 11.2100 | 70 | C | C | C | C | 90 | 60 | 90 | C | C |
| 2 | 11.2100 | C | C | C | C | C | C | 90 | C | C | 90 |
| 3 | 11.2100 | 90 | C | C | 90 | C | 90 | 70 | 90 | C | 90 |
| 4 | 11.2100 | 90 | C | C | 90 | C | C | 70 | C | C | 90 |
| 5 | 11.2100 | 90 | C | C | 90 | C | C | 80 | C | C | C |
| 6 | 11.2100 | C | C | C | C | C | C | 30 | C | C | 90 |
| 7 | 11.2100 | C | C | C | C | C | C | 60 | C | C | 90 |
| 8 | 11.2100 | 70 | C | C | 90 | C | C | 60 | 90 | C | C |
| 9 | 11.2100 | 0 | 0 | 90 | 0 | C | 80 | 20 | 80 | 70 | 30 |
| 10 | 11.2100 | 0 | 90 | C | 50 | C | 80 | 20 | 20 | 90 | 30 |
| 11 | 11.2100 | 0 | C | 90 | 20 | C | 80 | 0 | 20 | 80 | 80 |
| 12(E) | 11.2100 | 20 | C | C | 80 | C | 70 | 20 | 80 | C | 70 |
| 13 | 11.2100 | 80 | C | C | 90 | C | 60 | 70 | C | C | 90 |
| 14 | 11.2100 | 40 | C | C | 90 | C | 90 | 10 | 90 | C | 90 |
| 15 | 11.2100 | 90 | C | C | C | C | 90 | 70 | 90 | C | 90 |
| 16(D) | 11.2100 | 90 | C | C | C | C | 90 | 80 | 90 | C | 90 |
| 17 | 11.2100 | 40 | C | C | 90 | C | 80 | 0 | 90 | C | C |
| 18 | 11.2100 | 80 | C | C | C | C | C | 90 | C | C | C |
| 19 | 11.2100 | 90 | C | C | C | C | C | 70 | 80 | C | 90 |
| 20 | 11.2100 | 0 | 0 | 0 | 0 | 0 | 20 | 0 | 10 | 0 | 0 |
| 21 | 11.2100 | 90 | C | C | 90 | C | 80 | 60 | C | C | C |
| 22 | 11.2100 | 0 | C | C | 30 | C | 60 | 10 | 60 | 70 | 40 |
| 23 | 11.2100 | 10 | C | C | 90 | C | 40 | 0 | C | C | 90 |
| 24 | 11.2100 | 80 | C | C | C | C | 90 | 80 | 80 | C | C |
| 25 | 11.2100 | 30 | C | C | 80 | C | 80 | 10 | 90 | C | 90 |
| 26 | 11.2100 | 10 | C | C | 80 | C | 90 | 20 | 80 | C | 90 |

TABLE 1-continued

PRE-EMERGENT ACTIVITY FOR WEEDS

| Ex. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 27 | 11.2100 | 70 | C | C | C | C | 90 | 30 | 80 | C | C |
| 28 | 11.2100 | 0 | 10 | 0 | 0 | 0 | 0 | 0 | 0 | 0 | 0 |
| 29 | 11.2100 | 0 | 0 | 0 | 0 | 0 | 0 | 0 | 0 | 0 | 0 |
| 30 | 11.2100 | 0 | 20 | 20 | 0 | 80 | 20 | 0 | 20 | 70 | 50 |
| 31 | 11.2100 | 0 | 0 | 0 | 0 | 0 | 0 | 0 | 0 | 0 | 0 |
| 32 | 11.2100 | 0 | 70 | 90 | 10 | 80 | 50 | 0 | 0 | 0 | 0 |
|  | 11.2100 | N | N | N | N | N | N | N | N | N | N |
| 33 | 11.2100 | 70 | C | C | C | C | 80 | 10 | 90 | C | 80 |
| 34(E) | 11.2100 | 0 | N | 0 | 0 | 30 | 0 | 0 | 0 | 0 | 0 |
| 35 | 11.2100 | 80 | C | C | C | C | 40 | 0 | 80 | C | C |
| 36 | 11.2100 | 0 | C | 80 | 20 | C | 0 | 0 | 0 | 30 | 0 |
| 37 | 11.2100 | 70 | C | C | 90 | C | 90 | 20 | 90 | C | 90 |
| 38(A) | 11.2100 | 90 | C | C | C | C | 90 | C | 90 | C | 90 |
| 39(B) | 11.2100 | 0 | C | 70 | 0 | C | 60 | 0 | 60 | C | C |
| 40(B) | 11.2100 | 0 | C | C | 80 | C | 90 | 0 | 90 | C | 80 |
| 41(C) | 11.2100 | 90 | C | C | 90 | C | 90 | 40 | C | C | 90 |
| 42(A) | 11.2100 | 40 | C | C | 90 | C | 90 | 70 | 90 | C | 90 |
| 43(A) | 11.2100 | 0 | C | C | 20 | C | 70 | 30 | 90 | C | 70 |
| 44(C) | 11.2100 | 40 | C | 90 | 60 | C | 90 | 0 | 60 | 90 | 40 |
| 45 | 11.2100 | 90 | C | C | 90 | C | 90 | 60 | 90 | C | 90 |
| 46 | 11.2100 | 80 | C | C | C | C | C | 60 | 90 | C | 90 |
| 47 | 11.2100 | 70 | C | C | 60 | C | 80 | 0 | 90 | C | C |
| 48 | 11.2100 | C | C | C | 90 | C | 90 | 0 | 90 | C | 90 |
| 49 | 11.2100 | 70 | C | C | 80 | C | 90 | 10 | 90 | 90 | 80 |
| 50 | 11.2100 | 40 | C | C | 90 | C | 90 | 30 | C | C | 90 |
| 51 | 11.2100 | 90 | C | C | C | C | 80 | 0 | 90 | C | C |
| 52 | 11.2100 | 80 | C | C | 90 | C | 80 | 10 | 80 | C | C |
| 53 | 11.2100 | 50 | C | C | 80 | C | 80 | 0 | 50 | C | 90 |
| 54 | 11.2100 | C | C | C | C | C | C | 50 | 90 | C | C |
| 55 | 11.2100 | 60 | C | 90 | 90 | C | 80 | 50 | C | C | C |
| 56 | 11.2100 | 0 | 0 | 0 | 0 | 0 | 0 | 0 | 0 | 0 | 0 |
| 57 | 11.2100 | 90 | C | C | 90 | C | 90 | 60 | 90 | C | C |
| 58 | 11.2100 | 80 | C | C | 90 | C | 80 | 60 | 80 | C | C |
| 59 | 11.2100 | 30 | 80 | C | 50 | C | 40 | 0 | 40 | C | 30 |
| 60 | 11.2100 | C | C | C | C | C | C | 60 | 90 | C | C |
| 61 | 11.2100 | 0 | C | 90 | 0 | 90 | 40 | 0 | 50 | 80 | 70 |
| 62 | 11.2100 | C | C | C | 90 | C | C | 60 | 70 | C | C |
| 63 | 11.2100 | 80 | C | C | C | C | 80 | 30 | 70 | C | 80 |
| 64 | 11.2100 | 90 | C | C | C | C | 80 | 80 | 80 | C | C |

(A) DAMPING OFF-IMMU AND WIBW; POOR GERMINATION-COBU.
(B) DAMPING OFF-INMU AND WIBW; POOR GERMINATION-WIBW.
(C) DAMPING OFF-INMU AND WIBW.
(D) DAMPING OFF-MOGL, COBU, VELE, INMN, AND WIBW; POOR GERMINATION-WIBW.
(E) SEJG THIN STAND.

POST-EMERGENT HERBICIDE EXAMPLES

The post-emergence herbicidal activity of some of the various compounds of this invention was demonstrated by greenhouse testing in the following manner. Topsoil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a bench in the greenhouse and watered from below as needed. After the plants reach the desired age (two to three weeks), each pan, is removed individually to a spraying chamber and sprayed by means of an atomizer, operating at a spray pressure of 1 70.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 1 0-1 4 days (usually 11 days). In Table 2 the percent inhibition of the plant species is shown, with 100% again being represented by "C", and the following codes are used:

| Species not planted | — |
|---|---|
| Species planted, no data | N |

TABLE 2

POST-EMERGENT ACTIVITY FOR WEEDS

| Ex. No. | Rate kg/ha | Yens | Anbg | Sejg | Dobr | Bygr | Mogl | Cobu | Vele | Inmu | Wibw |
|---|---|---|---|---|---|---|---|---|---|---|---|
| 1 | 11.2100 | 0 | 0 | 0 | 0 | 0 | 30 | 40 | 20 | 60 | 20 |
| 2 | 11.2100 | 50 | 20 | 60 | 30 | 70 | 50 | 60 | 10 | 60 | 60 |
|  | 11.2100 | 70 | 80 | C | 50 | 90 | 60 | 50 | 90 | C | C |

TABLE 2-continued
POST-EMERGENT ACTIVITY FOR WEEDS

| Ex. No. | Rate kg/ha | Yens | Anbg | Sejg | Dobr | Bygr | Mogl | Cobu | Vele | Inmu | Wibw |
|---|---|---|---|---|---|---|---|---|---|---|---|
|  | 11.2100 | 0 | 0 | 30 | 0 | 40 | 30 | 40 | 30 | 20 | 60 |
|  | 1.2100 | 60 | 50 | 80 | 30 | 90 | 50 | 50 | 50 | C | 90 |
|  | 1.2100 | 50 | 20 | 60 | 10 | 50 | 40 | 50 | 10 | 30 | 50 |
| 3 | 11.2100 | 0 | 30 | 50 | 0 | 40 | 40 | 50 | 20 | 30 | 30 |
| 4 | 11.2100 | 0 | 0 | 0 | 0 | 20 | 30 | 30 | 30 | 10 | 20 |
| 5 | 11.2100 | 10 | 20 | 30 | 20 | 30 | 40 | 30 | 30 | 20 | 30 |
| 6 | 11.2100 | 0 | 30 | 40 | 20 | 40 | 40 | 30 | 30 | 30 | 40 |
| 7 | 11.2100 | 0 | 30 | 60 | 30 | 40 | 30 | 30 | 40 | 30 | 30 |
| 8 | 11.2100 | 0 | 10 | 30 | 0 | 30 | 30 | 30 | 50 | 30 | 40 |
| 9 | 11.2100 | 0 | 0 | 0 | 0 | 0 | 0 | 0 | 0 | 0 | 0 |
| 10 | 11.2100 | 0 | 0 | 0 | 0 | 0 | 0 | 0 | 0 | 0 | 0 |
| 11 | 11.2100 | 0 | 0 | 0 | 0 | 0 | 0 | 0 | 0 | 0 | 0 |
| 12 | 11.2100 | 0 | 0 | 40 | 0 | 20 | 50 | 40 | 50 | 40 | 40 |
| 13 | 11.2100 | 0 | 0 | 20 | 0 | 30 | 30 | 30 | 20 | 30 | 30 |
| 14 | 11.2100 | 0 | 20 | 50 | 30 | 60 | 50 | 50 | 40 | 60 | 60 |
| 15 | 11.2100 | 0 | 0 | 50 | 20 | 30 | 20 | 20 | 30 | 10 | 30 |
| 16 | 11.2100 | 0 | 10 | 40 | 20 | 20 | 20 | 30 | 10 | 20 | 10 |
| 17(A) | 11.2100 | 30 | 0 | 30 | 0 | 20 | 40 | 30 | 50 | 40 | 60 |
| 18(B) | 11.2100 | 0 | 0 | 50 | 10 | 70 | 60 | 60 | 60 | N | 60 |
| 19 | 11.2100 | 0 | 10 | 0 | 0 | 10 | 30 | 30 | 10 | 20 | 30 |
| 20 | 11.2100 | 0 | 0 | 0 | 0 | 0 | 0 | 20 | 0 | 30 | 10 |
| 21 | 11.2100 | 0 | 0 | 80 | 20 | 70 | 50 | 40 | 40 | 40 | 50 |
| 22 | 11.2100 | 0 | 0 | 80 | 0 | 0 | 30 | 50 | 30 | 30 | 20 |
| 23 | 11.2100 | 0 | 0 | 60 | 20 | 20 | 30 | 60 | 40 | 40 | 40 |
| 24 | 11.2100 | 0 | 0 | 0 | 0 | 10 | 20 | 0 | 10 | 20 | 20 |
| 25 | 11.2100 | 0 | 10 | 20 | 10 | 30 | 20 | 30 | 20 | 30 | 40 |
| 26 | 11.2100 | 0 | 0 | 0 | 0 | 30 | 20 | 30 | 20 | 20 | 30 |
| 27 | 11.2100 | 0 | 10 | 20 | 0 | 20 | 30 | 30 | 20 | 50 | 60 |
| 28 | 11.2100 | 0 | 0 | 0 | 0 | 0 | 10 | 0 | 0 | 30 | 0 |
| 29 | 11.2100 | 0 | 0 | 0 | 0 | 0 | 0 | 0 | 0 | 0 | 0 |
| 30 | 11.2100 | 0 | 0 | 0 | 0 | 0 | 20 | 10 | 0 | 0 | 0 |
| 31 | 11.2100 | 0 | 0 | 0 | 0 | 0 | 0 | 0 | 0 | 0 | 0 |
| 32 | 11.2100 | 0 | 0 | 0 | 0 | 0 | 0 | 0 | 0 | 0 | 0 |
|  | 11.2100 | N | N | N | N | N | N | N | N | N | N |
| 33 | 11.2100 | 10 | 10 | 80 | 10 | 10 | 40 | 30 | 40 | 40 | 40 |
| 34 | 11.2100 | 0 | 0 | 20 | 10 | 0 | 30 | 30 | 10 | 30 | 20 |
| 35 | 11.2100 | 0 | 0 | 50 | 20 | 60 | 40 | 60 | 40 | 30 | 40 |
| 36 | 11.2100 | 0 | 0 | 50 | 20 | 20 | 30 | 30 | 30 | 30 | 30 |
| 37 | 11.2100 | 0 | 20 | 60 | 30 | 60 | 50 | 50 | 60 | 40 | 60 |
| 38 | 11.2100 | 0 | 0 | 60 | 10 | 60 | 50 | 70 | 60 | 60 | 50 |
| 39 | 11.2100 | 0 | 0 | 0 | 0 | 0 | 0 | 0 | 0 | 0 | 0 |
| 40 | 11.2100 | 0 | 0 | 10 | 0 | 0 | 10 | 10 | 30 | 30 | 20 |
| 41 | 11.2100 | 10 | 0 | 0 | 0 | 10 | 40 | 50 | 40 | 20 | 0 |
| 42 | 11.2100 | 0 | 0 | 60 | 0 | 60 | 50 | 70 | 60 | 50 | 60 |
| 43(C) | 11.2100 | 0 | 0 | 60 | 0 | 10 | 50 | 20 | 50 | 50 | 60 |
| 44 | 11.2100 | 10 | 0 | 10 | 0 | 10 | 50 | 40 | 40 | 10 | 10 |
| 45 | 11.2100 | 0 | 0 | 60 | 10 | 50 | 30 | 60 | 10 | 60 | 20 |
| 46 | 11.2100 | 0 | 0 | 0 | 0 | 0 | 20 | 30 | 30 | 20 | 30 |
| 47 | 11.2100 | 10 | 10 | 20 | 0 | 10 | 20 | 20 | 30 | 10 | 30 |
| 48 | 11.2100 | 0 | 0 | 20 | 0 | 10 | 10 | 10 | 0 | 10 | 10 |
| 49 | 11.2100 | 0 | 0 | 0 | 0 | 0 | 10 | 10 | 0 | 10 | 10 |
| 50 | 11.2100 | 0 | 10 | 70 | 10 | 60 | 50 | 50 | 50 | 50 | 60 |
| 51 | 11.2100 | 0 | 0 | 10 | 30 | 0 | 30 | 40 | 30 | 30 | 30 |
| 52 | 11.2100 | 0 | 0 | 0 | 10 | 10 | 10 | 10 | 10 | 10 | 20 |
| 53 | 11.2100 | 0 | 0 | 0 | 0 | 0 | 30 | 20 | 0 | 0 | 0 |
| 54 | 11.2100 | 0 | 0 | 10 | 0 | 50 | 30 | 30 | 30 | 20 | 30 |
| 55(D) | 11.2100 | 0 | 0 | 50 | 30 | 60 | 30 | 30 | N | 40 | 60 |
| 56 | 11.2100 | 0 | 0 | 0 | 0 | 0 | 0 | 30 | 0 | 40 | 0 |
| 57 | 11.2100 | 0 | 0 | 50 | 10 | 60 | 60 | 50 | 30 | 30 | 30 |
| 58 | 11.2100 | 0 | 0 | 0 | 0 | 0 | 20 | 30 | 20 | 20 | 30 |
| 59 | 11.2100 | 0 | 0 | 0 | 10 | 10 | 20 | 30 | 20 | 20 | 10 |
| 60 | 11.2100 | 0 | 10 | 40 | 0 | 20 | 20 | 30 | 20 | 30 | 30 |
| 61 | 11.2100 | 0 | 0 | 0 | 0 | 0 | 20 | 20 | 20 | 0 | 0 |
| 62 | 11.2100 | 0 | 0 | 30 | 0 | 30 | 40 | 30 | 30 | 30 | 60 |
| 63 | 11.2100 | 0 | 0 | 20 | 0 | 50 | 50 | 40 | 30 | 40 | 20 |
| 64 | 11.2100 | 0 | 0 | 40 | 20 | 60 | 40 | 60 | 30 | 30 | 30 |

(A) Damping off-Vele, Inmu, and Wibw
(B) Damping off-Vele, Inmu,and Wibw; Brittle stems-Mogl.
(C) Damping off- Inmu and Wibw; Poor germination- Cobu.
(D) Test contaminated due to volatile compounds.

The compounds of this invention were further tested for preemergence herbicidal efficacy on weeds in the presence of crop plants using the procedure set out for obtaining the data in Table 1 above but varying the application rate of the test compound. The results of these tests are shown in the following Table 3, in which the data and symbols are as defined for Table 1 and as follows.

| Sobe - | Soybean | Bygr - | Barnyardgrass |
|---|---|---|---|
| Cotz - | Cotton | Lacg - | Large crabgrass |

| | | | | | |
|---|---|---|---|---|---|
| Rape - | Oil seed rape | Grft - | Green Foxtail | Whez - | Wheat |
| Cobu - | Cocklebur | Sube - | Sugar beet | Rice - | Rice |
| Wibw - | Wild buckwheat | Colq - | Common lambsquarter | Grso - | Grain sorghum |
| Mogl - | Morningglory | Pesw - | Pennsylvania smartweed | Corn - | Corn |
| Hese - | Hemp sesbania | Cocw - | Common chickweed | Dobr - | Downy brome |
| Jiwe - | Jimsonweed | Anbg - | Annual bluegrass | Prmi - | Proso millet |
| Vele - | Velvetleaf | Barz - | Barley | | |
| Ruth - | Russian Thistle | | | | |
| Sejg - | Seedling johnsongrass | | | | |
| Wioa - | Wild Oats | | | | |
| Cwba - | Catchweed Bedstraw | | | | |
| Blgr - | Black grass | | | | |

TABLE 3

Herbicide Secondary Preemergence

| Ex. No. | Rate kg/ha | Sobe | Cotz | Rape | Cobu | Wibw | Mogl | Hese | Jiwe | Vele | Whez | Rice | Grso | Corn | Dobr | Prmi |
|---|---|---|---|---|---|---|---|---|---|---|---|---|---|---|---|---|
| 1 | 5.6050 | 90 | 15 | 95 | 15 | C | 75 | 75 | — | 90 | 95 | 90 | C | 95 | C | C |
| | 1.1210 | 70 | 10 | 70 | 0 | 95 | 85 | 80 | — | 90 | 95 | 85 | C | 80 | C | C |
| | 0.2803 | 25 | 15 | 35 | 0 | 70 | 0 | 10 | — | 45 | 55 | 75 | 85 | 25 | 70 | C |
| | 0.0701 | 10 | 25 | 30 | 0 | 25 | 0 | N | — | 35 | 40 | 15 | 30 | 15 | 30 | 0 |
| | 0.0175 | 5 | 0 | 0 | 0 | 20 | N | 0 | — | 0 | 0 | 0 | 0 | 10 | 0 | 0 |
| | 0.0087 | 0 | 0 | 0 | 0 | N | N | 30 | — | N | 0 | 20 | 0 | 0 | 0 | N |
| 2 | 5.6050 | 95 | 80 | 95 | 75 | C | 95 | 95 | — | C | C | C | C | C | C | C |
| | 1.1210 | 90 | 65 | C | 60 | C | 90 | 99 | — | 90 | C | 95 | 99 | 90 | 95 | C |
| | 0.2803 | 75 | 60 | 90 | 25 | C | 85 | 75 | — | 90 | 95 | 90 | C | 85 | C | C |
| | 0.0701 | 65 | 35 | 40 | 0 | 90 | 10 | 55 | — | 65 | 70 | 40 | 90 | 40 | 90 | C |
| | 0.0175 | 20 | 15 | 30 | 0 | 55 | 0 | 0 | — | 10 | 75 | 0 | 55 | 5 | 30 | 40 |
| | 0.0044 | 20 | N | 0 | 0 | 55 | 0 | 0 | — | 35 | 10 | 0 | 0 | 10 | 40 | 45 |
| 3 | 5.6050 | 95 | 45 | C | 40 | C | 90 | 95 | — | 90 | C | 90 | C | 95 | C | C |
| | 1.1210 | 65 | 0 | 70 | 20 | C | 70 | 90 | — | 95 | 95 | 65 | 98 | 90 | 98 | C |
| | 0.2803 | 25 | N | 30 | 0 | 70 | 0 | 60 | — | 55 | 95 | 35 | 95 | 30 | 70 | C |
| | 0.0701 | 10 | 25 | 0 | 0 | 30 | 0 | 10 | — | 35 | 10 | 20 | 35 | 5 | 35 | 40 |
| | 0.0175 | 0 | N | 0 | 0 | 40 | 10 | 30 | — | N | 0 | N | 0 | 5 | 20 | 40 |
| | 0.0087 | 0 | N | 0 | 0 | 20 | 0 | 0 | — | 30 | 0 | N | 0 | 20 | 25 | 0 |
| 4 | 5.6050 | 90 | 60 | 90 | 10 | C | 90 | 90 | — | 90 | C | 95 | C | C | 90 | C |
| | 1.1210 | 85 | 55 | 85 | 0 | C | 0 | 95 | — | 90 | 90 | 95 | 90 | 55 | 85 | C |
| | 0.2803 | 85 | 40 | 75 | N | 90 | N | 75 | — | 55 | 90 | 60 | 90 | 25 | 30 | C |
| | 0.0701 | 20 | 45 | 30 | 0 | 65 | 0 | 95 | — | N | 25 | 45 | 10 | 0 | 10 | 65 |
| | 0.0175 | 25 | N | 35 | 20 | 55 | 40 | 90 | — | 60 | 45 | N | 50 | 35 | 45 | 35 |
| | 0.0087 | 40 | N | 0 | 0 | 0 | 0 | N | — | 10 | 0 | 20 | 0 | 0 | 0 | N |
| 5 | 5.6050 | 95 | 90 | 99 | 75 | C | 90 | C | — | C | C | C | C | 95 | C | C |
| | 1.1210 | C | 80 | C | 40 | C | C | 95 | — | 90 | 95 | 98 | 95 | 90 | 90 | C |
| | 0.2803 | 60 | 55 | 90 | 60 | C | 80 | 90 | — | 75 | 90 | 90 | 85 | 50 | 90 | C |
| | 0.0701 | 80 | 50 | 75 | 35 | 70 | N | 60 | — | 55 | 45 | 0 | 70 | 20 | 30 | C |
| | 0.0175 | 0 | 60 | 30 | 0 | 85 | 0 | 70 | — | 60 | 0 | N | 0 | 20 | 45 | 60 |
| | 0.0087 | N | 35 | 30 | 0 | 45 | 0 | 0 | — | 0 | 20 | N | 30 | N | 30 | 90 |
| 6 | 5.6050 | 95 | 45 | C | 15 | 99 | 85 | 90 | — | 90 | C | 99 | C | C | 99 | C |
| | 1.1210 | 75 | 45 | 60 | 0 | 98 | 55 | 65 | — | 60 | C | 95 | C | 70 | 95 | C |
| | 0.2803 | 80 | 10 | 20 | 0 | 95 | 10 | 20 | — | 20 | 90 | 70 | 65 | 50 | 90 | C |
| | 0.0701 | 15 | 0 | 25 | 0 | 45 | 0 | 60 | — | 0 | 65 | 20 | 50 | 20 | 50 | 65 |
| | 0.0175 | 0 | 0 | 0 | 0 | 20 | 0 | 30 | — | 15 | 30 | 0 | 15 | 25 | 30 | 0 |
| | 0.0087 | 0 | 15 | 0 | 0 | 15 | 0 | 0 | — | 0 | 0 | 5 | 10 | 0 | 25 | 0 |
| 7 | 5.6050 | 95 | 75 | 95 | 15 | C | C | 95 | — | C | C | C | C | 99 | C | C |
| | 1.1210 | 90 | 55 | 85 | 25 | 99 | 95 | 85 | — | 90 | C | 95 | C | 95 | 98 | C |
| | 0.2803 | 85 | 70 | 90 | 0 | 90 | 45 | 70 | — | 85 | 90 | 70 | 99 | 65 | 90 | C |
| | 0.0701 | 75 | 25 | 90 | 0 | 95 | 90 | 65 | — | 55 | 95 | 15 | 95 | 55 | 75 | 85 |
| | 0.0175 | 15 | 10 | 40 | 0 | 55 | 0 | 20 | — | 50 | 60 | 30 | 75 | 10 | 20 | 15 |
| | 0.0087 | 20 | 15 | 10 | 0 | 0 | 0 | 10 | — | 20 | 20 | 20 | 10 | 0 | 0 | 15 |
| 8 | 5.6050 | 90 | 90 | 90 | 25 | C | 90 | C | — | C | 95 | 99 | C | 65 | C | C |
| | 1.1210 | 50 | 90 | 90 | 20 | C | 75 | C | — | 98 | 90 | 99 | 95 | 65 | 90 | C |
| | 0.2803 | 0 | 60 | 30 | 0 | 95 | 15 | 90 | — | 90 | 75 | 90 | 70 | 15 | 90 | 90 |
| | 0.0701 | 10 | N | 10 | 0 | 90 | 25 | N | — | N | 40 | 85 | 30 | 0 | 75 | 90 |
| | 0.0175 | 0 | N | 20 | 0 | 90 | 0 | 85 | — | 90 | 50 | N | 30 | 0 | 80 | 70 |
| | 0.0087 | 0 | N | 0 | 0 | N | 0 | N | — | N | 50 | N | 25 | 0 | 75 | N |
| 9 | 11.2100 | 98 | 0 | — | 0 | — | C | — | — | C | — | C | — | C | — | — |
| | 11.2100 | — | — | C | — | C | — | — | — | — | C | — | — | — | C | — |
| | 5.6050 | 98 | 0 | — | 0 | — | 99 | — | — | 99 | — | C | — | C | — | — |
| | 5.6050 | — | — | C | — | C | — | — | — | — | C | — | — | — | 99 | — |
| | 1.1210 | — | — | 90 | — | 95 | — | — | — | — | 95 | — | — | — | 95 | — |
| | 1.1210 | 75 | 0 | — | 0 | — | 70 | — | — | 70 | — | 80 | — | 60 | — | — |
| | 0.2803 | 0 | 0 | — | 0 | — | 0 | — | — | 25 | — | 25 | — | 10 | — | — |
| | 0.2803 | — | — | 0 | — | 40 | — | — | — | — | 40 | — | — | — | 0 | — |
| 10 | 5.6050 | 95 | 75 | — | 95 | — | 99 | — | — | C | — | C | — | C | — | — |
| | 5.6050 | — | — | C | — | C | — | — | — | — | C | — | — | — | C | — |
| | 1.1210 | — | — | C | — | 90 | — | — | — | — | C | — | — | — | 99 | — |
| | 1.1210 | 30 | 0 | — | 0 | — | 90 | — | — | 95 | — | 75 | — | 95 | — | — |
| | 0.2803 | 0 | 0 | — | 0 | — | 30 | — | — | 75 | — | 20 | — | 60 | — | — |
| | 0.2803 | — | — | 20 | — | 10 | — | — | — | — | 80 | — | — | — | 90 | — |
| | 0.0701 | 0 | 0 | — | 0 | — | — | — | — | 0 | — | 0 | — | 0 | — | — |
| | 0.0701 | — | — | 0 | — | 0 | — | — | — | — | 0 | — | — | — | 0 | — |
| 11 | 5.6050 | 70 | 0 | — | 0 | — | 95 | — | — | 90 | — | 70 | — | 70 | — | — |
| | 5.6050 | — | — | 95 | — | 85 | — | — | — | — | 98 | — | — | — | 85 | — |
| | 1.1210 | 0 | 0 | — | 0 | — | 20 | — | — | 50 | — | 25 | — | 0 | — | — |
| | 1.1210 | — | — | 50 | — | 30 | — | — | — | — | 60 | — | — | — | 30 | — |

TABLE 3-continued

Herbicide Secondary Preemergence

| | | | | | | | | | | | | | | | | | |
|---|---|---|---|---|---|---|---|---|---|---|---|---|---|---|---|---|---|
| | 0.2803 | — | — | 15 | — | 0 | — | — | — | — | 10 | — | — | — | 0 | — |
| | 0.2803 | 0 | 0 | — | 0 | — | 0 | — | — | 0 | — | 0 | — | 0 | — | — |
| | 0.0701 | 0 | 0 | — | 0 | — | 0 | — | — | 0 | — | 0 | — | 0 | — | — |
| | 0.0701 | — | — | 10 | — | 20 | — | — | — | — | 0 | — | — | — | 0 | — |
| 12 | 5.6050 | 80 | 70 | — | 65 | — | C | — | — | 98 | — | 99 | — | 99 | — | — |
| | 5.6050 | — | — | 99 | — | 98 | — | — | — | — | 95 | — | — | — | 85 | — |
| | 1.1210 | 50 | 5 | — | 20 | — | 95 | — | — | 95 | — | 70 | — | 95 | — | — |
| | 1.1210 | — | — | 95 | — | 80 | — | — | — | — | 90 | — | — | — | 70 | — |
| | 0.2803 | — | — | 40 | — | 70 | — | — | — | — | 60 | — | — | — | 80 | — |
| | 0.2803 | 5 | 0 | — | 25 | — | 95 | — | — | 95 | — | 30 | — | 50 | — | — |
| | 0.0701 | 0 | 0 | — | 0 | — | 0 | — | — | 25 | — | 10 | — | 5 | — | — |
| | 0.0701 | — | — | 50 | — | 15 | — | — | — | — | 20 | — | — | — | 15 | — |
| | 0.0175 | 0 | 0 | — | 0 | — | 0 | — | — | 0 | — | 10 | — | 0 | — | — |
| | 0.0175 | — | — | 0 | — | 20 | — | — | — | — | 0 | — | — | — | 0 | — |
| 13 | 5.6050 | 95 | 90 | C | 85 | C | 85 | 98 | — | C | C | C | C | C | C | C |
| | 1.1210 | 95 | 35 | C | 80 | 95 | 40 | 90 | — | 95 | C | 95 | C | 95 | C | C |
| | 0.2803 | 90 | 10 | 90 | 10 | 95 | 0 | 70 | — | 75 | 90 | 85 | C | 95 | 90 | C |
| | 0.0701 | 25 | 0 | 75 | 0 | 40 | 20 | 40 | — | 20 | 90 | 45 | 90 | 80 | 55 | 95 |
| | 0.0175 | 5 | 0 | 0 | 0 | 60 | 0 | 25 | — | 40 | 40 | 15 | 90 | 10 | 55 | 95 |
| | 0.0087 | 35 | 25 | 25 | 0 | 70 | 0 | 0 | — | 0 | 15 | 0 | 80 | 30 | 40 | 80 |
| 14(A) | 5.6050 | 95 | 80 | 98 | 65 | C | 98 | C | — | C | C | C | C | 99 | C | C |
| (A) | 1.1210 | 95 | 70 | 90 | 45 | C | 95 | C | — | C | C | 95 | C | 95 | C | C |
| (A) | 0.2803 | 75 | 65 | 65 | 15 | 95 | C | 75 | — | 70 | 85 | 95 | 95 | 80 | 70 | C |
| (A) | 0.0701 | 35 | 20 | 55 | 0 | 85 | 25 | 55 | — | 30 | 55 | 70 | 80 | 60 | 35 | C |
| (A) | 0.0175 | 25 | 35 | 10 | 0 | 55 | 25 | 0 | — | 0 | 30 | 70 | 40 | 20 | 40 | 85 |
| 15 | 5.6050 | C | 65 | C | 90 | C | C | 99 | C | C | C | C | C | C | C | C |
| | 1.1210 | C | 45 | C | 75 | C | C | 98 | 98 | C | C | C | C | C | C | C |
| | 0.2803 | 95 | 15 | 98 | 55 | C | 90 | 95 | 95 | 95 | C | C | C | 95 | C | C |
| | 0.0701 | 60 | 0 | 90 | 30 | 95 | 65 | 75 | 75 | 75 | 90 | 95 | 95 | 85 | 80 | C |
| | 0.0175 | 0 | 5 | 30 | 0 | 90 | 25 | 40 | 50 | 45 | 40 | 20 | 25 | 25 | 55 | 70 |
| | 0.0087 | 0 | 0 | 0 | 0 | 0 | 0 | 45 | 0 | 0 | 35 | 10 | 0 | 10 | 0 | 95 |
| 16(B) | 5.6050 | C | 95 | C | 75 | C | C | C | — | C | C | C | C | C | C | C |
| (B) | 1.1210 | 95 | 30 | C | 60 | C | 90 | 95 | — | 99 | C | 95 | C | 99 | 99 | C |
| (B) | 0.2803 | 80 | 20 | C | 50 | 80 | 60 | 95 | — | 95 | 95 | 95 | C | 95 | 95 | 99 |
| (B) | 0.0701 | 20 | 5 | 99 | 0 | 95 | 30 | 95 | — | 75 | 50 | 70 | 90 | 50 | 95 | C |
| (B) | 0.0175 | 5 | 0 | 35 | 0 | 70 | 10 | 20 | — | 70 | 10 | 40 | 75 | 10 | 75 | 99 |
| (B) | 0.0087 | 20 | 0 | 50 | 0 | 10 | 0 | 0 | — | 0 | 10 | 10 | 70 | 5 | 25 | 60 |
| 17 | 5.6050 | 25 | 50 | 90 | 0 | 75 | 45 | 90 | — | 90 | 75 | 95 | 95 | 60 | 90 | C |
| | 1.1210 | 30 | 10 | 90 | 0 | 35 | 0 | 55 | — | 60 | 75 | 85 | 90 | 60 | 80 | 90 |
| | 0.2803 | 20 | 0 | 85 | 30 | 35 | 20 | 0 | — | 30 | 10 | 55 | 35 | 0 | 85 | 70 |
| | 0.0701 | 30 | 0 | 10 | 0 | 0 | 0 | 0 | — | 0 | 0 | 0 | 0 | 0 | 0 | 0 |
| | 0.0175 | 30 | 10 | 0 | 0 | 0 | 0 | 0 | — | 0 | 20 | 0 | 0 | 0 | 0 | 0 |
| 18 | 5.6050 | 95 | 55 | C | 70 | C | 95 | 95 | — | 95 | C | C | C | 95 | C | C |
| | 1.1210 | 90 | 20 | 95 | 40 | 90 | 75 | 70 | — | 85 | 95 | 95 | C | 95 | 90 | C |
| | 0.2803 | 25 | 10 | 90 | 0 | 95 | 45 | 65 | — | 70 | 75 | 85 | 90 | 20 | 80 | 95 |
| | 0.0701 | 10 | 0 | 20 | 0 | 10 | 0 | 0 | — | 10 | 15 | 0 | 30 | 0 | 35 | 40 |
| | 0.0175 | 0 | 30 | 20 | 30 | 0 | 0 | 15 | — | 10 | 35 | 10 | 0 | 10 | 0 | 0 |
| | 0.0087 | 0 | 0 | 0 | 0 | 0 | 0 | 0 | — | 0 | 0 | 0 | 0 | 0 | 0 | 0 |
| 19 | 5.6050 | 95 | 45 | C | 35 | C | C | C | — | C | C | C | C | C | 98 | C |
| | 1.1210 | 80 | 55 | 65 | 0 | 95 | 30 | 95 | — | 90 | 85 | 90 | 90 | 35 | 70 | C |
| | 0.2803 | 90 | N | 40 | 0 | 90 | 85 | 25 | — | 35 | 55 | 35 | 65 | 35 | 60 | C |
| | 0.0701 | 20 | N | N | N | 90 | 40 | N | — | 60 | 35 | 60 | 30 | 0 | 70 | 70 |
| | 0.0175 | N | 25 | 0 | 0 | 80 | 0 | 0 | — | 20 | 0 | 10 | 15 | 40 | 0 | 0 |
| | 0.0087 | 0 | 60 | 0 | 0 | 60 | 0 | 30 | — | 25 | 25 | 45 | 0 | 20 | 25 | 0 |
| 21 | 5.6050 | — | — | C | — | C | — | — | — | — | C | — | — | — | C | — |
| | 5.6050 | 99 | 80 | — | 50 | — | 99 | — | — | 99 | — | C | — | 99 | — | — |
| | 1.1210 | 95 | 70 | — | 25 | — | 95 | — | — | C | — | C | — | 95 | — | — |
| | 1.1210 | — | — | C | — | C | — | — | — | — | C | — | — | — | C | — |
| | 0.2803 | 80 | 5 | — | 0 | — | 50 | — | — | 98 | — | 80 | — | 50 | — | — |
| | 0.2803 | — | — | C | — | C | — | — | — | — | 98 | — | — | — | 98 | — |
| | 0.0701 | 25 | 0 | — | 0 | — | 25 | — | — | 30 | — | 50 | — | 25 | — | — |
| | 0.0701 | — | — | 99 | — | 75 | — | — | — | — | 50 | — | — | — | 75 | — |
| | 0.0175 | 20 | 0 | — | 0 | — | 0 | — | — | 0 | — | 25 | — | 25 | — | — |
| | 0.0175 | — | — | 65 | — | 25 | — | — | — | — | 0 | — | — | — | 25 | — |
| | 0.0044 | 0 | 0 | — | 0 | — | 0 | — | — | 0 | — | 0 | — | 0 | — | — |
| | 0.0044 | — | — | 0 | — | 0 | — | — | — | — | 0 | — | — | — | 0 | — |
| 22 | 5.6050 | 75 | 20 | — | 0 | — | 40 | — | — | 90 | — | 95 | — | 65 | — | — |
| | 5.6050 | — | — | C | — | 80 | — | — | — | — | 99 | — | — | — | 80 | — |
| | 1.1210 | 10 | 0 | — | 0 | — | 0 | — | — | 20 | — | 20 | — | 10 | — | — |
| | 1.1210 | — | — | 70 | — | 60 | — | — | — | — | 40 | — | — | — | 70 | — |
| | 0.2803 | — | — | 0 | — | 0 | — | — | — | — | 0 | — | — | — | 0 | — |
| | 0.2803 | 0 | 0 | — | 0 | — | 0 | — | — | 0 | — | 20 | — | 0 | — | — |
| | 0.0701 | — | — | 0 | — | 0 | — | — | — | — | 0 | — | — | — | 0 | — |
| | 0.0701 | 0 | 0 | — | 0 | — | 0 | — | — | 0 | — | 0 | — | 0 | — | — |
| 23 | 5.6050 | 99 | 20 | — | 0 | — | 90 | — | — | C | — | C | — | C | — | — |
| | 5.6050 | — | — | C | — | C | — | — | — | — | C | — | — | — | C | — |
| | 1.1210 | — | — | C | — | 99 | — | — | — | — | 99 | — | — | — | 99 | — |
| | 1.1210 | 70 | 20 | — | 0 | — | 40 | — | — | 75 | — | C | — | 90 | — | — |
| | 0.2803 | 25 | 0 | — | 0 | — | 0 | — | — | 50 | — | 80 | — | 35 | — | — |
| | 0.2803 | — | — | 70 | — | 60 | — | — | — | — | 95 | — | — | — | 75 | — |
| | 0.0701 | 0 | 0 | — | 0 | — | N | — | — | 0 | — | 10 | — | 20 | — | — |

TABLE 3-continued

Herbicide Secondary Preemergence

|    | Rate    |    |    |    |    |    |    |    |    |    |    |    |    |    |    |    |
|----|---------|----|----|----|----|----|----|----|----|----|----|----|----|----|----|----|
|    | 0.0701  | —  | —  | 0  | —  | 0  | —  | —  | —  | —  | 0  | —  | —  | —  | 0  | —  |
|    | 0.0175  | 0  | 0  | —  | 0  | —  | 0  | —  | —  | 0  | —  | 30 | —  | 0  | —  | —  |
|    | 0.0175  | —  | —  | 0  | —  | 0  | —  | —  | —  | —  | 0  | —  | —  | —  | 0  | —  |
| 24 | 5.6050  | —  | —  | C  | —  | C  | —  | —  | —  | —  | C  | —  | —  | —  | C  | —  |
|    | 5.6050  | 95 | 90 | —  | 60 | —  | 99 | —  | —  | 99 | —  | C  | —  | C  | —  | —  |
|    | 1.1210  | 90 | 25 | —  | 25 | —  | 95 | —  | —  | 95 | —  | C  | —  | 99 | —  | —  |
|    | 1.1210  | —  | —  | C  | —  | C  | —  | —  | —  | —  | C  | —  | —  | —  | 98 | —  |
|    | 0.2803  | 85 | 0  | —  | 0  | —  | 70 | —  | —  | 85 | —  | C  | —  | 90 | —  | —  |
|    | 0.2803  | —  | —  | 90 | —  | 99 | —  | —  | —  | —  | 90 | —  | —  | —  | 90 | —  |
|    | 0.0701  | 45 | 0  | —  | 15 | —  | 75 | —  | —  | 60 | —  | 98 | —  | 85 | —  | —  |
|    | 0.0701  | —  | —  | 0  | —  | 80 | —  | —  | —  | —  | 25 | —  | —  | —  | 70 | —  |
|    | 0.0175  | 0  | 0  | —  | 0  | —  | 0  | —  | —  | 0  | —  | 15 | —  | 0  | —  | —  |
|    | 0.0175  | —  | —  | 0  | —  | 10 | —  | —  | —  | —  | 0  | —  | —  | —  | 10 | —  |
|    | 0.0044  | 0  | 0  | —  | 0  | —  | 0  | —  | —  | 0  | —  | 0  | —  | 0  | —  | —  |
|    | 0.0044  | —  | —  | 0  | —  | 0  | —  | —  | —  | —  | 0  | —  | —  | —  | 0  | —  |
| 25 | 5.6050  | —  | —  | C  | —  | 99 | —  | —  | —  | —  | C  | —  | —  | —  | 95 | —  |
|    | 5.6050  | 90 | 20 | —  | 20 | —  | C  | —  | —  | 95 | —  | C  | —  | C  | —  | —  |
|    | 1.1210  | 75 | 20 | —  | 0  | —  | C  | —  | —  | 75 | —  | C  | —  | 99 | —  | —  |
|    | 1.1210  | —  | —  | 98 | —  | 90 | —  | —  | —  | —  | 90 | —  | —  | —  | 60 | —  |
|    | 0.2803  | 5  | 0  | —  | 0  | —  | 60 | —  | —  | 25 | —  | 50 | —  | 25 | —  | —  |
|    | 0.2803  | —  | —  | 30 | —  | 60 | —  | —  | —  | —  | 10 | —  | —  | —  | 60 | —  |
|    | 0.0701  | 0  | 10 | —  | 0  | —  | 20 | —  | —  | 0  | —  | 0  | —  | 10 | —  | —  |
|    | 0.0701  | —  | —  | 60 | —  | 15 | —  | —  | —  | —  | 0  | —  | —  | —  | 0  | —  |
|    | 0.0175  | 0  | 0  | —  | 0  | —  | 0  | —  | —  | 0  | —  | 10 | —  | 25 | —  | —  |
|    | 0.0175  | —  | —  | 10 | —  | 15 | —  | —  | —  | —  | 0  | —  | —  | —  | 0  | —  |
| 26 | 5.6050  | —  | —  | 99 | —  | C  | —  | —  | —  | —  | C  | —  | —  | —  | 98 | —  |
|    | 5.6050  | 90 | 25 | —  | 0  | —  | 98 | —  | —  | 90 | —  | C  | —  | 98 | —  | —  |
|    | 1.1210  | 80 | 10 | —  | 0  | —  | 90 | —  | —  | 95 | —  | 99 | —  | 99 | —  | —  |
|    | 1.1210  | —  | —  | 90 | —  | 70 | —  | —  | —  | —  | 80 | —  | —  | —  | 70 | —  |
|    | 0.2803  | 10 | N  | —  | 0  | —  | N  | —  | —  | 50 | —  | 60 | —  | 25 | —  | —  |
|    | 0.2803  | —  | —  | 50 | —  | 20 | —  | —  | —  | —  | 10 | —  | —  | —  | 10 | —  |
|    | 0.0701  | 0  | 0  | —  | 0  | —  | 0  | —  | —  | 0  | —  | 0  | —  | 0  | —  | —  |
|    | 0.0701  | —  | —  | 45 | —  | 70 | —  | —  | —  | —  | 10 | —  | —  | —  | 30 | —  |
|    | 0.0175  | 0  | 0  | —  | 0  | —  | 0  | —  | —  | 0  | —  | 0  | —  | 0  | —  | —  |
|    | 0.0175  | —  | —  | 15 | —  | 10 | —  | —  | —  | —  | 0  | —  | —  | —  | 0  | —  |
| 27 | 5.6050  | —  | —  | C  | —  | C  | —  | —  | —  | —  | C  | —  | —  | —  | 99 | —  |
|    | 5.6050  | 95 | 50 | —  | 50 | —  | 95 | —  | —  | 95 | —  | C  | —  | 98 | —  | —  |
|    | 1.1210  | 75 | 20 | —  | 0  | —  | 90 | —  | —  | 90 | —  | 99 | —  | 80 | —  | —  |
|    | 1.1210  | —  | —  | 98 | —  | C  | —  | —  | —  | —  | C  | —  | —  | —  | 95 | —  |
|    | 0.2803  | 30 | 0  | —  | 0  | —  | 50 | —  | —  | 50 | —  | 60 | —  | 35 | —  | —  |
|    | 0.2803  | —  | —  | 98 | —  | 80 | —  | —  | —  | —  | 80 | —  | —  | —  | 60 | —  |
|    | 0.0701  | —  | —  | 85 | —  | 70 | —  | —  | —  | —  | 40 | —  | —  | —  | 50 | —  |
|    | 0.0701  | 5  | 0  | —  | 0  | —  | 50 | —  | —  | 0  | —  | 10 | —  | 5  | —  | —  |
|    | 0.0175  | 0  | 0  | —  | 0  | —  | 50 | —  | —  | 0  | —  | 0  | —  | 0  | —  | —  |
|    | 0.0175  | —  | —  | 10 | —  | 0  | —  | —  | —  | —  | 10 | —  | —  | —  | 0  | —  |
|    | 0.0044  | 0  | 0  | —  | 0  | —  | 0  | —  | —  | 0  | —  | 0  | —  | 0  | —  | —  |
|    | 0.0044  | —  | —  | 0  | —  | 0  | —  | —  | —  | —  | 0  | —  | —  | —  | 0  | —  |
| 30 | 11.2100 | 0  | 0  | —  | 0  | —  | 0  | —  | —  | 30 | —  | 25 | —  | 20 | —  | —  |
|    | 11.2100 | —  | —  | 98 | —  | 55 | —  | —  | —  | —  | 20 | —  | —  | —  | 20 | —  |
|    | 5.6050  | —  | —  | 50 | —  | 30 | —  | —  | —  | —  | 30 | —  | —  | —  | 15 | —  |
|    | 5.6050  | 0  | 0  | —  | 0  | —  | 0  | —  | —  | 0  | —  | 0  | —  | 0  | —  | —  |
|    | 1.1210  | 0  | 0  | —  | 0  | —  | 0  | —  | —  | 0  | —  | 0  | —  | 0  | —  | —  |
|    | 1.1210  | —  | —  | 25 | —  | 15 | —  | —  | —  | —  | 10 | —  | —  | —  | 0  | —  |
| 32 | 5.6050  | 0  | 0  | —  | 0  | —  | 0  | —  | —  | 0  | —  | 25 | —  | 25 | —  | —  |
|    | 5.6050  | —  | —  | 50 | —  | 10 | —  | —  | —  | —  | 20 | —  | —  | —  | 40 | —  |
|    | 1.1210  | 0  | 0  | —  | 25 | —  | 40 | —  | —  | 60 | —  | 10 | —  | 0  | —  | —  |
|    | 1.1210  | —  | —  | 0  | —  | 15 | —  | —  | —  | —  | 0  | —  | —  | —  | 0  | —  |
|    | 0.2803  | —  | —  | 0  | —  | 30 | —  | —  | —  | —  | 0  | —  | —  | —  | 0  | —  |
|    | 0.2803  | 0  | 0  | —  | 0  | —  | 50 | —  | —  | 25 | —  | 25 | —  | 0  | —  | —  |
| 33 | 5.6050  | C  | 98 | —  | 60 | —  | C  | —  | —  | C  | —  | C  | —  | C  | —  | —  |
|    | 5.6050  | —  | —  | C  | —  | C  | —  | —  | —  | —  | C  | —  | —  | —  | C  | —  |
|    | 1.1210  | 75 | 0  | —  | 0  | —  | 60 | —  | —  | 80 | —  | 95 | —  | 75 | —  | —  |
|    | 1.1210  | —  | —  | C  | —  | C  | —  | —  | —  | —  | 99 | —  | —  | —  | 98 | —  |
|    | 0.2803  | 35 | 0  | —  | 0  | —  | 40 | —  | —  | 99 | —  | 70 | —  | 35 | —  | —  |
|    | 0.2803  | —  | —  | C  | —  | 30 | —  | —  | —  | —  | C  | —  | —  | —  | 80 | —  |
|    | 0.0701  | 0  | 0  | —  | 0  | —  | 0  | —  | —  | 0  | —  | 0  | —  | 0  | —  | —  |
|    | 0.0701  | —  | —  | 15 | —  | 10 | —  | —  | —  | —  | 10 | —  | —  | —  | 10 | —  |
|    | 0.0175  | 0  | 0  | —  | 0  | —  | 0  | —  | —  | 0  | —  | 0  | —  | 0  | —  | —  |
|    | 0.0175  | —  | —  | 0  | —  | N  | —  | —  | —  | —  | 0  | —  | —  | —  | 0  | —  |
|    | 0.0044  | 0  | 0  | —  | 0  | —  | 0  | —  | —  | 0  | —  | 0  | —  | 0  | —  | —  |
|    | 0.0044  | —  | —  | 0  | —  | 0  | —  | —  | —  | —  | 0  | —  | —  | —  | 0  | —  |
| 35 | 5.6050  | —  | —  | C  | —  | C  | —  | —  | —  | —  | C  | —  | —  | —  | C  | —  |
|    | 5.6050  | 98 | 30 | —  | 0  | —  | 95 | —  | —  | C  | —  | C  | —  | C  | —  | —  |
|    | 1.1210  | 75 | 5  | —  | 0  | —  | 80 | —  | —  | 98 | —  | C  | —  | 99 | —  | —  |
|    | 1.1210  | —  | —  | C  | —  | C  | —  | —  | —  | —  | C  | —  | —  | —  | C  | —  |
|    | 0.2803  | 5  | 0  | —  | 0  | —  | 0  | —  | —  | 90 | —  | 95 | —  | 70 | —  | —  |
|    | 0.2803  | —  | —  | C  | —  | C  | —  | —  | —  | —  | C  | —  | —  | —  | C  | —  |
|    | 0.0701  | 0  | 0  | —  | 0  | —  | 0  | —  | —  | 0  | —  | 20 | —  | 10 | —  | —  |
|    | 0.0701  | —  | —  | 35 | —  | 30 | —  | —  | —  | —  | 20 | —  | —  | —  | 50 | —  |
|    | 0.0175  | 0  | 0  | —  | 0  | —  | 0  | —  | —  | 0  | —  | 0  | —  | 0  | —  | —  |
|    | 0.0175  | —  | —  | 0  | —  | 0  | —  | —  | —  | —  | 0  | —  | —  | —  | 0  | —  |

TABLE 3-continued

Herbicide Secondary Preemergence

| | | | | | | | | | | | | | | | | | |
|---|---|---|---|---|---|---|---|---|---|---|---|---|---|---|---|---|---|
| | 0.0044 | — | — | 0 | — | 0 | — | — | — | — | 0 | — | — | — | 0 | — | — |
| | 0.0044 | 0 | 0 | — | 0 | — | 0 | — | — | 0 | — | 0 | — | 0 | — | — | — |
| 36 | 5.6050 | — | — | 99 | — | 25 | — | — | — | — | 60 | — | — | — | 30 | — | — |
| | 5.6050 | 25 | 0 | — | 0 | — | 80 | — | — | 0 | — | 35 | — | 80 | — | — | — |
| | 1.1210 | 0 | 0 | — | 0 | — | 30 | — | — | 0 | — | 20 | — | 5 | — | — | — |
| | 1.1210 | — | — | 65 | — | 0 | — | — | — | — | 0 | — | — | — | 0 | — | — |
| | 0.2803 | 0 | 0 | — | 0 | — | 0 | — | — | 0 | — | 0 | — | 0 | — | — | — |
| | 0.2803 | — | — | 10 | — | 0 | — | — | — | — | 0 | — | — | — | 0 | — | — |
| | 0.0701 | 0 | 0 | — | 0 | — | 0 | — | — | 0 | — | 10 | — | 5 | — | — | — |
| | 0.0701 | — | — | 0 | — | 0 | — | — | — | — | 0 | — | — | — | 0 | — | — |
| 37(A) | 5.6050 | 85 | 35 | 90 | 45 | 95 | 80 | 90 | — | 75 | 95 | 95 | C | 90 | 95 | C |
| (A) | 1.1210 | 45 | N | 75 | 0 | 95 | 75 | 75 | — | 65 | 90 | 90 | 95 | 60 | 75 | C |
| (A) | 0.2803 | 20 | 55 | 30 | 20 | 35 | 35 | 65 | — | 35 | 60 | 65 | 60 | 30 | 0 | 85 |
| (A) | 0.0701 | 0 | 0 | 0 | 0 | 35 | 0 | 15 | — | 40 | 25 | 35 | 40 | 30 | 40 | 60 |
| (A) | 0.0175 | 35 | N | 20 | 0 | 25 | N | N | — | 0 | 35 | N | N | 25 | 0 | 25 |
| (A) | 0.0087 | N | 30 | 30 | 30 | 0 | N | 20 | — | 0 | 40 | 10 | N | 10 | 0 | 0 |
| 38(D) | 5.6050 | 95 | 85 | 95 | N | 95 | 95 | 95 | 95 | 95 | C | C | C | 95 | C | C |
| (D) | 1.1210 | 95 | 50 | 95 | N | 90 | 95 | 95 | 90 | C | 95 | C | C | C | C | C |
| (D) | 0.2803 | 60 | 10 | 90 | N | 75 | 65 | 90 | 70 | 95 | 95 | 95 | 99 | 95 | 90 | C |
| (D) | 0.0701 | 0 | 10 | 90 | N | 0 | 0 | 0 | 20 | 0 | 85 | 55 | 95 | 45 | 45 | 95 |
| (D) | 0.0175 | 0 | 10 | 0 | N | 0 | 0 | 0 | 0 | 0 | 55 | 40 | 45 | 10 | 85 | 90 |
| (D) | 0.0087 | 0 | 0 | 0 | N | 0 | 0 | 0 | 0 | 0 | 0 | 0 | 50 | 10 | 0 | 0 |
| 39 | 5.6050 | 80 | 30 | 95 | 0 | 95 | 75 | 80 | 95 | 95 | 95 | C | 95 | 90 | 90 | C |
| | 1.1210 | 70 | 5 | 90 | 0 | 95 | 80 | 80 | 85 | 85 | 85 | 95 | 95 | 90 | 85 | C |
| | 0.2803 | 0 | 10 | 0 | 0 | 0 | 0 | 20 | 20 | 75 | 20 | 40 | 0 | 25 | 35 | 0 |
| | 0.0701 | 0 | 0 | 0 | 0 | 0 | 0 | 0 | 0 | 0 | 0 | 15 | 0 | 0 | 0 | N |
| 40 | 5.6050 | 95 | 50 | 95 | 15 | 95 | 95 | 90 | 90 | 90 | C | C | C | 95 | C | C |
| | 1.1210 | 90 | 45 | 90 | 15 | 90 | 95 | 80 | 60 | 90 | 95 | 99 | 95 | 90 | 95 | C |
| | 0.2803 | 15 | 20 | 60 | 20 | 20 | 75 | 45 | 30 | 30 | 55 | 90 | 35 | 10 | 50 | C |
| | 0.0701 | 0 | 0 | 0 | 0 | 0 | 0 | 0 | 0 | N | 30 | 0 | 10 | 25 | 40 | 90 |
| 41 | 5.6050 | 90 | 85 | C | 50 | C | 95 | 95 | C | C | C | C | C | C | C | C |
| | 1.1210 | 90 | 30 | C | 10 | 60 | 95 | 75 | 85 | 90 | 90 | 40 | C | 95 | C | C |
| | 0.2803 | 25 | 15 | 40 | 35 | 10 | 35 | 35 | 85 | 60 | 60 | 50 | 35 | 40 | 75 | 95 |
| | 0.0701 | 40 | 15 | 30 | 20 | 20 | 55 | 20 | 55 | 0 | 0 | 20 | 20 | 30 | 80 | 90 |
| | 0.0175 | N | 0 | 0 | 0 | 0 | 0 | 0 | 30 | 0 | 20 | 0 | 10 | 0 | 0 | 0 |
| | 0.0087 | 0 | 0 | 0 | 0 | 0 | 0 | 0 | 0 | 0 | 0 | 0 | 0 | 0 | 0 | 0 |
| 42(D) | 5.6050 | 95 | 75 | 95 | N | C | C | 95 | 85 | 90 | C | C | C | C | 95 | C |
| (D) | 1.1210 | 95 | 20 | 90 | N | 90 | 95 | 95 | 85 | 95 | 95 | C | C | 95 | 95 | C |
| (D) | 0.2803 | 80 | 45 | 75 | N | 35 | 95 | 80 | 60 | 85 | 95 | 95 | C | 95 | 80 | C |
| (D) | 0.0701 | 0 | 15 | 0 | N | 0 | 0 | 0 | 0 | 0 | 35 | 45 | 25 | 0 | 0 | 75 |
| (D) | 0.0175 | 5 | 0 | 0 | N | 0 | 0 | 0 | 0 | 0 | 0 | 0 | 0 | 0 | 0 | 0 |
| (D) | 0.0087 | 0 | 15 | 0 | N | 0 | 0 | 0 | 0 | 0 | 0 | N | 0 | 0 | 0 | 0 |
| 43(C) | 5.6050 | 55 | 20 | 80 | 50 | 60 | 75 | 55 | 40 | 40 | 35 | 95 | 95 | 85 | 98 | 95 |
| (C) | 1.1210 | 55 | N | 70 | 1 | 10 | 75 | 0 | 10 | 0 | 15 | 40 | 75 | 90 | 0 | 20 |
| (C) | 0.2803 | 20 | 0 | 0 | 0 | N | 0 | 0 | N | 0 | 0 | 20 | 0 | 0 | 0 | 0 |
| (C) | 0.0701 | 0 | 0 | 0 | 0 | 0 | 0 | 0 | 0 | 0 | 0 | 0 | 0 | 0 | 0 | 0 |
| 44 | 5.6050 | 95 | 80 | 98 | 30 | C | 90 | 95 | C | 90 | 85 | 90 | C | 90 | 95 | C |
| | 1.1210 | 25 | 35 | 90 | 0 | 60 | 50 | 30 | 90 | 30 | 45 | 85 | 85 | 50 | 70 | 85 |
| | 0.2803 | 25 | 10 | 60 | 0 | 30 | 0 | 30 | 65 | 0 | 40 | 25 | 35 | 0 | 35 | 50 |
| | 0.0701 | 40 | 35 | 0 | 0 | 0 | 0 | 15 | 55 | 0 | 0 | 0 | 0 | 0 | 0 | 0 |
| 45 | 5.6050 | 80 | 90 | — | 60 | — | 95 | — | — | 99 | — | 99 | — | 99 | — | — |
| | 5.6050 | — | — | 99 | — | 99 | — | — | — | — | C | — | — | — | 98 | — |
| | 1.1210 | — | — | 95 | — | C | — | — | — | — | 99 | — | — | — | 95 | — |
| | 1.1210 | 75 | 60 | — | 30 | — | 95 | — | — | 95 | — | 99 | — | 95 | — | — |
| | 0.2803 | 20 | 5 | — | 0 | — | 90 | — | — | 90 | — | 70 | — | 25 | — | — |
| | 0.2803 | — | — | 95 | — | 90 | — | — | — | — | 98 | — | — | — | 85 | — |
| | 0.0701 | 10 | 0 | — | 0 | — | 40 | — | — | 60 | — | 10 | — | 10 | — | — |
| | 0.0701 | — | — | 85 | — | 85 | — | — | — | — | 60 | — | — | — | 60 | — |
| | 0.0175 | 0 | 0 | — | 0 | — | 0 | — | — | 0 | — | 10 | — | 20 | — | — |
| | 0.0175 | — | — | 60 | — | 10 | — | — | — | — | 20 | — | — | — | 30 | — |
| | 0.0044 | 0 | 0 | — | 0 | — | 0 | — | — | 0 | — | 0 | — | 0 | — | — |
| | 0.0044 | — | — | 0 | — | 10 | — | — | — | — | 0 | — | — | — | 0 | — |
| 46 | 5.6050 | 95 | 60 | 95 | 40 | C | 90 | 90 | — | 90 | C | C | C | 95 | C | C |
| | 1.1210 | 90 | 15 | 90 | 15 | 90 | 95 | 75 | — | 85 | C | 95 | C | 95 | 98 | C |
| | 0.2803 | 85 | 5 | N | 10 | 60 | 50 | 55 | — | 60 | 90 | 85 | 85 | 55 | 90 | C |
| | 0.0701 | 0 | 0 | 25 | 25 | 0 | 10 | 0 | — | 10 | 15 | 25 | 55 | 0 | 50 | 95 |
| | 0.0175 | 10 | 0 | 20 | 0 | 0 | 0 | 20 | — | 0 | 20 | 15 | 10 | 0 | 0 | 10 |
| | 0.0087 | 0 | 0 | 0 | 0 | 0 | 0 | 10 | — | 0 | 0 | 0 | 15 | 0 | 0 | 0 |
| 47(E) | 5.6050 | C | 90 | C | 30 | C | C | C | — | C | C | C | C | C | C | C |
| (E) | 1.1210 | 95 | 35 | 95 | 0 | C | C | 95 | — | C | 99 | 95 | C | 90 | 80 | C |
| (E) | 0.2803 | 15 | 45 | 55 | 0 | C | 0 | 50 | — | 35 | 70 | 95 | 75 | 45 | 60 | 95 |
| (E) | 0.0701 | 15 | 45 | 10 | 0 | 75 | 0 | N | — | N | 25 | 70 | 0 | 35 | 30 | 80 |
| (E) | 0.0175 | 15 | 0 | 30 | 0 | 0 | 0 | 0 | — | 0 | 35 | 40 | 0 | 0 | 0 | 10 |
| 48 | 5.6050 | 95 | 60 | 90 | 0 | C | 95 | 95 | — | 90 | 75 | C | C | C | 95 | C |
| | 1.1210 | 65 | 15 | 45 | 0 | C | 50 | 75 | — | 75 | 65 | C | 90 | 30 | 90 | C |
| | 0.2803 | 10 | N | 0 | 0 | 75 | 0 | 35 | — | 45 | 55 | 70 | 65 | 10 | 40 | 95 |
| | 0.0701 | 0 | 10 | 0 | 0 | 45 | 0 | N | — | 40 | 20 | 65 | 0 | 25 | 50 | 75 |
| | 0.0175 | N | N | 0 | 0 | 50 | 30 | N | — | N | 45 | N | 10 | 25 | 30 | 70 |
| | 0.0087 | 0 | 40 | 0 | 0 | 55 | 0 | N | — | N | 0 | 20 | 0 | 5 | 0 | 35 |
| 49 | 5.6050 | 70 | 45 | 90 | 0 | 95 | 60 | 75 | — | 40 | 90 | 65 | 95 | 40 | 80 | C |
| | 1.1210 | 25 | N | 65 | 0 | 90 | 15 | 75 | — | 60 | 45 | 45 | 55 | 10 | 75 | C |

TABLE 3-continued

Herbicide Secondary Preemergence

|  |  |  |  |  |  |  |  |  |  |  |  |  |  |  |  |  |
|---|---|---|---|---|---|---|---|---|---|---|---|---|---|---|---|---|
|  | 0.2803 | 15 | N | 10 | 0 | 70 | 0 | N | — | N | 35 | 40 | 35 | 10 | 45 | 55 |
|  | 0.0701 | 0 | 10 | 0 | 0 | 90 | 0 | 0 | — | 0 | 0 | 45 | 0 | 0 | 55 | 70 |
|  | 0.0175 | 0 | N | 0 | 0 | 70 | 0 | N | — | N | 0 | N | 0 | 0 | 30 | 10 |
|  | 0.0087 | 0 | N | 0 | 0 | 0 | 0 | N | — | 25 | 0 | N | 0 | 0 | 0 | 0 |
| 50 | 5.6050 | 95 | 85 | 95 | 75 | C | C | 95 | — | 90 | C | C | C | C | C | C |
|  | 1.1210 | 65 | 50 | 75 | 75 | 90 | 65 | 75 | — | 90 | 90 | 98 | C | 90 | C | C |
|  | 0.2803 | 40 | 65 | 50 | 0 | 90 | 0 | 75 | — | 70 | 90 | 80 | 98 | 75 | 75 | C |
|  | 0.0701 | 35 | 25 | 0 | 0 | 55 | 0 | 50 | — | 0 | 50 | 70 | 70 | 15 | 45 | 80 |
|  | 0.0175 | 0 | 0 | 10 | 0 | 45 | 0 | 0 | — | 0 | 0 | 15 | 40 | 5 | 0 | 0 |
| 51 | 5.6050 | 95 | 95 | — | 75 | — | 99 | — | — | 98 | — | C | — | C | — | — |
|  | 5.6050 | — | — | 99 | — | C | — | — | — | — | C | — | — | — | C | — |
|  | 1.1210 | 50 | 75 | — | 35 | — | 80 | — | — | 95 | — | 80 | — | 99 | — | — |
|  | 1.1210 | — | — | 95 | — | C | — | — | — | — | 95 | — | — | — | 90 | — |
|  | 0.2803 | — | — | 85 | — | 98 | — | — | — | — | 90 | — | — | — | 90 | — |
|  | 0.2803 | 5 | 0 | — | 0 | — | 30 | — | — | 40 | — | 40 | — | 40 | — | — |
|  | 0.0701 | 0 | 0 | — | 0 | — | 0 | — | — | 20 | — | 20 | — | 0 | — | — |
|  | 0.0701 | — | — | 20 | — | 60 | — | — | — | — | 35 | — | — | — | 70 | — |
|  | 0.0175 | 0 | 0 | — | 0 | — | 0 | — | — | 0 | — | 10 | — | 0 | — | — |
|  | 0.0175 | — | — | 10 | — | 15 | — | — | — | — | 15 | — | — | — | 20 | — |
|  | 0.0044 | — | — | 0 | — | 10 | — | — | — | — | 5 | — | — | — | 0 | — |
|  | 0.0044 | 0 | 0 | — | 0 | — | 0 | — | — | 0 | — | 0 | — | 0 | — | — |
| 52 | 5.6050 | — | — | 99 | — | C | — | — | — | — | C | — | — | — | 95 | — |
|  | 5.6050 | 70 | 25 | — | 25 | — | 98 | — | — | C | — | 80 | — | 99 | — | — |
|  | 1.1210 | 50 | 0 | — | 0 | — | 90 | — | — | 99 | — | 80 | — | 95 | — | — |
|  | 1.1210 | — | — | 85 | — | 0 | — | — | — | — | 97 | — | — | — | 30 | — |
|  | 0.2803 | 0 | 0 | — | 0 | — | 0 | — | — | 50 | — | 10 | — | 10 | — | — |
|  | 0.2803 | — | — | 45 | — | 0 | — | — | — | — | 15 | — | — | — | 0 | — |
|  | 0.0701 | 0 | 0 | — | 0 | — | 0 | — | — | 40 | — | 0 | — | 0 | — | — |
|  | 0.0701 | — | — | 0 | — | 0 | — | — | — | — | 0 | — | — | — | 0 | — |
|  | 0.0175 | 0 | 0 | — | 0 | — | 0 | — | — | 0 | — | 10 | — | 0 | — | — |
|  | 0.0175 | — | — | 0 | — | 0 | — | — | — | — | 0 | — | — | — | 0 | — |
|  | 0.0044 | 0 | 0 | — | 0 | — | 0 | — | — | 0 | — | 0 | — | 0 | — | — |
|  | 0.0044 | — | — | 0 | — | 0 | — | — | — | — | 0 | — | — | — | 0 | — |
| 53 | 5.6050 | 80 | 25 | — | 20 | — | 95 | — | — | 95 | — | 70 | — | 75 | — | — |
|  | 5.6050 | — | — | 99 | — | 65 | — | — | — | — | 75 | — | — | — | 75 | — |
|  | 1.1210 | — | — | 10 | — | 25 | — | — | — | — | 10 | — | — | — | 0 | — |
|  | 1.1210 | 0 | 0 | — | 0 | — | 20 | — | — | 50 | — | 10 | — | 0 | — | — |
|  | 0.2803 | 0 | 0 | — | 0 | — | 0 | — | — | 0 | — | 0 | — | 0 | — | — |
|  | 0.2803 | — | — | 0 | — | 15 | — | — | — | — | 0 | — | — | — | 0 | — |
|  | 0.0701 | 0 | 0 | — | 0 | — | 0 | — | — | 0 | — | 0 | — | 0 | — | — |
|  | 0.0701 | — | — | 0 | — | 10 | — | — | — | — | 0 | — | — | — | 0 | — |
|  | 0.0175 | 0 | N | — | 0 | — | 0 | — | — | 30 | — | 0 | — | 0 | — | — |
|  | 0.0175 | — | — | 0 | — | 0 | — | — | — | — | 0 | — | — | — | 0 | — |
| 54 | 5.6050 | 99 | 80 | — | 65 | — | C | — | — | 99 | — | C | — | C | — | — |
|  | 5.6050 | — | — | C | — | C | — | — | — | — | C | — | — | — | C | — |
|  | 1.1210 | 80 | 50 | — | 25 | — | 98 | — | — | 80 | — | C | — | 99 | — | — |
|  | 1.1210 | — | — | 90 | — | 85 | — | — | — | — | 99 | — | — | — | 99 | — |
|  | 0.2803 | 75 | 10 | — | 0 | — | 95 | — | — | 75 | — | 75 | — | 75 | — | — |
|  | 0.2803 | — | — | 80 | — | 85 | — | — | — | — | 98 | — | — | — | 70 | — |
|  | 0.0701 | 5 | 10 | — | 0 | — | 40 | — | — | 75 | — | 99 | — | 75 | — | — |
|  | 0.0701 | — | — | 60 | — | 15 | — | — | — | — | 50 | — | — | — | 25 | — |
|  | 0.0175 | — | — | 10 | — | 0 | — | — | — | — | 5 | — | — | — | 0 | — |
|  | 0.0175 | 10 | 0 | — | 0 | — | 5 | — | — | 0 | — | 35 | — | 25 | — | — |
|  | 0.0044 | 0 | 10 | — | 0 | — | 0 | — | — | 0 | — | 5 | — | 5 | — | — |
|  | 0.0044 | — | — | 5 | — | 0 | — | — | — | — | 0 | — | — | — | 0 | — |
| 55 | 5.6050 | 95 | 70 | — | 50 | — | 99 | — | — | C | — | 99 | — | 99 | — | — |
|  | 5.6050 | — | — | C | — | C | — | — | — | — | C | — | — | — | 99 | — |
|  | 1.1210 | 25 | 10 | — | 30 | — | 80 | — | — | 99 | — | 80 | — | 90 | — | — |
|  | 1.1210 | — | — | C | — | C | — | — | — | — | 99 | — | — | — | 98 | — |
|  | 0.2803 | — | — | 98 | — | C | — | — | — | — | 90 | — | — | — | 95 | — |
|  | 0.2803 | 10 | 0 | — | 10 | — | 0 | — | — | 70 | — | 50 | — | 65 | — | — |
|  | 0.0701 | 0 | 0 | — | 0 | — | 0 | — | — | 40 | — | 20 | — | 25 | — | — |
|  | 0.0701 | — | — | 35 | — | 95 | — | — | — | — | 55 | — | — | — | 60 | — |
|  | 0.0175 | — | — | 10 | — | 0 | — | — | — | — | 15 | — | — | — | 0 | — |
|  | 0.0175 | 0 | 0 | — | 0 | — | 0 | — | — | 0 | — | 0 | — | 0 | — | — |
| 57 | 5.6050 | 98 | 75 | — | 65 | — | 99 | — | — | 99 | — | C | — | C | — | — |
|  | 5.6050 | — | — | 98 | — | C | — | — | — | — | C | — | — | — | C | — |
|  | 1.1210 | 75 | 50 | — | 25 | — | 98 | — | — | 98 | — | 75 | — | 98 | — | — |
|  | 1.1210 | — | — | 95 | — | C | — | — | — | — | 95 | — | — | — | 98 | — |
|  | 0.2803 | 40 | 0 | — | 0 | — | 75 | — | — | 90 | — | 75 | — | 75 | — | — |
|  | 0.2803 | — | — | 90 | — | 98 | — | — | — | — | 98 | — | — | — | 85 | — |
|  | 0.0701 | 0 | 0 | — | 0 | — | 0 | — | — | 25 | — | 10 | — | 20 | — | — |
|  | 0.0701 | — | — | 45 | — | 30 | — | — | — | — | 20 | — | — | — | 20 | — |
|  | 0.0175 | 0 | 0 | — | 0 | — | 0 | — | — | 0 | — | 0 | — | 0 | — | — |
|  | 0.0175 | — | — | 15 | — | 20 | — | — | — | — | 0 | — | — | — | 0 | — |
|  | 0.0044 | — | — | 0 | — | 0 | — | — | — | — | 0 | — | — | — | 0 | — |
|  | 0.0044 | 0 | 0 | — | 0 | — | 0 | — | — | 0 | — | 0 | — | 0 | — | — |
| 58 | 5.6050 | 95 | 95 | — | 95 | — | 98 | — | — | 98 | — | C | — | 97 | — | — |
|  | 5.6050 | — | — | 98 | — | C | — | — | — | — | C | — | — | — | C | — |
|  | 1.1210 | 90 | 90 | — | 40 | — | 90 | — | — | 95 | — | 95 | — | 95 | — | — |
|  | 1.1210 | — | — | 95 | — | C | — | — | — | — | C | — | — | — | 85 | — |

TABLE 3-continued

Herbicide Secondary Preemergence

| Ex. No. | Rate kg/ha | | | | | | | | | | | | | | | |
|---|---|---|---|---|---|---|---|---|---|---|---|---|---|---|---|---|
| | 0.2803 | 75 | 75 | — | 0 | — | 75 | — | — | 90 | — | 50 | — | 50 | — | — |
| | 0.2803 | — | — | 95 | — | 95 | — | — | — | — | 90 | — | — | — | 75 | — |
| | 0.0701 | 30 | 20 | — | 0 | — | 20 | — | — | 40 | — | 0 | — | 15 | — | — |
| | 0.0701 | — | — | 90 | — | 95 | — | — | — | — | 70 | — | — | — | 50 | — |
| | 0.0175 | 0 | 0 | — | 0 | — | 0 | — | — | 30 | — | 20 | — | 0 | — | — |
| | 0.0175 | — | — | 50 | — | 50 | — | — | — | — | 30 | — | — | — | 30 | — |
| | 0.0044 | — | — | 0 | — | 0 | — | — | — | — | 0 | — | — | — | 0 | — |
| | 0.0044 | 0 | 0 | — | 0 | — | 0 | — | — | 0 | — | 0 | — | 0 | — | — |
| 59 | 5.6050 | 85 | 60 | — | 80 | — | 80 | — | — | 98 | — | 30 | — | 30 | — | — |
| | 5.6050 | — | — | 99 | — | 40 | — | — | — | — | 80 | — | — | — | 60 | — |
| | 1.1210 | 60 | 40 | — | 0 | — | 20 | — | — | 70 | — | 0 | — | 0 | — | — |
| | 1.1210 | — | — | 90 | — | 0 | — | — | — | — | 50 | — | — | — | 20 | — |
| | 0.2803 | — | — | 90 | — | 0 | — | — | — | — | 20 | — | — | — | 0 | — |
| | 0.2803 | 0 | 0 | — | 0 | — | 0 | — | — | 0 | — | 0 | — | 0 | — | — |
| | 0.0701 | — | — | 50 | — | 0 | — | — | — | — | 0 | — | — | — | 0 | — |
| | 0.0701 | 0 | 0 | — | 0 | — | 0 | — | — | 0 | — | 0 | — | 0 | — | — |
| 60 | 5.6050 | — | — | C | — | 99 | — | — | — | — | C | — | — | — | C | — |
| | 5.6050 | 90 | 90 | — | 90 | — | C | — | — | C | — | C | — | C | — | — |
| | 1.1210 | 80 | 70 | — | 35 | — | 95 | — | — | 99 | — | C | — | 90 | — | — |
| | 1.1210 | — | — | C | — | 99 | — | — | — | — | C | — | — | — | C | — |
| | 0.2803 | — | — | C | — | 85 | — | — | — | — | 99 | — | — | — | 85 | — |
| | 0.2803 | 60 | 25 | — | 0 | — | 95 | — | — | 95 | — | 75 | — | 90 | — | — |
| | 0.0701 | 10 | 5 | — | 0 | — | 80 | — | — | 75 | — | 20 | — | 25 | — | — |
| | 0.0701 | — | — | 95 | — | 60 | — | — | — | — | 99 | — | — | — | 75 | — |
| | 0.0175 | — | — | 65 | — | 40 | — | — | — | — | 15 | — | — | — | 5 | — |
| | 0.0175 | 0 | 0 | — | 0 | — | 0 | — | — | 25 | — | 25 | — | 20 | — | — |
| | 0.0044 | — | — | 0 | — | 0 | — | — | — | — | 0 | — | — | — | 0 | — |
| | 0.0044 | 0 | 0 | — | 0 | — | 0 | — | — | 40 | — | 10 | — | 0 | — | — |
| 61 | 5.6050 | 65 | 0 | — | 0 | — | 70 | — | — | 50 | — | 70 | — | 95 | — | — |
| | 5.6050 | — | — | 95 | — | 70 | — | — | — | — | 70 | — | — | — | 65 | — |
| | 1.1210 | 0 | 0 | — | 0 | — | 0 | — | — | 0 | — | 0 | — | 20 | — | — |
| | 1.1210 | — | — | 0 | — | 0 | — | — | — | — | 0 | — | — | — | 0 | — |
| | 0.2803 | — | — | 0 | — | 0 | — | — | — | — | 0 | — | — | — | 0 | — |
| | 0.2803 | 0 | 0 | — | 0 | — | 0 | — | — | 0 | — | 0 | — | 0 | — | — |
| 62 | 5.6050 | 95 | 90 | — | 50 | — | 99 | — | — | 99 | — | 95 | — | 99 | — | — |
| | 5.6050 | — | — | 98 | — | 98 | — | — | — | — | C | — | — | — | C | — |
| | 1.1210 | 90 | 75 | — | 0 | — | 95 | — | — | 95 | — | 70 | — | 98 | — | — |
| | 1.1210 | — | — | 95 | — | 95 | — | — | — | — | 99 | — | — | — | 95 | — |
| | 0.2803 | 80 | 60 | — | 0 | — | 95 | — | — | 95 | — | 70 | — | 95 | — | — |
| | 0.2803 | — | — | 95 | — | C | — | — | — | — | 95 | — | — | — | 85 | — |
| | 0.0701 | — | — | 95 | — | 90 | — | — | — | — | 85 | — | — | — | 70 | — |
| | 0.0701 | 5 | 5 | — | 0 | — | 50 | — | — | 60 | — | 50 | — | 35 | — | — |
| | 0.0175 | — | — | 25 | — | 60 | — | — | — | — | 35 | — | — | — | 30 | — |
| | 0.0175 | 0 | 0 | — | 0 | — | 20 | — | — | 0 | — | 20 | — | 0 | — | — |
| | 0.0044 | 0 | 0 | — | 0 | — | 0 | — | — | 0 | — | 20 | — | 0 | — | — |
| | 0.0044 | — | — | 0 | — | 10 | — | — | — | — | 0 | — | — | — | 0 | — |

| Ex. No. | Rate kg/ha | Bygr | Lacg | Grft | Sube | Colq | Pesw | Cocw | Anbg | Barz | Ruth | Sejg | Wioa | Cwbs | Blgr |
|---|---|---|---|---|---|---|---|---|---|---|---|---|---|---|---|
| 1 | 5.6050 | C | C | C | — | — | — | C | — | — | — | — | — | — | — |
| | 1.1210 | C | C | C | — | — | — | C | — | — | — | — | — | — | — |
| | 0.2803 | 95 | C | 75 | — | — | — | C | — | — | — | — | — | — | — |
| | 0.0701 | 90 | 95 | 80 | — | — | — | 15 | — | — | — | — | — | — | — |
| | 0.0175 | 0 | 90 | 5 | — | — | — | 0 | — | — | — | — | — | — | — |
| | 0.0087 | 0 | 90 | 0 | — | — | — | N | — | — | — | — | — | — | — |
| 2 | 5.6050 | C | C | C | — | — | — | C | — | — | — | — | — | — | — |
| | 1.1210 | C | C | C | — | — | — | C | — | — | — | — | — | — | — |
| | 0.2803 | 99 | C | C | — | — | — | C | — | — | — | — | — | — | — |
| | 0.0701 | C | C | 90 | — | — | — | C | — | — | — | — | — | — | — |
| | 0.0175 | 90 | C | 90 | — | — | — | 85 | — | — | — | — | — | — | — |
| | 0.0044 | 10 | C | 0 | — | — | — | 70 | — | — | — | — | — | — | — |
| 3 | 5.6050 | C | C | C | — | — | — | C | — | — | — | — | — | — | — |
| | 1.1210 | C | C | C | — | — | — | C | — | — | — | — | — | — | — |
| | 0.2803 | C | C | 95 | — | — | — | 95 | — | — | — | — | — | — | — |
| | 0.0701 | 55 | 95 | 60 | — | — | — | 70 | — | — | — | — | — | — | — |
| | 0.0175 | 0 | 65 | 0 | — | — | — | 50 | — | — | — | — | — | — | — |
| | 0.0087 | 0 | 45 | 0 | — | — | — | 40 | — | — | — | — | — | — | — |
| 4 | 5.6050 | C | C | C | — | — | — | C | — | — | — | — | — | — | — |
| | 1.1210 | C | C | C | — | — | — | C | — | — | — | — | — | — | — |
| | 0.2803 | C | C | C | — | — | — | C | — | — | — | — | — | — | — |
| | 0.0701 | 90 | C | 90 | — | — | — | 90 | — | — | — | — | — | — | — |
| | 0.0175 | 30 | 90 | 10 | — | — | — | 75 | — | — | — | — | — | — | — |
| | 0.0087 | 0 | 35 | 0 | — | — | — | 0 | — | — | — | — | — | — | — |
| 5 | 5.6050 | C | C | C | — | — | — | C | — | — | — | — | — | — | — |
| | 1.1210 | C | C | C | — | — | — | C | — | — | — | — | — | — | — |
| | 0.2803 | C | C | C | — | — | — | C | — | — | — | — | — | — | — |
| | 0.0701 | 95 | C | C | — | — | — | 85 | — | — | — | — | — | — | — |
| | 0.0175 | 30 | C | 25 | — | — | — | 75 | — | — | — | — | — | — | — |
| | 0.0087 | 45 | 75 | 30 | — | — | — | 85 | — | — | — | — | — | — | — |
| 6 | 5.6050 | C | C | C | — | — | — | C | — | — | — | — | — | — | — |
| | 1.1210 | C | C | C | — | — | — | C | — | — | — | — | — | — | — |

TABLE 3-continued

Herbicide Secondary Preemergence

| | Rate | | | | | | | | | | | | | | |
|---|---|---|---|---|---|---|---|---|---|---|---|---|---|---|---|
| | 0.2803 | 99 | C | 98 | — | — | — | 99 | — | — | — | — | — | — | — |
| | 0.0701 | 75 | C | 85 | — | — | — | 80 | — | — | — | — | — | — | — |
| | 0.0175 | 45 | 95 | 70 | — | — | — | 40 | — | — | — | — | — | — | — |
| | 0.0087 | 10 | 90 | 60 | — | — | — | 0 | — | — | — | — | — | — | — |
| 7 | 5.6050 | C | C | C | — | — | — | C | — | — | — | — | — | — | — |
| | 1.1210 | C | C | C | — | — | — | C | — | — | — | — | — | — | — |
| | 0.2803 | C | C | C | — | — | — | C | — | — | — | — | — | — | — |
| | 0.0701 | C | C | C | — | — | — | 99 | — | — | — | — | — | — | — |
| | 0.0175 | 90 | 99 | 95 | — | — | — | 90 | — | — | — | — | — | — | — |
| | 0.0087 | 60 | 95 | 85 | — | — | — | 50 | — | — | — | — | — | — | — |
| 8 | 5.6050 | C | C | C | — | — | — | C | — | — | — | — | — | — | — |
| | 1.1210 | C | C | C | — | — | — | C | — | — | — | — | — | — | — |
| | 0.2803 | 99 | C | C | — | — | — | 99 | — | — | — | — | — | — | — |
| | 0.0701 | 99 | C | 90 | — | — | — | 90 | — | — | — | — | — | — | — |
| | 0.0175 | 0 | C | 60 | — | — | — | 90 | — | — | — | — | — | — | — |
| | 0.0087 | 50 | 90 | 55 | — | — | — | N | — | — | — | — | — | — | — |
| 9 | 11.2100 | C | C | — | — | — | — | — | — | — | — | C | — | — | — |
| | 11.2100 | — | — | C | — | — | — | C | C | 98 | 95 | — | 99 | — | — |
| | 5.6050 | C | C | — | — | — | — | — | — | — | — | C | — | — | — |
| | 5.6050 | — | — | C | — | — | — | C | C | 90 | 90 | — | 99 | — | — |
| | 1.1210 | — | — | C | — | — | — | C | C | 65 | 60 | — | 95 | — | — |
| | 1.1210 | C | 99 | — | — | — | — | — | — | — | — | 99 | — | — | — |
| | 0.2803 | 50 | 75 | — | — | — | — | — | — | — | — | 25 | — | — | — |
| | 0.2803 | — | — | 60 | — | — | — | 90 | 90 | 15 | 0 | — | 20 | — | — |
| 10 | 5.6050 | C | C | — | — | — | — | — | — | — | — | C | — | — | — |
| | 5.6050 | — | — | C | — | — | — | C | C | C | 90 | — | C | — | — |
| | 1.1210 | — | — | C | — | — | — | 60 | C | 95 | 20 | — | 98 | — | — |
| | 1.1210 | 99 | 99 | — | — | — | — | — | — | — | — | 99 | — | — | — |
| | 0.2803 | 75 | 98 | — | — | — | — | — | — | — | — | 60 | — | — | — |
| | 0.2803 | — | — | 90 | — | — | — | 30 | 98 | 75 | 10 | — | 90 | — | — |
| | 0.0701 | 0 | 0 | — | — | — | — | — | — | — | — | 0 | — | — | — |
| | 0.0701 | — | — | 0 | — | — | — | 0 | 0 | 0 | 0 | — | 0 | — | — |
| 11 | 5.6050 | C | C | — | — | — | — | — | — | — | — | C | — | — | — |
| | 5.6050 | — | — | 99 | — | — | — | C | C | 10 | 20 | — | 95 | — | — |
| | 1.1210 | 90 | C | — | — | — | — | — | — | — | — | 99 | — | — | — |
| | 1.1210 | — | — | 95 | — | — | — | 99 | 99 | 0 | 15 | — | 80 | — | — |
| | 0.2803 | — | — | 0 | — | — | — | 0 | 0 | 0 | 0 | — | 20 | — | — |
| | 0.2803 | 0 | 40 | — | — | — | — | — | — | — | — | 30 | — | — | — |
| | 0.0701 | 0 | 0 | — | — | — | — | — | — | — | — | 0 | — | — | — |
| | 0.0701 | — | — | 10 | — | — | — | N | 0 | 0 | 0 | — | 20 | — | — |
| 12 | 5.6050 | C | C | — | — | — | — | — | — | — | — | C | — | — | — |
| | 5.6050 | — | — | C | — | — | — | C | C | 70 | 60 | — | 99 | — | — |
| | 1.1210 | C | C | — | — | — | — | — | — | — | — | C | — | — | — |
| | 1.1210 | — | — | C | — | — | — | C | C | 10 | 20 | — | 90 | — | — |
| | 0.2803 | — | — | 98 | — | — | — | 99 | C | 15 | 50 | — | 70 | — | — |
| | 0.2803 | C | C | — | — | — | — | — | — | — | — | C | — | — | — |
| | 0.0701 | 80 | 98 | — | — | — | — | — | — | — | — | 80 | — | — | — |
| | 0.0701 | — | — | 99 | — | — | — | C | C | 0 | 0 | — | 50 | — | — |
| | 0.0175 | 30 | 50 | — | — | — | — | — | — | — | — | 30 | — | — | — |
| | 0.0175 | — | — | 60 | — | — | — | 20 | 98 | 0 | 0 | — | 15 | — | — |
| 13 | 5.6050 | C | C | C | — | — | — | C | — | — | — | — | — | — | — |
| | 1.1210 | C | C | C | — | — | — | C | — | — | — | — | — | — | — |
| | 0.2803 | C | 95 | C | — | — | — | 85 | — | — | — | — | — | — | — |
| | 0.0701 | 95 | 95 | 90 | — | — | — | 40 | — | — | — | — | — | — | — |
| | 0.0175 | 95 | 95 | 80 | — | — | — | 40 | — | — | — | — | — | — | — |
| | 0.0087 | 90 | 95 | 90 | — | — | — | 45 | — | — | — | — | — | — | — |
| 14(A) | 5.6050 | C | C | C | — | — | — | C | — | — | — | — | — | — | — |
| (A) | 1.1210 | C | C | C | — | — | — | C | — | — | — | — | — | — | — |
| (A) | 0.2803 | 95 | C | 95 | — | — | — | 95 | — | — | — | — | — | — | — |
| (A) | 0.0701 | 90 | C | 90 | — | — | — | 35 | — | — | — | — | — | — | — |
| (A) | 0.0175 | 75 | C | 60 | — | — | — | 35 | — | — | — | — | — | — | — |
| 15 | 5.6050 | C | C | C | — | — | — | — | — | — | — | — | — | — | — |
| | 1.1210 | C | C | C | — | — | — | — | — | — | — | — | — | — | — |
| | 0.2803 | C | C | C | — | — | — | — | — | — | — | — | — | — | — |
| | 0.0701 | C | 99 | C | — | — | — | — | — | — | — | — | — | — | — |
| | 0.0175 | 80 | 99 | 60 | — | — | — | — | — | — | — | — | — | — | — |
| | 0.0087 | 0 | 55 | 50 | — | — | — | — | — | — | — | — | — | — | — |
| 16(B) | 5.6050 | C | C | C | — | — | — | C | — | — | — | — | — | — | — |
| (B) | 1.1210 | C | C | C | — | — | — | C | — | — | — | — | — | — | — |
| (B) | 0.2803 | C | C | C | — | — | — | C | — | — | — | — | — | — | — |
| (B) | 0.0701 | 99 | C | 99 | — | — | — | 95 | — | — | — | — | — | — | — |
| (B) | 0.0175 | 99 | C | 99 | — | — | — | 90 | — | — | — | — | — | — | — |
| (B) | 0.0087 | 80 | 99 | 75 | — | — | — | 20 | — | — | — | — | — | — | — |
| 17 | 5.6050 | 95 | C | 95 | — | — | — | 95 | — | — | — | — | — | — | — |
| | 1.1210 | 95 | C | 95 | — | — | — | 95 | — | — | — | — | — | — | — |
| | 0.2803 | 80 | C | 80 | — | — | — | 90 | — | — | — | — | — | — | — |
| | 0.0701 | 70 | 75 | 40 | — | — | — | 0 | — | — | — | — | — | — | — |
| | 0.0175 | 0 | 40 | 0 | — | — | — | N | — | — | — | — | — | — | — |
| 18 | 5.6050 | C | C | C | — | — | — | C | — | — | — | — | — | — | — |
| | 1.1210 | C | C | C | — | — | — | 95 | — | — | — | — | — | — | — |
| | 0.2803 | 95 | C | C | — | — | — | 95 | — | — | — | — | — | — | — |

TABLE 3-continued

Herbicide Secondary Preemergence

| | | | | | | | | | | | | | | | | |
|---|---|---|---|---|---|---|---|---|---|---|---|---|---|---|---|---|
| | 0.0701 | 90 | C | 90 | — | — | — | 30 | — | — | — | — | — | — | — |
| | 0.0175 | 65 | 90 | 55 | — | — | — | 15 | — | — | — | — | — | — | — |
| | 0.0087 | 0 | 30 | 0 | — | — | — | 45 | — | — | — | — | — | — | — |
| 19 | 5.6050 | C | C | C | — | — | — | C | — | — | — | — | — | — | — |
| | 1.1210 | C | C | 85 | — | — | — | C | — | — | — | — | — | — | — |
| | 0.2803 | 90 | C | 75 | — | — | — | 95 | — | — | — | — | — | — | — |
| | 0.0701 | 40 | 75 | 35 | — | — | — | 70 | — | — | — | — | — | — | — |
| | 0.0175 | 40 | 60 | 35 | — | — | — | 30 | — | — | — | — | — | — | — |
| | 0.0087 | 0 | 30 | 0 | — | — | — | 25 | — | — | — | — | — | — | — |
| 21 | 5.6050 | — | — | C | — | — | — | C | C | 70 | 80 | — | 99 | — | — |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | C | C | 40 | 90 | — | C | — | — |
| | 0.2803 | C | C | — | — | — | — | — | — | — | — | C | — | — | — |
| | 0.2803 | — | — | C | — | — | — | C | C | 30 | 95 | — | 90 | — | — |
| | 0.0701 | C | C | — | — | — | — | — | — | — | — | 98 | — | — | — |
| | 0.0701 | — | — | C | — | — | — | C | C | 10 | 30 | — | 75 | — | — |
| | 0.0175 | 80 | 95 | — | — | — | — | — | — | — | — | 80 | — | — | — |
| | 0.0175 | — | — | 75 | — | — | — | 20 | 99 | 0 | 0 | — | 50 | — | — |
| | 0.0044 | 20 | 75 | — | — | — | — | — | — | — | — | 0 | — | — | — |
| | 0.0044 | — | — | 0 | — | — | — | 0 | 50 | 0 | 0 | — | 0 | — | — |
| 22 | 5.6050 | C | C | — | — | — | — | — | — | — | — | 98 | — | — | — |
| | 5.6050 | — | — | C | — | — | — | C | C | 75 | 40 | — | 90 | — | — |
| | 1.1210 | 40 | 99 | — | — | — | — | — | — | — | — | 35 | — | — | — |
| | 1.1210 | — | — | 50 | — | — | — | 20 | C | 25 | N | — | 50 | — | — |
| | 0.2803 | — | — | 0 | — | — | — | 0 | 0 | 0 | 0 | — | 0 | — | — |
| | 0.2803 | 20 | 60 | — | — | — | — | — | — | — | — | 20 | — | — | — |
| | 0.0701 | — | — | 0 | — | — | — | 0 | 0 | 0 | 0 | — | 0 | — | — |
| | 0.0701 | 10 | 20 | — | — | — | — | — | — | — | — | 0 | — | — | — |
| 23 | 5.6050 | C | C | — | — | — | — | — | — | — | — | C | — | — | — |
| | 5.6050 | — | — | C | — | — | — | C | C | C | 80 | — | C | — | — |
| | 1.1210 | — | — | C | — | — | — | C | C | C | 60 | — | 99 | — | — |
| | 1.1210 | C | C | — | — | — | — | — | — | — | — | 99 | — | — | — |
| | 0.2803 | C | C | — | — | — | — | — | — | — | — | 98 | — | — | — |
| | 0.2803 | — | — | 90 | — | — | — | 20 | C | 75 | 0 | — | 50 | — | — |
| | 0.0701 | 80 | 95 | — | — | — | — | — | — | — | — | 60 | — | — | — |
| | 0.0701 | — | — | 20 | — | — | — | 0 | 0 | 0 | 0 | — | 0 | — | — |
| | 0.0175 | 25 | 0 | — | — | — | — | — | — | — | — | 0 | — | — | — |
| | 0.0175 | — | — | 0 | — | — | — | 0 | 0 | 0 | 0 | — | 0 | — | — |
| 24 | 5.6050 | — | — | C | — | — | — | C | C | 95 | 90 | — | C | — | — |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | C | C | 95 | 90 | — | C | — | — |
| | 0.2803 | C | C | — | — | — | — | — | — | — | — | C | — | — | — |
| | 0.2803 | — | — | C | — | — | — | 99 | C | 25 | 10 | — | 98 | — | — |
| | 0.0701 | C | C | — | — | — | — | — | — | — | — | 99 | — | — | — |
| | 0.0701 | — | — | 98 | — | — | — | 98 | C | 0 | 0 | — | 95 | — | — |
| | 0.0175 | 95 | 99 | — | — | — | — | — | — | — | — | 15 | — | — | — |
| | 0.0175 | — | — | 50 | — | — | — | 60 | 60 | 0 | 0 | — | 70 | — | — |
| | 0.0044 | 15 | 95 | — | — | — | — | — | — | — | — | 0 | — | — | — |
| | 0.0044 | — | — | 0 | — | — | — | 35 | 0 | 0 | 0 | — | 15 | — | — |
| 25 | 5.6050 | — | — | C | — | — | — | C | C | 65 | 80 | — | 99 | — | — |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | 98 | C | 15 | 15 | — | 90 | — | — |
| | 0.2803 | 99 | C | — | — | — | — | — | — | — | — | 99 | — | — | — |
| | 0.2803 | — | — | C | — | — | — | 75 | C | 0 | 10 | — | 15 | — | — |
| | 0.0701 | 50 | 99 | — | — | — | — | — | — | — | — | 50 | — | — | — |
| | 0.0701 | — | — | 90 | — | — | — | 0 | 90 | 0 | 0 | — | 0 | — | — |
| | 0.0175 | 10 | 75 | — | — | — | — | — | — | — | — | 25 | — | — | — |
| | 0.0175 | — | — | 70 | — | — | — | 0 | 10 | 0 | 0 | — | 0 | — | — |
| 26 | 5.6050 | — | — | C | — | — | — | C | C | 90 | 80 | — | C | — | — |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | 98 | C | 20 | 15 | — | 90 | — | — |
| | 0.2803 | C | C | — | — | — | — | — | — | — | — | 99 | — | — | — |
| | 0.2803 | — | — | 98 | — | — | — | 75 | 99 | 0 | 0 | — | 15 | — | — |
| | 0.0701 | 30 | 60 | — | — | — | — | — | — | — | — | 30 | — | — | — |
| | 0.0701 | — | — | 99 | — | — | — | 65 | 99 | 0 | 0 | — | N | — | — |
| | 0.0175 | 0 | 25 | — | — | — | — | — | — | — | — | 0 | — | — | — |
| | 0.0175 | — | — | 60 | — | — | — | 15 | 50 | 0 | 0 | — | 0 | — | — |
| 27 | 5.6050 | — | — | C | — | — | — | C | C | 90 | 90 | — | 99 | — | — |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | C | C | 40 | 30 | — | 95 | — | — |
| | 0.2803 | C | C | — | — | — | — | — | — | — | — | 99 | — | — | — |
| | 0.2803 | — | — | C | — | — | — | C | C | 20 | 20 | — | 75 | — | — |
| | 0.0701 | — | — | 95 | — | — | — | 65 | 99 | 0 | 10 | — | 60 | — | — |
| | 0.0701 | 95 | 99 | — | — | — | — | — | — | — | — | 40 | — | — | — |
| | 0.0175 | 10 | 65 | — | — | — | — | — | — | — | — | 20 | — | — | — |
| | 0.0175 | — | — | 55 | — | — | — | 0 | 60 | 0 | 0 | — | 0 | — | — |

TABLE 3-continued

Herbicide Secondary Preemergence

| Ex# | Rate | C1 | C2 | C3 | C4 | C5 | C6 | C7 | C8 | C9 | C10 | C11 | C12 | C13 | C14 | C15 |
|---|---|---|---|---|---|---|---|---|---|---|---|---|---|---|---|---|
| | 0.0044 | 0 | 20 | — | — | — | — | — | — | — | — | — | 0 | — | — | — |
| | 0.0044 | — | — | 0 | — | — | — | 0 | 0 | 0 | 0 | — | 0 | — | — | — |
| 30 | 11.2100 | 95 | 99 | — | — | — | — | — | — | — | — | — | 99 | — | — | — |
| | 11.2100 | — | — | 90 | — | — | — | 80 | 90 | 10 | 0 | — | 20 | — | — | — |
| | 5.6050 | — | — | 10 | — | — | — | 0 | 45 | 0 | 20 | — | 20 | — | — | — |
| | 5.6050 | 50 | 95 | — | — | — | — | — | — | — | — | 30 | — | — | — | — |
| | 1.1210 | 0 | 0 | — | — | — | — | — | — | — | — | — | 0 | — | — | — |
| | 1.1210 | — | — | 0 | — | — | — | 0 | 10 | 0 | 0 | — | 15 | — | — | — |
| 32 | 5.6050 | 90 | C | — | — | — | — | — | — | — | — | C | — | — | — | — |
| | 5.6050 | — | — | 80 | — | — | — | 20 | 90 | 20 | 10 | — | 15 | — | — | — |
| | 1.1210 | 0 | 75 | — | — | — | — | — | — | — | — | 80 | — | — | — | — |
| | 1.1210 | — | — | 90 | — | — | — | 80 | 80 | 0 | 15 | — | 0 | — | — | — |
| | 0.2803 | — | — | 60 | — | — | — | 80 | 10 | 0 | 20 | — | 0 | — | — | — |
| | 0.2803 | 0 | 25 | — | — | — | — | — | — | — | — | 0 | — | — | — | — |
| 33 | 5.6050 | C | C | — | — | — | — | — | — | — | — | C | — | — | — | — |
| | 5.6050 | — | — | C | — | — | — | C | C | C | C | — | C | — | — | — |
| | 1.1210 | C | C | — | — | — | — | — | — | — | — | C | — | — | — | — |
| | 1.1210 | — | — | 99 | — | — | — | C | C | 90 | 85 | — | 98 | — | — | — |
| | 0.2803 | 99 | 99 | — | — | — | — | — | — | — | — | 99 | — | — | — | — |
| | 0.2803 | — | — | 60 | — | — | — | 90 | C | 35 | 50 | — | 20 | — | — | — |
| | 0.0701 | 40 | 25 | — | — | — | — | — | — | — | — | 50 | — | — | — | — |
| | 0.0701 | — | — | 0 | — | — | — | 20 | 80 | 0 | 20 | — | 0 | — | — | — |
| | 0.0175 | 0 | 0 | — | — | — | — | — | — | — | — | 0 | — | — | — | — |
| | 0.0175 | — | — | 0 | — | — | — | N | 20 | 0 | N | — | 0 | — | — | — |
| | 0.0044 | 0 | 0 | — | — | — | — | — | — | — | — | 0 | — | — | — | — |
| | 0.0044 | — | — | 0 | — | — | — | 10 | 0 | 0 | 20 | — | 0 | — | — | — |
| 35 | 5.6050 | — | — | C | — | — | — | C | C | C | C | — | C | — | — | — |
| | 5.6050 | C | C | — | — | — | — | — | — | — | — | C | — | — | — | — |
| | 1.1210 | C | C | C | — | — | — | — | — | — | — | C | — | — | — | — |
| | 1.1210 | — | — | C | — | — | — | C | C | 98 | 80 | — | 99 | — | — | — |
| | 0.2803 | C | 99 | — | — | — | — | — | — | — | — | 98 | — | — | — | — |
| | 0.2803 | — | — | C | — | — | — | 99 | C | 80 | 75 | — | 75 | — | — | — |
| | 0.0701 | 99 | 98 | — | — | — | — | — | — | — | — | 75 | — | — | — | — |
| | 0.0701 | — | — | 75 | — | — | — | 35 | C | 0 | 30 | — | 0 | — | — | — |
| | 0.0175 | 0 | 0 | — | — | — | — | — | — | — | — | 0 | — | — | — | — |
| | 0.0175 | — | — | 0 | — | — | — | 0 | 0 | 0 | 0 | — | 0 | — | — | — |
| | 0.0044 | — | — | 0 | — | — | — | 0 | 0 | 0 | 0 | — | 0 | — | — | — |
| | 0.0044 | 0 | 0 | — | — | — | — | — | — | — | — | 0 | — | — | — | — |
| 36 | 5.6050 | — | — | 99 | — | — | — | C | C | 40 | 30 | — | 75 | — | — | — |
| | 5.6050 | C | C | — | — | — | — | — | — | — | — | 98 | — | — | — | — |
| | 1.1210 | 70 | 98 | — | — | — | — | — | — | — | — | 60 | — | — | — | — |
| | 1.1210 | — | — | 80 | — | — | — | 50 | 95 | 0 | 25 | — | 50 | — | — | — |
| | 0.2803 | 10 | 75 | — | — | — | — | — | — | — | — | 0 | — | — | — | — |
| | 0.2803 | — | — | 0 | — | — | — | 0 | 35 | 0 | 0 | — | 0 | — | — | — |
| | 0.0701 | 10 | 20 | — | — | — | — | — | — | — | — | 0 | — | — | — | — |
| | 0.0701 | — | — | 0 | — | — | — | 0 | 0 | 0 | 0 | — | 0 | — | — | — |
| 37(A) | 5.6050 | C | C | C | — | — | — | C | — | — | — | — | — | — | — | — |
| (A) | 1.1210 | C | C | C | — | — | — | 90 | — | — | — | — | — | — | — | — |
| (A) | 0.2803 | 90 | 95 | 95 | — | — | — | 75 | — | — | — | — | — | — | — | — |
| (A) | 0.0701 | 70 | 90 | 65 | — | — | — | 45 | — | — | — | — | — | — | — | — |
| (A) | 0.0175 | 10 | 30 | 25 | — | — | — | 35 | — | — | — | — | — | — | — | — |
| (A) | 0.0087 | 20 | 25 | 35 | — | — | — | 30 | — | — | — | — | — | — | — | — |
| 38(D) | 5.6050 | C | C | C | — | — | — | — | — | — | — | — | — | — | — | — |
| (D) | 1.1210 | C | C | C | — | — | — | — | — | — | — | — | — | — | — | — |
| (D) | 0.2803 | C | C | C | — | — | — | — | — | — | — | — | — | — | — | — |
| (D) | 0.0701 | C | C | 95 | — | — | — | — | — | — | — | — | — | — | — | — |
| (D) | 0.0175 | 90 | C | 80 | — | — | — | — | — | — | — | — | — | — | — | — |
| (D) | 0.0087 | 90 | 45 | 75 | — | — | — | — | — | — | — | — | — | — | — | — |
| 39 | 5.6050 | C | C | 99 | — | — | — | — | — | — | — | — | — | — | — | — |
| | 1.1210 | C | C | C | — | — | — | — | — | — | — | — | — | — | — | — |
| | 0.2803 | 75 | 75 | 40 | — | — | — | — | — | — | — | — | — | — | — | — |
| | 0.0701 | 0 | 45 | 0 | — | — | — | — | — | — | — | — | — | — | — | — |
| 40 | 5.6050 | C | C | C | — | — | — | — | — | — | — | — | — | — | — | — |
| | 1.1210 | C | C | C | — | — | — | — | — | — | — | — | — | — | — | — |
| | 0.2803 | 90 | C | 90 | — | — | — | — | — | — | — | — | — | — | — | — |
| | 0.0701 | 0 | 55 | 20 | — | — | — | — | — | — | — | — | — | — | — | — |
| 41 | 5.6050 | C | C | C | — | — | — | — | — | — | — | — | — | — | — | — |
| | 1.1210 | C | C | C | — | — | — | — | — | — | — | — | — | — | — | — |
| | 0.2803 | C | C | 95 | — | — | — | — | — | — | — | — | — | — | — | — |
| | 0.0701 | 95 | 95 | 80 | — | — | — | — | — | — | — | — | — | — | — | — |
| | 0.0175 | 0 | 40 | 0 | — | — | — | — | — | — | — | — | — | — | — | — |
| | 0.0087 | 0 | 0 | 0 | — | — | — | — | — | — | — | — | — | — | — | — |
| 42(D) | 5.6050 | C | C | C | — | — | — | — | — | — | — | — | — | — | — | — |
| (D) | 1.1210 | C | C | C | — | — | — | — | — | — | — | — | — | — | — | — |
| (D) | 0.2803 | C | C | 95 | — | — | — | — | — | — | — | — | — | — | — | — |
| (D) | 0.0701 | 85 | 90 | 55 | — | — | — | — | — | — | — | — | — | — | — | — |
| (D) | 0.0175 | 25 | 0 | 0 | — | — | — | — | — | — | — | — | — | — | — | — |
| (D) | 0.0087 | N | 0 | 35 | — | — | — | — | — | — | — | — | — | — | — | — |
| 43(C) | 5.6050 | 95 | C | 95 | — | — | — | — | — | — | — | — | — | — | — | — |
| (C) | 1.1210 | 90 | 80 | 90 | — | — | — | — | — | — | — | — | — | — | — | — |
| (C) | 0.2803 | 40 | 80 | 30 | — | — | — | — | — | — | — | — | — | — | — | — |

TABLE 3-continued

Herbicide Secondary Preemergence

| | | | | | | | | | | | | | | | |
|---|---|---|---|---|---|---|---|---|---|---|---|---|---|---|---|
| (C) | 0.0701 | 0 | 0 | 0 | — | — | — | — | — | — | — | — | — | — | — |
| 44 | 5.6050 | C | C | C | — | — | — | — | — | — | — | — | — | — | — |
| | 1.1210 | 95 | C | 95 | — | — | — | — | — | — | — | — | — | — | — |
| | 0.2803 | 90 | C | 55 | — | — | — | — | — | — | — | — | — | — | — |
| | 0.0701 | 85 | 35 | 25 | — | — | — | — | — | — | — | — | — | — | — |
| 45 | 5.6050 | C | C | — | — | — | — | — | — | — | — | C | — | — | — |
| | 5.6050 | — | — | C | — | — | — | C | C | 98 | 90 | — | 99 | — | — |
| | 1.1210 | — | — | C | — | — | — | C | C | 80 | 80 | — | 99 | — | — |
| | 1.1210 | C | C | — | — | — | — | — | — | — | — | C | — | — | — |
| | 0.2803 | C | C | — | — | — | — | — | — | — | — | C | — | — | — |
| | 0.2803 | — | — | C | — | — | — | 99 | C | 25 | 70 | — | 95 | — | — |
| | 0.0701 | 99 | 99 | — | — | — | — | — | — | — | — | 75 | — | — | — |
| | 0.0701 | — | — | 99 | — | — | — | 60 | C | 10 | 40 | — | 70 | — | — |
| | 0.0175 | 75 | 98 | — | — | — | — | — | — | — | — | 60 | — | — | — |
| | 0.0175 | — | — | 90 | — | — | — | N | 95 | 0 | 10 | — | 25 | — | — |
| | 0.0044 | 0 | 50 | — | — | — | — | — | — | — | — | 0 | — | — | — |
| | 0.0044 | — | — | 20 | — | — | — | 0 | 20 | 0 | 20 | — | 0 | — | — |
| 46 | 5.6050 | C | C | C | — | — | — | C | — | — | — | — | — | — | — |
| | 1.1210 | C | C | C | — | — | — | C | — | — | — | — | — | — | — |
| | 0.2803 | C | C | C | — | — | — | C | — | — | — | — | — | — | — |
| | 0.0701 | 70 | 99 | 85 | — | — | — | 90 | — | — | — | — | — | — | — |
| | 0.0175 | 60 | 90 | 75 | — | — | — | 15 | — | — | — | — | — | — | — |
| | 0.0087 | 10 | 90 | 55 | — | — | — | 0 | — | — | — | — | — | — | — |
| 47(E) | 5.6050 | C | C | C | — | — | — | C | — | — | — | — | — | — | — |
| (E) | 1.1210 | C | C | C | — | — | — | 95 | — | — | — | — | — | — | — |
| (E) | 0.2803 | 85 | C | 85 | — | — | — | 95 | — | — | — | — | — | — | — |
| (E) | 0.0701 | 45 | 95 | 45 | — | — | — | 35 | — | — | — | — | — | — | — |
| (E) | 0.0175 | 0 | 0 | 0 | — | — | — | 0 | — | — | — | — | — | — | — |
| 48 | 5.6050 | C | C | C | — | — | — | C | — | — | — | — | — | — | — |
| | 1.1210 | C | C | 95 | — | — | — | C | — | — | — | — | — | — | — |
| | 0.2803 | 90 | C | 90 | — | — | — | C | — | — | — | — | — | — | — |
| | 0.0701 | 40 | 95 | 45 | — | — | — | 55 | — | — | — | — | — | — | — |
| | 0.0175 | 20 | 45 | 0 | — | — | — | 35 | — | — | — | — | — | — | — |
| | 0.0087 | 0 | 65 | 0 | — | — | — | 30 | — | — | — | — | — | — | — |
| 49 | 5.6050 | C | C | C | — | — | — | C | — | — | — | — | — | — | — |
| | 1.1210 | 90 | C | 90 | — | — | — | 90 | — | — | — | — | — | — | — |
| | 0.2803 | 70 | 95 | 35 | — | — | — | 90 | — | — | — | — | — | — | — |
| | 0.0701 | 0 | 85 | 0 | — | — | — | 90 | — | — | — | — | — | — | — |
| | 0.0175 | 0 | 50 | 0 | — | — | — | 45 | — | — | — | — | — | — | — |
| | 0.0087 | 0 | 0 | 0 | — | — | — | 0 | — | — | — | — | — | — | — |
| 50 | 5.6050 | C | C | C | — | — | — | C | — | — | — | — | — | — | — |
| | 1.1210 | C | C | C | — | — | — | C | — | — | — | — | — | — | — |
| | 0.2803 | 98 | C | C | — | — | — | C | — | — | — | — | — | — | — |
| | 0.0701 | 95 | C | 90 | — | — | — | 75 | — | — | — | — | — | — | — |
| | 0.0175 | 70 | 90 | 55 | — | — | — | 30 | — | — | — | — | — | — | — |
| 51 | 5.6050 | C | C | — | — | — | — | — | — | — | — | C | — | — | — |
| | 5.6050 | — | — | C | — | — | — | C | — | — | 98 | — | C | C | C |
| | 1.1210 | C | C | — | — | — | — | — | — | — | — | C | — | — | — |
| | 1.1210 | — | — | C | — | — | — | C | — | — | 65 | — | 99 | 98 | C |
| | 0.2803 | — | — | C | — | — | — | C | — | — | 40 | — | 90 | 70 | 99 |
| | 0.2803 | C | C | — | — | — | — | — | — | — | — | C | — | — | — |
| | 0.0701 | 98 | C | — | — | — | — | — | — | — | — | 99 | — | — | — |
| | 0.0701 | — | — | 90 | — | — | — | 45 | — | — | 30 | — | 80 | 35 | 98 |
| | 0.0175 | 25 | 98 | — | — | — | — | — | — | — | — | 50 | — | — | — |
| | 0.0175 | — | — | 85 | — | — | — | 15 | — | — | 20 | — | 55 | 35 | 60 |
| | 0.0044 | — | — | 0 | — | — | — | 0 | — | — | 10 | — | 15 | 5 | 10 |
| | 0.0044 | 0 | 0 | — | — | — | — | — | — | — | — | 0 | — | — | — |
| 52 | 5.6050 | — | — | C | — | — | — | C | — | — | 90 | — | C | C | C |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | 90 | — | — | 40 | — | 75 | 45 | 99 |
| | 0.2803 | 95 | C | — | — | — | — | — | — | — | — | 95 | — | — | — |
| | 0.2803 | — | — | C | — | — | — | 10 | — | — | 0 | — | 0 | 0 | 55 |
| | 0.0701 | 0 | 25 | — | — | — | — | — | — | — | — | 0 | — | — | — |
| | 0.0701 | — | — | 35 | — | — | — | 0 | — | — | 0 | — | 0 | 0 | 0 |
| | 0.0175 | 0 | 0 | — | — | — | — | — | — | — | — | 0 | — | — | — |
| | 0.0175 | — | — | 0 | — | — | — | 0 | — | — | 0 | — | 0 | 0 | 0 |
| | 0.0044 | 0 | 0 | — | — | — | — | — | — | — | — | 0 | — | — | — |
| | 0.0044 | — | — | 0 | — | — | — | 0 | — | — | 0 | — | 0 | 0 | 0 |
| 53 | 5.6050 | C | C | — | — | — | — | — | — | — | — | C | — | — | — |
| | 5.6050 | — | — | C | — | — | — | C | — | — | 50 | — | 90 | 99 | C |
| | 1.1210 | — | — | 75 | — | — | — | 20 | — | — | 5 | — | 5 | 20 | 10 |
| | 1.1210 | 75 | C | — | — | — | — | — | — | — | — | 98 | — | — | — |
| | 0.2803 | 0 | 0 | — | — | — | — | — | — | — | — | 50 | — | — | — |
| | 0.2803 | — | — | 20 | — | — | — | 5 | — | — | 5 | — | 0 | 0 | 0 |
| | 0.0701 | 0 | 0 | — | — | — | — | — | — | — | — | 25 | — | — | — |
| | 0.0701 | — | — | 0 | — | — | — | 0 | — | — | 0 | — | 0 | 0 | 0 |
| | 0.0175 | 0 | 25 | — | — | — | — | — | — | — | — | 0 | — | — | — |
| | 0.0175 | — | — | 0 | — | — | — | 0 | — | — | 0 | — | 0 | 0 | 0 |
| 54 | 5.6050 | C | C | — | — | — | — | — | — | — | — | C | — | — | — |
| | 5.6050 | — | — | C | — | — | — | C | — | — | C | — | 98 | C | C |

TABLE 3-continued

Herbicide Secondary Preemergence

| | | | | | | | | | | | | | | | |
|---|---|---|---|---|---|---|---|---|---|---|---|---|---|---|---|
| | 1.1210 | C | C | — | — | — | — | — | — | — | — | C | — | — | — |
| | 1.1210 | — | — | C | — | — | — | 99 | — | — | 90 | — | 85 | C | C |
| | 0.2803 | C | C | — | — | — | — | — | — | — | — | C | — | — | — |
| | 0.2803 | — | — | C | — | — | — | C | — | — | 75 | — | 70 | 75 | C |
| | 0.0701 | C | C | — | — | — | — | — | — | — | — | C | — | — | — |
| | 0.0701 | — | — | C | — | — | — | C | — | — | 55 | — | 85 | 65 | 99 |
| | 0.0175 | — | — | 80 | — | — | — | 0 | — | — | 5 | — | 5 | 0 | 75 |
| | 0.0175 | 99 | C | — | — | — | — | — | — | — | — | 99 | — | — | — |
| | 0.0044 | 0 | 65 | — | — | — | — | — | — | — | — | 35 | — | — | — |
| | 0.0044 | — | — | 15 | — | — | — | 0 | — | — | 35 | — | 0 | 0 | 20 |
| 55 | 5.6050 | C | C | — | — | — | — | — | — | — | — | C | — | — | — |
| | 5.6050 | — | — | C | — | — | — | C | C | C | 95 | — | C | — | — |
| | 1.1210 | C | C | — | — | — | — | — | — | — | — | 98 | — | — | — |
| | 1.1210 | — | — | C | — | — | — | C | C | 98 | 80 | — | 95 | — | — |
| | 0.2803 | — | — | 80 | — | — | — | C | C | 95 | 90 | — | 90 | — | — |
| | 0.2803 | 99 | 99 | — | — | — | — | — | — | — | — | 80 | — | — | — |
| | 0.0701 | 90 | 80 | — | — | — | — | — | — | — | — | 50 | — | — | — |
| | 0.0701 | — | — | 20 | — | — | — | 70 | 98 | 25 | 60 | — | 30 | — | — |
| | 0.0175 | — | — | 0 | — | — | — | 10 | 0 | 20 | 30 | — | 10 | — | — |
| | 0.0175 | 20 | 50 | — | — | — | — | — | — | — | — | 0 | — | — | — |
| 57 | 5.6050 | C | C | — | — | — | — | — | — | — | — | C | — | — | — |
| | 5.6050 | — | — | C | — | — | — | C | C | 95 | 90 | — | C | — | — |
| | 1.1210 | C | C | — | — | — | — | — | — | — | — | C | — | — | — |
| | 1.1210 | — | — | C | — | — | — | C | C | 30 | 70 | — | 95 | — | — |
| | 0.2803 | C | C | — | — | — | — | — | — | — | — | 99 | — | — | — |
| | 0.2803 | — | — | C | — | — | — | 99 | C | 25 | 40 | — | 90 | — | — |
| | 0.0701 | 98 | C | — | — | — | — | — | — | — | — | 70 | — | — | — |
| | 0.0701 | — | — | 99 | — | — | — | 50 | C | 0 | 30 | — | 15 | — | — |
| | 0.0175 | 30 | 65 | — | — | — | — | — | — | — | — | 25 | — | — | — |
| | 0.0175 | — | — | 85 | — | — | — | 30 | 75 | 10 | 30 | — | 20 | — | — |
| | 0.0044 | — | — | 40 | — | — | — | 40 | 50 | 0 | 65 | — | 0 | — | — |
| | 0.0044 | 0 | 0 | — | — | — | — | — | — | — | — | 0 | — | — | — |
| 58 | 5.6050 | C | C | — | — | — | — | — | — | — | — | 99 | — | — | — |
| | 5.6050 | — | — | C | — | — | — | C | C | 65 | 95 | — | C | — | — |
| | 1.1210 | C | C | — | — | — | — | — | — | — | — | C | — | — | — |
| | 1.1210 | — | — | C | — | — | — | C | C | 50 | 80 | — | 90 | — | — |
| | 0.2803 | C | C | — | — | — | — | — | — | — | — | 99 | — | — | — |
| | 0.2803 | — | — | C | — | — | — | C | 99 | 20 | 50 | — | 85 | — | — |
| | 0.0701 | 95 | C | — | — | — | — | — | — | — | — | 90 | — | — | — |
| | 0.0701 | — | — | C | — | — | — | 95 | C | 20 | 20 | — | 75 | — | — |
| | 0.0175 | 20 | 99 | — | — | — | — | — | — | — | — | 60 | — | — | — |
| | 0.0175 | — | — | 90 | — | — | — | 75 | 99 | 0 | 0 | — | 70 | — | — |
| | 0.0044 | — | — | 75 | — | — | — | 20 | 50 | 0 | 0 | — | 20 | — | — |
| | 0.0044 | 0 | 95 | — | — | — | — | — | — | — | — | 0 | — | — | — |
| 59 | 5.6050 | C | C | — | — | — | — | — | — | — | — | C | — | — | — |
| | 5.6050 | — | — | C | — | — | — | C | C | 60 | 10 | — | 90 | — | — |
| | 1.1210 | 80 | C | — | — | — | — | — | — | — | — | 95 | — | — | — |
| | 1.1210 | — | — | 99 | — | — | — | C | 99 | 30 | 0 | — | 50 | — | — |
| | 0.2803 | — | — | 20 | — | — | — | 90 | 70 | 0 | 0 | — | 20 | — | — |
| | 0.2803 | 20 | 90 | — | — | — | — | — | — | — | — | 30 | — | — | — |
| | 0.0701 | — | — | 0 | — | — | — | 75 | 20 | 0 | 0 | — | 0 | — | — |
| | 0.0701 | 0 | 90 | — | — | — | — | — | — | — | — | 0 | — | — | — |
| 60 | 5.6050 | — | — | C | — | — | — | C | — | — | 99 | — | C | 99 | C |
| | 5.6050 | C | C | — | — | — | — | — | — | — | — | C | — | — | — |
| | 1.1210 | C | C | — | — | — | — | — | — | — | — | C | — | — | — |
| | 1.1210 | — | — | C | — | — | — | C | — | — | 95 | — | 95 | 99 | C |
| | 0.2803 | — | — | C | — | — | — | C | — | — | 65 | — | 95 | 95 | C |
| | 0.2803 | C | C | — | — | — | — | — | — | — | — | C | — | — | — |
| | 0.0701 | C | C | — | — | — | — | — | — | — | — | C | — | — | — |
| | 0.0701 | — | — | C | — | — | — | C | — | — | 20 | — | 95 | 80 | C |
| | 0.0175 | — | — | C | — | — | — | 90 | — | — | 0 | — | 50 | 75 | 90 |
| | 0.0175 | 95 | C | — | — | — | — | — | — | — | — | 75 | — | — | — |
| | 0.0044 | — | — | 90 | — | — | — | 0 | — | — | 0 | — | 15 | 0 | 20 |
| | 0.0044 | 0 | 50 | — | — | — | — | — | — | — | — | 0 | — | — | — |
| 61 | 5.6050 | C | C | — | — | — | — | — | — | — | — | 99 | — | — | — |
| | 5.6050 | — | — | C | — | — | — | 95 | C | 40 | 10 | — | 65 | — | — |
| | 1.1210 | 95 | 99 | — | — | — | — | — | — | — | — | 85 | — | — | — |
| | 1.1210 | — | — | C | — | — | — | 0 | 60 | 0 | 0 | — | 0 | — | — |
| | 0.2803 | — | — | 50 | — | — | — | 0 | 0 | 0 | 0 | — | 0 | — | — |
| | 0.2803 | 0 | 60 | — | — | — | — | — | — | — | — | 0 | — | — | — |
| 62 | 5.6050 | C | C | — | — | — | — | — | — | — | — | C | — | — | — |
| | 5.6050 | — | — | C | — | — | — | C | — | — | 95 | — | C | C | C |
| | 1.1210 | C | C | — | — | — | — | — | — | — | — | C | — | — | — |
| | 1.1210 | — | — | C | — | — | — | C | — | — | 90 | — | 95 | C | C |
| | 0.2803 | C | C | — | — | — | — | — | — | — | — | C | — | — | — |
| | 0.2803 | — | — | C | — | — | — | C | — | — | 65 | — | 95 | 99 | 90 |
| | 0.0701 | — | — | C | — | — | — | C | — | — | 75 | — | 90 | C | C |
| | 0.0701 | 99 | C | — | — | — | — | — | — | — | — | 99 | — | — | — |
| | 0.0175 | — | — | 99 | — | — | — | 98 | — | — | 0 | — | 65 | 50 | 98 |
| | 0.0175 | 98 | 99 | — | — | — | — | — | — | — | — | 90 | — | — | — |
| | 0.0044 | 0 | 30 | — | — | — | — | — | — | — | — | 30 | — | — | — |

TABLE 3-continued

| Herbicide Secondary Preemergence |
|---|

0.0044 — — 65 — — — 20 — — 0 — 0 45 20

(D) NO DATA FOR COBU DUE TO POOR OR ERRATIC EMERGENCE.
(C) GREENHOUSE TEMPERATURE FLUCTUATED IN THIS TEST.
(B) POOR RAPE STANDS THROUGHTOUT TEST.
(A) PLANTS SMALLER THAN NORMAL.
(E) DAMPING OFF THROUGHOUT TEST.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-1.5 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil. Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Hetetocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido(1,2-:2',1'-c)-pyrazidiinium salt 5-Bromo-3-isopropyl-6-methyluracil
1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo- 2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-1,3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl-N,N-diisopropylthiolcarbamate cl Acetamides/Acetanilides/Anilines/Amides 2-Chloro-N,N-diallylacetamide
N,N-dimethyl-2,2-diphenylacetamide
N-(2,4-dimethyl-5-[[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts.
Butyl (R)-2-[4-[(5-(trifluoromethyl)-2-pyridinyl)oxy]-phenoxy]-propanoate Ethers 2,4-Dichlorophenyl-4-nitrophenyl ether
2-Chloro-α,α,α-trifluoro-p-tolyl-3-ethoxy-4-nitrodiphenyl ether 5-(2-chloro-4-trifluoromethylphenoxy)-N-methylsulfonyl-2-nitrobenzamide
1'-(Carboethoxy) ethyl 5-[2-chloro-4-(trifluoromethyl)-phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo isomer Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

|      |                                                                                                                    | Weight Percent |
| ---- | ------------------------------------------------------------------------------------------------------------------ | -------------- |
| I.   | Emulsifiable Concentrates                                                                                          |                |
| A.   | Compound of Example No. 3                                                                                          | 11.0           |
|      | Free acid of complex organic phosphate or aromatic or aliphatic hydrophobe base (e.g., GAFAC RE-610, registered trademark of GAF Corp.) | 5.59           |
|      | Polyoxyethylene/polyoxypropylene block copolymer with butanol (e.g., Tergitol XH, registered trademark of Union Carbide Corp.) | 1.11           |
|      | Phenol                                                                                                             | 5.34           |
|      | Monochlorobezene                                                                                                   | 76.96          |
|      |                                                                                                                    | 100.00         |
| B.   | Compound of Example No. 14                                                                                         | 25.00          |
|      | Free acid of complex organic phosphate of aromatic or aliphatic hydrophobe base (e.g., GAFAC RE-610)               | 5.00           |
|      | Polyoxyethylene/polyoxypropylene block copolymer with butanol (e.g., Tergitol XH)                                  | 1.60           |
|      | Phenol                                                                                                             | 4.75           |
|      | Monochlorobenzene                                                                                                  | 63.65          |
|      |                                                                                                                    | 100.00         |
| II.  | Flowables                                                                                                          |                |
| A.   | Compound of Example No. 11                                                                                         | 25.0           |
|      | Methyl cellulose                                                                                                   | 0.3            |
|      | Silica Aerogel                                                                                                     | 1.5            |
|      | Sodium lignosulfonate                                                                                              | 3.5            |
|      | Sodium N-methyl-N-oleyl taurate                                                                                    | 2.0            |
|      | Water                                                                                                              | 67.7           |
|      |                                                                                                                    | 100.0          |
| B.   | Compound of Example No. 18                                                                                         | 45.0           |
|      | Methyl cellulose                                                                                                   | .3             |
|      | Silica aerogel                                                                                                     | 1.5            |
|      | Sodium lignosulfonate                                                                                              | 3.5            |
|      | Sodium N-methyl-N-oleyl taurate                                                                                    | 2.0            |
|      | Water                                                                                                              | 47.7           |
|      |                                                                                                                    | 100.0          |
| III. | Wettable Powders                                                                                                   |                |
| A.   | Compound of Example No. 5                                                                                          | 25.0           |
|      | Sodium lignosulfonate                                                                                              | 3.0            |
|      | Sodium N-methyl-N-oleyl-taurate                                                                                    | 1.0            |
|      | Amorphous silica (synthetic)                                                                                       | 71.0           |
|      |                                                                                                                    | 100.0          |
| B.   | Compound of Example 13                                                                                             | 80.00          |
|      | Sodium dioctyl sulfosuccinate                                                                                      | 1.25           |
|      | Calcium lignosulfonate                                                                                             | 2.75           |
|      | Amorphous silica (synthetic)                                                                                       | 16.00          |
|      |                                                                                                                    | 100.00         |

| | | Weight Percent |
|---|---|---|
| C. | Compound of Example No. 6 | 10.0 |
| | Sodium lignosulfonate | 3.0 |
| | Sodium N-methyl-N-oleyl-taurate | 1.0 |
| | Kaolinite clay | 86.0 |
| | | 100.00 |
| IV. | Dusts | |
| A. | Compound of Example No. 14 | 2.0 |
| | Attapulgite | 98.0 |
| | | 100.0 |
| B. | Compound of Example No. 10 | 60.0 |
| | Montmorillonite | 40.0 |
| | | 100.0 |
| C. | Compound of Example No. 9 | 30.0 |
| | Ethylene glycol | 1.0 |
| | Bentonite | 69.0 |
| | | 100.0 |
| D. | Compound of Example No. 3 | 1.0 |
| | Diatomaceous earth | 99.0 |
| | | 100.0 |
| V. | Granules | |
| A. | Compound of Example No. 2 | 15.0 |
| | Granular attapulgite (20/40 mesh) | 85.0 |
| | | 100.0 |
| B. | Compound of Example No. 10 | 30.0 |
| | Diatomaceous earth (20/40) | 70.0 |
| | | 100.0 |
| C. | Compound of Example No. 12 | 1.0 |
| | Ethylene glycol | 5.0 |
| | Methylene blue | 0.1 |
| | Pyrophyllite | 93.9 |
| | | 100.0 |
| D. | Compound of Example No. 16 | 5.0 |
| | Pyrophyllite (20/40) | 95.0 |
| | | 100.0 |

When operating in according with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New Internation Dictionary*, Second Edition, Unabridged (1961). Thus, the term refers to any substance or medium in which vegetation may take root and grow, and includes not only earth but also compost, manure, muck, humus, loam, silt, mire, clay, sand, and the like, adapted to support plant growth.

Although the invention is described with respect to specific modifications, the details thereof are not to be construed as limitations.

We claim:

1. A compound represented by the formula

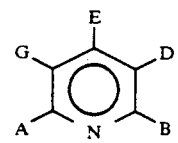

wherein:
one of A and B is selected from the group consisting of fluorinated methyl and chlorofluorinated methyl radicals, and the other is selected from the group consisting of fluorinated methyl, chlorofluorinated methyl, chlorinated methyl, iodinated methyl, alkenyl, and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynloxycarbonyl, cyano, pyridylthiocarbonyl, aminocarbonyl, monoalkylsubstituted aminocarbonyl, and dialkylsubstituted aminocarbonyl or is the same as D; and D is selected from the group consisting of (tetrahydro-2(H)-pyran-2-ylidene)amino, (dihydro-2(3H)-furanylidene)amino, (dihydro-2(3H)-thienylidene)amino, 2(5H)-furanylideneamino, (2-thiazolidinylidene)amino, (1,3-oxathiolan-2-ylidene)amino, (2-morpholinylidene)amino, (1,4-dithian-2-ylidene)amino, (1,3-oxathian-2-ylidene)amino, (1,3-dioxolan-2-ylidene)amino, and (2-pyrrolidinylidene)amino groups, each member of which is optionally substituted on the ring portion with one or more members selected from alkyl, halo, alkylidene, hydroxy, alkoxy, alkylthio, haloalkyl and alkylsulfonyl radicals.

2. A compound according to claim 1 wherein D is (dihydro-2(3H)-furanylidene)amino.

3. A compound according to claim 2 in which one of A and B is trifluoromethyl and the other is difluoromethyl.

4. A compound according to claim 3 in which G is selected from the group consisting of methoxycarbonyl, ethoxycarbonyl, 2-propenoxycarbonyl, and methylthiocarbonyl groups.

5. A compound according to claim 4 in which E is selected from the group consisting of 2-methylpropyl, cyclopropylmethyl, and cyclobutyl groups.

6. A compound according to claim 5 wherein the ring portion of D is substituted at the 3-position with a member selected from the group consisting of methyl, methylthio, fluoro, chloro, and bromo.

7. A compound according to claim 6 in which B is trifluoromethyl.

8. A compound according to claim 7 wherein the ring portion of D is substituted at the 3-position with methyl, G is methoxycarbonyl, and E is 2-methylpropyl.

9. A herbicidal composition containing a carrier and as an active component a compound represented by the formula

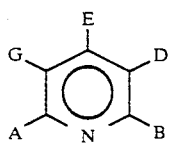

wherein:
one of A and B is selected from the group consisting of fluorinated methyl and chlorofluorinated methyl radicals, and the other is selected from the group consisting of fluorinated methyl, chlorofluorinated methyl, chlorinated methyl, iodinated methyl, alkenyl, and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynloxycarbonyl, cyano, pyridylthiocarbonyl, aminocarbonyl, monoalkylsubstituted aminocarbonyl, and dialkylsubstituted aminocarbonyl or is the same as D; and D is selected from the group consisting of (tetrahydro-2(H)-pyran-2-ylidene)amino, (dihydro-2(3H)-furanylidene)amino, (dihydro-2(3H)-thienylidene)amino, 2(5H)-furanylideneamino, (2-thiazolidinylidene)amino, (1,3-oxathiolan-2-ylidene)amino, (2-morpholinylidene)amino, (1,4-dithian-2-ylidene)amino, (1,3-oxathian-2-ylidene)amino, (1,3-dioxolan-2-ylidene)amino, and (2-pyrrolidinylidene)amino groups, each member of which is optionally substituted on the ring portion with one or more groups selected from alkyl, halo, alkylidene, hydroxy, alkoxy, alkylthio, haloalkyl and alkylsulfonyl radicals.

10. A composition according to claim 9 wherein D is (dihydro-2(3H)-furanylidene)amino.

11. A composition according to claim 10 in which one of A and B is trifluoromethyl and the other is difluoromethyl.

12. A composition according to claim 11 in which G is selected from the group consisting of methoxycarbonyl, ethoxycarbonyl, 2-propenoxycarbonyl, and methylthiocarbonyl groups.

13. A composition according to claim 12 in which E is selected from the group consisting of 2-methylpropyl, cyclopropylmethyl, and cyclobutyl groups.

14. A composition according to claim 13 wherein the ring portion of D is substituted at the 3-position with a member selected from the group consisting of methyl, methylthio, fluoro, chloro, and bromo.

15. A composition according to claim 14 in which B is trifluoromethyl.

16. A composition according to claim 15 wherein the ring portion of D is substituted at the 3-position with methyl, G is methoxycarbonyl, and E is 2-methylpropyl.

* * * * *

UNITED STATES PATENT AND TRADEMARK OFFICE
CERTIFICATE OF CORRECTION

PATENT NO. : 5,129,943
DATED : July 14, 1992
INVENTOR(S) : Hedge, et al

It is certified that error appears in the above-indentified patent and that said Letters Patent is hereby corrected as shown below:

| | | |
|---|---|---|
| Col. 2 | Line 5 | Delete "2(5H)furanylideneamino" and insert --2(5H)-furanylideneamino--. |
| Col. 3 | Lines 12 | Delete "trifluoroacetcacetate" and insert --trifluoroacetoacetate--. |
| Col. 3 | Line 45 | Delete "ar" and insert --are--. |
| Col. 4 | Line 48 | Delete "zl" and insert --ml--. |
| Col. 5 | Line 16 | Delete "$^{19}$NMR" and insert --$^{19}$F NMR--. |
| Col. 5 | Line 51 | Delete "4-dihydropyridine" and insert --1,4-dihydropyridine--. |
| Col. 6 | Line 63 | Delete "I" and insert --1--. |

UNITED STATES PATENT AND TRADEMARK OFFICE
CERTIFICATE OF CORRECTION

PATENT NO. : 5,129,943
DATED : July 14, 1992
INVENTOR(S) : Hedge, et al

It is certified that error appears in the above-indentified patent and that said Letters Patent is hereby corrected as shown below:

Col. 7   Line 31    Delete "5-chlorocabonyl" and insert --5-chlorocarbonyl--.

Col. 17  Line 39    Delete "2(3)-furanylidene" and insert --2(3H)-furanylidene--.

Signed and Sealed this

Sixth Day of September, 1994

Attest:

BRUCE LEHMAN

Attesting Officer    Commissioner of Patents and Trademarks